(12) United States Patent
Adams et al.

(10) Patent No.: US 7,001,921 B1
(45) Date of Patent: Feb. 21, 2006

(54) CELL ADHESION INHIBITORS

(75) Inventors: Steven P. Adams, Andover, MA (US);
Ko-Chung Lin, Lexington, MA (US);
Wen-Cherng Lee, Lexington, MA
(US); Alfredo C. Castro, Woburn, MA
(US); Craig N. Zimmerman,
Somerville, MA (US); Charles E. Hammond, Burlington, MA (US);
Yu-Sheng Liao, Waltham, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 10/625,626

(22) Filed: Jul. 24, 2003

Related U.S. Application Data

(60) Continuation of application No. 09/935,461, filed on Aug. 22, 2001, now Pat. No. 6,624,152, which is a division of application No. 08/376,372, filed on Jan. 23, 1995, now Pat. No. 6,306,840.

(51) Int. Cl.
*A61K 31/195* (2006.01)
*C07C 233/00* (2006.01)
(52) U.S. Cl. .................... 514/557; 514/613; 564/123
(58) Field of Classification Search .............. 514/109, 514/76, 79, 114, 557, 613; 546/335; 558/166, 558/445; 562/429, 430, 437, 443; 564/123
See application file for complete search history.

(56) References Cited

U.S. PATENT DOCUMENTS

| 4,725,583 | A | * | 2/1988 | Luly et al. ............... 514/18 |
| 4,826,815 | A | * | 5/1989 | Luly et al. ............... 514/19 |
| 5,260,277 | A | | 11/1993 | McKenzie |
| 5,314,902 | A | | 5/1994 | Tjoeng et al. |
| 5,399,570 | A | * | 3/1995 | Klingler et al. ............ 514/327 |
| 5,434,188 | A | | 7/1995 | Boschelli et al. |

FOREIGN PATENT DOCUMENTS

| EP | 0 460 679 | 12/1991 |
| EP | 0 519 748 | 12/1992 |
| EP | 0 565 896 | 10/1993 |
| WO | WO 92 00995 | 7/1991 |
| WO | WO 92 08464 | 11/1991 |
| WO | WO 93 08823 | 11/1991 |
| WO | WO 93 09795 | 5/1993 |
| WO | WO 94 02445 | 7/1993 |
| WO | WO 94 15958 | 1/1994 |
| WO | WO 94 23714 | 10/1994 |
| WO | WO 95 15973 | 12/1994 |

OTHER PUBLICATIONS

"Reach-through Claims", Baker Botts LLP/News & Events/In Print, Apr. 12, 2002, htp://www.bakerbotts.com/news.*
Abraham, W.M., et al., "α4-Intergrins Mediate Antigen-induced Late Bronchial Responses and Prolonged Airway Hyperresponsiveness in Sheep", J. Clin. Invest., 93, pp. 776-787 (1994).
Baldwin, J.E., et al., CA 108: 127408t, 1998.
Chen, S.T., et al., CA 115:159749r, 1991.
Chisolm, P.L., et al., "Monoclonal Antibodies to the Integrin α-4 Subunit Inhibit the Murine contact Hypersensitivity Response," Eur. J. Immunol., 23, pp. 682-688 (1993).
Elices, M.J., et al., "Expression and functional Significance of Alternatively Spliced CS1 Fibronectin in Rheumatoid Arthritis Microvasculature,", J. Chin. Invest., 93, pp. 405-416 (1994).
Ferguson, T.A., et al., "Two Integrin-binding Peptides Abrogate T Cell-Mediated Immune Responses in Vivo", Proc. Natl. Acad. Sci. USA, 88, pp. 8072-8075 (1991).
Ferguson, T.A. and T.S. Kupper, "Antigen-Independent Processes in Antigen-Specific Immunity", J. Immunol., 150, pp. 117-1182 (1993).
Greenstein et al., Synthesis and Activity of NacSerAspLysPro Analoguesnon Cellular Interactions Between T-Cell and Erythrocytes in Rosette Formation:, J. Med. Chem. 1998, 33, 2122-2127.
Goodman et al., "Synthesis and Conformation of Sequential Polypeptides of L-Alanine and Beta-Aminobutyric Acid", Macromolecules, 9:1-6, 1976.
Gruszecki, W., et al., "Diacylamines—Perfect Acylating Agents for Peptide Synthesis", Liebigs Ann. Chem., p 331-336, 1988.
Helmer, M.E., "VLA Proteins in the Integrin Family: Structures, Functions, and their Role in Leukocytes", Ann. Rev. Immunol., 8, pp. 365-400 (1990).
Jiang, J., et al., "Approaches Toward the Total Synthesis of Astins A, B, and C", Tet. Let., 35(14), pp 2121-2124, 1994.
Jiang et al., "Synthesis and Conformation of Sequential Polypeptides of L-Alanine and Beta-Aminobutyric Acid", Tetrahedron Letters, 35:2121-4, 1994.
Kim et al., "Inhibition of [123] I-Labeled Ristocetin Binding to *Micrococcus luteus* cells by the Peptides Related to Bacterial Cell Wall Mucopeptide Precursors: Quantitative Structure-Activity Relationships", J. Med. Chem., 1989, 32, 84-93.
Komoriya, A., et al., "The Minimal Essential Sequence for a Major Cell Type-specific Adhesion Site (CSI) ithin the Alternatively spliced Type III Connecting Segment Domain of Fibronectin is Leucine-Aspartic Acid-Valine", J. Biol. Chem., 266, pp. 15075-15079 (1991).

(Continued)

Primary Examiner—Joseph K. McKane
Assistant Examiner—Janet L Coppins
(74) Attorney, Agent, or Firm—Steptoe & Johnson LLP

(57) ABSTRACT

The present invention relates to novel compounds that are useful for inhibition and prevention of cell adhesion and cell adhesion-mediated pathologies. This invention also relates to pharmaceutical formulations comprising these compounds and methods of using them for inhibition and prevention of cell adhesion and cell adhesion-mediated pathologies. The compounds and pharmaceutical compositions of this invention can be used as therapeutic or prophylactic agents. They are particularly well-suited for treatment of many inflammatory and autoimmune diseases.

9 Claims, No Drawings

OTHER PUBLICATIONS

Lampi, K.J., et al., CA 118:73514t, 1993.

Lobb, R.R. and Hemler, M.E., "The Pathophysiologic Role of α4 Integrins In Vivo", J. Clin. Invest., 94, pp. 1722-1728 (1994).

Molossi, S., et al., "Blockade of Very Late Antigen-4 Integrin Binding to Fibronectin with Connecting Segment-1 Peptide Reduces Accelerated Coronary Arteriopathy in Rabbit Cardiac Allografts", J. Clin. Invest., 95, pp. 2601-2610 (1995).

Morales-Ducret, J., et al., "α4/β1 Integrin (VLA-4) Ligands in Arthritis", J. Immunol., 149, pp. 1424-1431 (1992).

Nowlin, D.M., "A Novel Cyclic Peptide Inhibits α4β1 and α5β1 Integrin-mediated Cell Adhesion", J. Biol. Chem., 268, pp. 20352-20359 (1993).

Subasinghe et al., "Synthesis and Acyclic and Dehydroaspartic Acid Analogues of Ac-Asp-Glu-OH and Their Inhibition of Rat Brain N-Acetylated Alpha-Linked Acidic Dipeptidase (NAALA Dipeptidase)", Journal of Medicinal Chemistry, 33:2734-2744, 1990.

Thierry et al., "Synthesis and Activity of NacSerAspLysPro Analogues on Cellular Interactions between T-Cell and Erythrocytes in Rosette Formation", J. Med. Chem. 1990, 33, 2122-2127.

Wayner, E.A. and Kovach, N.L., "Activation-dependent Recognition by Hematopoietic Cells of the LDV Sequence in the V Region of Fibronectin", J. Cell. Biol., 116, pp. 489-497 (1992).

Yednock, T.A., et al., "Prevention of Experimental Autoimmune Encephalomyelitis by Antibodies Against α4β1 Integrin", Nature, 356, pp. 63-66 (1992).

* cited by examiner

CELL ADHESION INHIBITORS

CROSS-REFERENCE TO RELATED APPLICATIONS

This application is a continuation of U.S. patent application Ser. No. 09/935,461, filed Aug. 22, 2001 now U.S. Pat. No. 6,624,152, which is a divisional of U.S. patent application Ser. No. 08/376,372, filed Jan. 23, 1995, U.S. Pat. No. 6,306,840, both of which are herein incorporated by reference.

TECHNICAL FIELD OF THE INVENTION

The present invention relates to novel compounds that are useful for inhibition and prevention of cell adhesion and cell adhesion-mediated pathologies. This invention also relates to pharmaceutical formulations comprising these compounds and methods of using them for inhibition and prevention of cell adhesion and cell adhesion-mediated pathologies. The compounds and pharmaceutical compositions of this invention can be used as therapeutic or prophylactic agents. They are particularly well-suited for treatment of many inflammatory and autoimmune diseases.

BACKGROUND OF THE INVENTION

Cell adhesion is a process by which cells associate with each other, migrate towards a specific target or localize within the extra-cellular matrix. As such, cell adhesion constitutes one of the fundamental mechanisms underlying numerous biological phenomena. For example, cell adhesion is responsible for the adhesion of hematopoietic cells to endothelial cells and the subsequent migration of those hemopoietic cells out of blood vessels and to the site of injury. As such, cell adhesion plays a role in pathologies such as inflammation and immune reactions in mammals.

Investigations into the molecular basis for cell adhesion have revealed that various cell-surface macromolecules—collectively known as cell adhesion molecules or receptors—mediate cell—cell and cell-matrix interactions. For example, proteins of the superfamily called "integrins" are key mediators in adhesive interactions between hematopoietic cells and their microenvironment (M. E. Hemler, "VLA Proteins in the Integrin Family: Structures, Functions, and Their Role on Leukocytes.", *Ann. Rev. Immunol.*, 8, p. 365 (1990)). Integrins are non-covalent heterodimeric complexes consisting of two subunits called α and β. There are at least 12 different α subunits (α1–α6, α-L, α-M, α-X, α-IIB, α-V and α-E) and at least 9 different β(β1–β9) subunits. Based on the type of its α and β subunit components, each integrin molecule is categorized into a subfamily.

α4β1 integrin, also known as very late antigen-4 ("VLA-4"), CD49d/CD29, is a leukocyte cell surface receptor that participates in a wide variety of both cell—cell and cell-matrix adhesive interactions (M. E. Hemler, *Ann. Rev. Immunol.*, 8, p. 365 (1990)). It serves as a receptor for the cytokine-inducible endothelial cell surface protein, vascular cell adhesion molecule-1 ("VCAM-1"), as well as to the extracellular matrix protein fibronectin ("FN") (Ruegg et al., *J. Cell Biol.*, 177, p. 179 (1991); Wayner et al., *J. Cell Biol.*, 105, p. 1873 (1987); Kramer et al., *J. Biol. Chem.* 264, p. 4684 (1989); Gehlsen et al. *Science*, 24, p. 1228 (1988)). Anti-VLA4 monoclonal antibodies ("mAb's") have been shown to inhibit VLA4-dependent adhesive interactions both in vitro and in vivo (Ferguson et al. *Proc. Natl. Acad. Sci.*, 88, p. 8072 (1991); Ferguson et al., *J. Immunol.*, 150, p. 1172 (1993)). Results of in vivo experiments suggest that this inhibition of VLA-4-dependent cell adhesion may prevent or inhibit several inflammatory and autoimmune pathologies (R. L. Lobb et al., "The Pathophysiologic Role of α4 Integrins In Vivo", *J. Clin. Invest.*, 94, pp. 1722–28 (1994)).

In order to identify the minimum active amino acid sequence necessary to bind VLA-4, Komoriya et al. ("The Minimal Essential Sequence for a Major Cell Type-Specific Adhesion Site (CS1) Within the Alternatively Spliced Type III Connecting Segment Domain of Fibronectin Is Leucine-Aspartic Acid-Valine", *J. Biol. Chem.*, 266 (23), pp. 15075–79 (1991)) synthesized a variety of overlapping peptides based on the amino acid sequence of the CS-1 region (the VLA-4 binding domain) of a particular species of fibronectin. They identified an 8-amino acid peptide, Glu-Ile-Leu-Asp-Val-Pro-Ser-Thr [SEQ ID NO: 1], as well as two smaller overlapping pentapeptides, Glu-Ile-Leu-Asp-Val [SEQ ID NO: 2] and Leu-Asp-Val-Pro-Ser [SEQ ID NO: 3], that possessed inhibitory activity against FN-dependent cell adhesion. These results suggested the tripeptide Leu-Asp-Val as a minimum sequence for cell-adhesion activity. It was later shown that Leu-Asp-Val binds only to lymphocytes that express an activated form of VLA-4, thus bringing into question the utility of such a peptide in vivo (E. A. Wayner et al., "Activation-Dependent Recognition by Hematopoietic Cells of the LDV Sequence in the V Region of Fibronectin", *J. Cell. Biol.*, 116(2), pp. 489–497 (1992)). However, certain larger peptides containing the LDV sequence were subsequently shown to be active in vivo [T. A. Ferguson et al., "Two Integrin Binding Peptides Abrogate T-cell-Mediated Immune Responses In Vivo", *Proc. Natl. Acad. Sci. USA*, 88, pp. 8072–76 (1991); and S. M. Wahl et al., "Synthetic Fibronectin Peptides Suppress Arthritis in Rats by Interrupting Leukocyte Adhesion and Recruitment", *J. Clin. Invest.*, 94, pp. 655–62 (1994)].

A cyclic pentapeptide, Arg-Cys-Asp-TPro-Cys (wherein TPro denotes 4-thioproline), which can inhibit both VLA-4 and VLA-5 adhesion to FN has also been described (D. M. Nowlin et al. "A Novel Cyclic Pentapeptide Inhibits α4β1 and α5β1 Integrin-mediated Cell Adhesion", *J. Biol. Chem.*, 268(27), pp. 20352–59 (1993); and PCT publication PCT/US91/04862). This peptide was based on the tripeptide sequence Arg-Gly-Asp from FN which had been known as a common motif in the recognition site for several extracellular-matrix proteins.

Despite these advances, there remains a need for small, specific inhibitors of VLA-4-dependent cell adhesion. Ideally, such inhibitors would be semi-peptidic or non-peptidic so that they may be orally administered. Such compounds would provide useful agents for treatment, prevention or suppression of various pathologies mediated by cell adhesion and VLA-4 binding.

SUMMARY OF THE INVENTION

The present invention solves this problem by providing novel non-peptidic compounds that specifically inhibit the binding of ligands to VLA-4. These compounds are useful for inhibition, prevention and suppression of VLA-4-mediated cell adhesion and pathologies associated with that adhesion, such as inflammation and immune reactions. The compounds of this invention may be used alone or in combination with other therapeutic or prophylactic agents to inhibit, prevent or suppress cell adhesion. This invention also provides pharmaceutical formulations containing these VLA-4-mediated cell adhesion inhibitors and methods of using the compounds and compositions of the invention for inhibition of cell adhesion.

According to one embodiment of this invention, these novel compounds, compositions and methods are advantageously used to treat inflammatory and immune diseases. The present invention also provides methods for preparing the compounds of this invention and intermediates useful in those methods.

DETAILED DESCRIPTION OF THE INVENTION

Definitions

As used herein, the term "alkyl", alone or in combination, refers to a straight-chain or branched-chain alkyl radical containing from 1 to 10, preferably from 1 to 6 and more preferably from 1 to 4, carbon atoms. Examples of such radicals include, but are not limited to, methyl, ethyl, n-propyl, isopropyl, n-butyl, isobutyl, sec-butyl, tert-butyl, pentyl, iso-amyl, hexyl, decyl and the like.

The term "alkenyl", alone or in combination, refers to a straight-chain or branched-chain alkenyl radical containing from 2 to 10, preferably from 2 to 6 and more preferably from 2 to 4, carbon atoms. Examples of such radicals include, but are not limited to, ethenyl, E- and Z-propenyl, isopropenyl, E- and Z-butenyl, E- and Z-isobutenyl, E- and Z-pentenyl, decenyl and the like.

The term "alkynyl", alone or in combination, refers to a straight-chain or branched-chain alkynyl radical containing from 2 to 10, preferably from 2 to 6 and more preferably from 2 to 4, carbon atoms. Examples of such radicals include, but are not limited to, ethynyl (acetylenyl), propynyl, propargyl, butynyl, hexynyl, decynyl and the like.

The term "cycloalkyl", alone or in combination, refers to a cyclic alkyl radical containing from 3 to 8, preferably from 3 to 6, carbon atoms. Examples of such cycloalkyl radicals include, but are not limited to, cyclopropyl, cyclobutyl, cyclopentyl, cyclohexyl and the like.

The term "cycloalkenyl", alone or in combination, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, cyclopentadienyl and the like.

The term "aryl" refers to a carbocyclic aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl" groups, as defined in this application may independently contain one to three substituents which are independently selected from the group consisting of hydrogen, halogen, hydroxyl, amino, nitro, trifluoromethyl, trifluoromethoxy, alkyl, alkenyl, alkynyl, cyano, carboxy, carboalkoxy, Ar'-substituted alkyl, Ar'-substituted alkenyl or alkynyl, 1,2-dioxymethylene, 1,2-dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl, Ar'-substituted acyl, Ar'-substituted alkylcarbonyloxy, Ar'-substituted carbonylamino, Ar'-substituted amino, Ar'-substituted oxy, Ar'-substituted carbonyl, alkylcarbonylamino, Ar'-substituted alkylcarbonylamino, alkoxy-carbonylamino, Ar'-substituted alkoxycarbonyl-amino, Ar'-oxycarbonylamino, alkylsulfonylamino, mono- or bis-(Ar'-sulfonyl)amino, Ar'-substituted alkyl-sulfonylamino, morpholinocarbonylamino, thiomorpholinocarbonylamino, N-alkyl guanidino, N—Ar' guanidino, N—N-(Ar',alkyl) guanidino, N,N-(Ar',Ar')guanidino, N,N-dialkyl guanidino, N,N,N-trialkyl guanidino, N-alkyl urea, N,N-dialkyl urea, N—Ar' urea, N,N-(Ar',alkyl) urea and N,N-(Ar')$_2$ urea; wherein "Ar'" is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy", alone or in combination, refers to a radical of formula alkenyl-O—, wherein the term "alkenyl" is as defined above provided that the radical is not an enol ether. Examples of suitable alkenoxy radicals include, but are not limited to, allyloxy, E- and Z-3-methyl-2-propenoxy and the like.

The term "alkynyloxy", alone or in combination, refers to a radical of formula alkynyl-O—, wherein the term "alkynyl" is as defined above provided that the radical is not an ynol ether. Examples of suitable alkynoxy radicals include, but are not limited to, propargyloxy, 2-butynyloxy and the like.

The term "thioalkoxy" refers to a thioether radical of formula alkyl-S—, wherein alkyl is as defined above.

The term "alkylamino", alone or in combination, refers to a mono- or di-alkyl-substituted amino radical (i.e., a radical of formula alkyl-NH— or (alkyl)$_2$—N—), wherein the term "alkyl" is as defined above. Examples of suitable alkylamino radicals include, but are not limited to, methylamino, ethylamino, propylamino, isopropylamino, t-butylamino, N,N-diethylamino and the like.

The term "alkenylamino", alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino", alone or in combination, refers to a radical of formula alkynyl-NH— or (alkynyl)$_2$N—, wherein the term "alkenyl" is as defined above, provided that the radical is not an enamine. An example of such alkynylamino radicals is the propargyl amino radical.

The term "aryloxy", alone or in combination, refers to a radical of formula aryl-O—, wherein aryl is as defined above. Examples of aryloxy radicals include, but are not limited to, phenoxy, naphthoxy, pyridyloxy and the like.

The term "arylamino", alone or in combination, refers to a radical of formula aryl-NH—, wherein aryl is as defined above. Examples of arylamino radicals include, but are not limited to, phenylamino (anilido), naphthylamino, 2-, 3- and 4-pyridylamino and the like.

The term "biaryl", alone or in combination, refers to a radical of formula aryl—aryl-, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aryl-fused cycloalkyl", alone or in combination, refers to a cycloalkyl radical which shares two adjacent atoms with an aryl radical, wherein the terms "cycloalkyl" and "aryl" are as defined above. An example of an aryl-fused cycloalkyl radical is the benzofused cyclobutyl radical.

The term "aliphatic acyl", alone or in combination, refers to radicals of formula alkyl-CO—, alkenyl-CO— and alkynyl-CO-derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl, methylpropiolyl and the like.

The term "aromatic acyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The terms "morpholinocarbonyl" and "thiomorpholinocarbonyl", alone or in combination with other terms, refer to an N-carbonylated morpholino and an N-carbonylated thiomorpholino radical, respectively.

The term "alkylcarbonylamino", alone or in combination, refers to a radical of formula alkyl-CONH, wherein the term "alkyl" is as defined above.

The term "alkoxycarbonylamino", alone or in combination, refers to a radical of formula alkyl-OCONH—, wherein the term "alkyl" is as defined above.

The term "alkylsulfonylamino", alone or in combination, refers to a radical of formula alkyl-SO$_2$NH—, wherein the term "alkyl" is as defined above.

The term "arylsulfonylamino", alone or in combination, refers to a radical of formula aryl-SO$_2$NH—, wherein the term "aryl" is as defined above.

The term "N-alkylurea", alone or in combination, refers to a radical of formula alkyl-NH—CO—NH—, wherein the term "alkyl" is as defined above.

The term "N-arylurea", alone or in combination, refers to a radical of formula aryl-NH—CO—NH—, wherein the term "aryl" is as defined above.

The term "halogen" means fluorine, chlorine, bromine and iodine.

The term "leaving group" generally refers to groups readily displaceable by a nucleophile, such as an amine, and alcohol or a thiol nucleophile. Such leaving groups are well known and include carboxylates, N-hydroxysuccinimide, N-hydroxybenzotriazole, halogen (halides), triflates, tosylates, mesylates, alkoxy, thioalkoxy and the like.

The terms "activated derivative of a suitably protected α-amino acid" and "activated substituted-phenylacetic acid derivative" refer to the corresponding acyl halides (e.g. acid fluoride, acid chloride and acid bromide), corresponding activated esters (e.g. nitrophenyl ester, the ester of 1-hydroxybenzotriazole, HOBT, or the ester of hydroxysuccinimide, HOSu), and other conventional derivatives within the skill of the art.

In view of the above definitions, other chemical terms used throughout this application can be easily understood by those of skill in the art. Terms may be used alone or in any combination thereof. The preferred and more preferred chain lengths of the radicals apply to all such combinations.

This invention provides compounds which are capable of inhibiting VLA-4-mediated cell adhesion by inhibiting the binding of ligands to that receptor. These compounds are represented by formula (I):

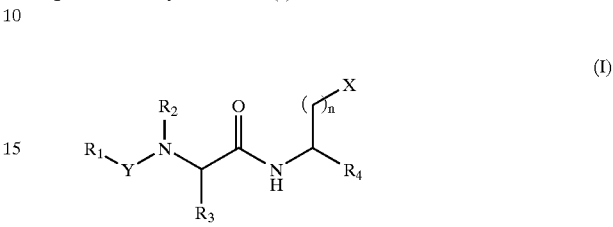

and pharmaceutically acceptable derivatives thereof; wherein:

X is selected from the group consisting of —CO$_2$H, —PO$_3$—H, —SO$_2$R$_5$, —SO$_3$H and —OPO$_3^-$H;

wherein R$_5$ is selected from the group consisting of alkyl, alkenyl, alkynyl, cycloalkyl, cycloalkenyl, aryl, aryl-substituted alkyl, and aryl-substituted alkenyl or alkynyl;

Y is selected from the group consisting of —CO—, SO$_2$— and —PO$_2$—;

R$_1$ is selected from the group consisting of alkyl, alkenyl, alkynyl, cycloalkyl, aryl-fused cycloalkyl, cycloalkenyl, aryl, aryl-substituted alkyl ("aralkyl"), aryl-substituted alkenyl or alkynyl, cycloalkyl-substituted alkyl, cycloalkenyl-substituted cycloalkyl, biaryl, alkoxy, alkenoxy, alkynoxy, aryl-substituted alkoxy ("aralkoxy"), aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarbonyl-substituted alkyl;

R$_2$ is selected from the group consisting of hydrogen, aryl, alkyl, alkenyl or alkynyl, cycloalkyl, cycloalkenyl, and aryl-substituted alkyl;

R$_3$ is selected from the group consisting of alkyl, alkenyl, alkynyl, cycloalkyl, cycloalkenyl, aralkyl, aryl-substituted alkenyl or alkynyl, hydroxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, acylamino-substituted alkyl, alkylsulfonylamino-substituted alkyl, arylsulfonylamino-substituted alkyl, morpholino-alkyl, thiomorpholino-alkyl, morpholino carbonyl-substituted alkyl, thiomorpholinocarbonyl-substituted alkyl, [N-(alkyl, alkenyl or alkynyl)- or N,N-[dialkyl, dialkenyl, dialkynyl or (alkyl,alkenyl)-amino]carbonyl-substituted alkyl, carboxyl-substituted alkyl, and amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, phenylalanine, tyrosine, tryptophan, proline, alanine, ornithine, histidine, glutamine, valine, threonine, serine, aspartic acid, beta-cyanoalanine, and allothreonine;

$R_4$ is selected from the group consisting of aryl, alkyl, cycloalkyl, alkenyl, cycloalkenyl, alkynyl and aryl-substituted alkyl; and n is 0, 1 or 2.

A "pharmaceutically acceptable derivative" denotes any pharmaceutically acceptable salt, ester, salt of such ester, amide or salt of such amide of a compound of this invention. The invention also includes any other compound which, upon administration to a patient, is capable of providing (directly or indirectly) a compound of this invention (e.g. a prodrug). The invention also includes metabolites or residues of a compound of this invention characterized by the ability to inhibit, prevent or suppress cell adhesion and cell adhesion-mediated pathologies.

In another preferred embodiment of this invention, $R_1$ is selected from the group consisting of benzyloxy, cyanomethyl, cyclohexylmethyl, methyl, n-hexyl, N-phenylamino, phenyl, phenylcarbonyl, phenyl-methyl, t-butoxy, t-butylamino, 1-indanyl, 1-naphthylmethyl, 1-phenylcyclopropyl, 2-(4-hydroxy-phenyl)ethyl, 2-(benzyloxycarbonylamino)-phenylmethyl, 2-(bis(phenylsulfonyl)amino)-phenylmethyl, 2-(N'-phenylurea)phenylmethyl, 2-aminophenylmethyl, 2-benzamidophenylmethyl, 2-bromo-4-hydroxy-5-methoxyphenylmethyl, 2-hydroxyphenylmethyl, 2-naphthylmethyl, 2-phenylethyl, 2-pyridylmethyl, 2-quinolinyl, 2-[4-(N'-phenylurea)phenyl]-ethyl, 3(benzyloxycarbonylamino)-phenylmethyl, 3-(N'-phenylurea)phenylmethyl, 3-(N'-phenylurea) propyl, 3-(phenylsulfonamido)-phenylmethyl, 3-acetamidophenyl-methyl, 3-amino-phenylmethyl, 3-benzamidophenylmethyl, 3-hydroxy-4-(N'-phenylurea)-phenylmethyl, 3-hydroxyphenylmethyl, 3-indolyl, 3-methoxy-4-(N'-phenylurea)-phenylmethyl, 3-methoxy-4-(N'-(2-methylphenyl)urea)-phenylmethyl, 3-methyl-4-(N'-phenylurea)-phenylmethyl, 3-nitrophenylmethyl, 3-phenylpropyl, 3-pyridylmethyl, 4-(2-aminobenzamido)-phenylmethyl, 4-(benzamido)phenylmethyl, 4-(benzyloxycarbonylamino)-phenylmethyl, 4-(morpholinocarbonylamino)-phenylmethyl, 4-(N'-(2-chlorophenyl)urea)-phenylmethyl, 4-(N'-(2-chlorophenyl)urea)-3-methoxyphenylmethyl, 4-(N'-(2-ethylphenyl)urea)-phenylmethyl, 4-(N'-(2-isopropylphenyl)urea)-phenylmethyl, 4-(N'-(2-methoxyphenyl)urea)phenylmethyl, 4-(N'-(2-methyl-3-pyridyl)urea)-phenylmethyl, 4-(N'-(2-nitrophenyl)urea)-phenylmethyl, 4-(N'-(2-pyridyl)urea)-phenylmethyl, 4-(N'-(2-t-butylphenyl)urea)-phenylmethyl, 4-(N'-(2-thiazolyl)urea)-phenylmethyl, 4-(N'-(3-chlorophenyl)urea)-phenylmethyl, 4-(N'-(3-methoxyphenyl)urea)-phenylmethyl, 4-(N'-(3-pyridyl)urea)-phenylmethyl, 4-(N'-(4-pyridyl)urea)-phenylmethyl, 4-(N'-(3-methylphenyl)urea)-phenylmethyl, 4-(N'-(2-methylphenyl)-urea)-phenylmethyl, 4-(N'-benzylurea)-phenylmethyl, 4-(N'-cyclohexylurea)-phenylmethyl, 4-(N'-ethylurea)-phenylmethyl, 4-(N'-isopropylurea)-phenylmethyl, 4-(N'-methylurea)phenylmethyl, 4-(N'-p-toluylurea)-phenylmethyl, 4-(N'-phenylurea)phenyl, 4-(N'-phenylurea)phenylamino, 4-(N'-phenylurea)phenylmethyl, 4-(N'-t-butylurea)-phenylmethyl, 4-(phenylaminocarbonylamino-methyl)-phenyl, 4-(phenylsulfonamido)-phenylmethyl, 4-(t-butoxycarbonylamino)-phenylmethyl, 4-acetamidophenylmethyl, 4-amino-phenylamino, 4-aminophenylmethyl, 4-benzamidophenylmethyl, 4-chlorophenylmethyl, 4-hydroxy-3-nitrophenylmethyl, 4-hydroxyphenylmethyl, 4-methoxyphenylmethyl, 4-nitrophenylamino, 4-nitrophenylmethyl, 4-phenacetamidophenylmethyl, 4-phenylphenylmethyl, 4-pyridylmethyl, 4-trifluoromethylphenylmethyl, 4-[2-(N'-methylurea)benzamido]-phenylmethyl, 4-(N'-(2-methylphenyl)urea) phenyl-methyl, 4-(N'-phenyl-N"-methylguanidino)phenylmethyl, 5-(N'-phenylurea)pentyl, 5-(N'-t-butylurea)pentyl, 2,2-dimethylpropyl, 2,2-diphenylmethyl, 2,3-benzocyclobutyl, 3,4-dihydroxyphenylmethyl, 3,5-dimethoxy-4-hydroxyphenylmethyl, 4-(1-indolecarboxylamino)-phenylmethyl, 6-methoxy-5-(N'-(2-methylphenyl)urea)-2-pyridylmethyl, 4-(1,3-benzoxazol-2-ylamino)-phenylmethyl and 4-(1,3-imidazol-2-ylamino)-phenylmethyl.

Most preferably, $R_1$ is selected from the group consisting of 4-hydroxyphenylmethyl, 3-methoxy-4-(N'-phenylurea)-phenylmethyl, 4-(N'-phenylurea)-phenylmethyl, 4-(N'-(2-methylphenyl)urea)-phenylmethyl, 4-(N'-(2-pyridyl)-urea)-phenylmethyl, 3-methoxy-4-(N'-(2-methylphenyl)urea)-phenylmethyl and 6-methoxy-5-(N'-(2-methylphenyl)urea)-2-pyridylmethyl.

In an alternate preferred embodiment $R_1$ is an aryl-substituted $C_1$–$C_4$ alkyl group. More preferably, $R_1$ is a (N—Ar'-urea)-para-substituted arylalkyl group. Most preferably, $R_1$ is a (N—Ar'-urea)-para-substituted phenylmethyl group.

According to another preferred embodiment, $R_2$ is selected from the group consisting of hydrogen, methyl and phenacyl. Most preferably, $R_2$ is hydrogen.

According to another preferred embodiment, $R_3$ is selected from the group consisting of 2-(methylsulfonyl)-ethyl, 3-(hyrdoxypropylthio)-methyl, 4-(methylsulfonylamino)-butyl, 4-acetylaminobutyl, aminomethyl, benzyl, butyl, hydroxymethyl, isobutyl, methyl, methylthiomethyl, phenylmethyl, propyl, 4-(benzyloxycarbonylamino)-butyl, N,N-(methylpropargyl) amino, 2-(methylthio)-ethyl, 2-(morpholino-N-carbonyl)ethyl, 2-(N-morpholino)-ethyl, 2-(N,N-dimethylamino)ethyl, 4-amino-butyl, 4-benzyloxyphenylmethyl, 2-benzylthiomethyl, t-butoxycarbonylaminomethyl, sec-butyl, t-butyl, N,N-dimethylaminocarbonylmethyl, 1,1-ethano*, 4-hydroxyphenylmethyl, 1-hydroxyethyl, 1-methoxyethyl, 4-methoxyphenylmethyl, benzyloxy-methyl, benzylthio-methyl, carbonylmethyl, 2-methylsulfinyl-ethyl, morpholino-N-carbonylmethyl, thiomorpholino-N-carbonylmethyl, 2-phenylethyl, asparagine side-chain, proline side-chain and 2-thiazolyl-methyl.

* The amino acid side chain derived from 1-amino-cyclopropylcarboxylic acid.

Most preferably, $R_3$ is selected from the group consisting of isobutyl, 2-(methylthio)-ethyl, 3(hydroxypropylthio)-methyl, 2-(methylsulfonyl)-ethyl and 4-acetylamino-butyl, 4-(methylsulfonylamino)-butyl.

According to yet another embodiment, $R_4$ is selected from the group consisting of 4-carbomethoxy-phenyl, 4-carboxyphenyl, 4-fluorophenyl, 4-methoxyphenyl, benzyl, methyl, phenyl, phenylmethyl, phenylethyl, 4-chlorophenyl, 3,4-difluorophenyl, 3,4-dimethoxyphenyl, 2-methoxyphenyl, 3-methoxyphenyl, 4-methoxyphenyl, 2-nitrophenyl and 3-pyridyl. More preferably, $R_4$ is selected from the group consisting 4-methoxyphenyl, 3,4-dimethoxyphenyl, 4-fluorophenyl, 4-carboxyphenyl, 4-carbomethoxyphenyl, phenylethyl and phenylmethyl.

In another preferred embodiment Y is CO, $CH_2$ or $SO_2$. Most preferably, Y is CO.

According to another preferred embodiment, X in formula (I) is COOH.

According to yet another preferred embodiment, n is 1.

Examples of some preferred compounds of this invention wherein X is a carboxyl group and n is 1 are provided in Table 1.

TABLE 1

(I')

$$\text{R}_1-\text{Y}-\text{N}(\text{R}_2)-\text{CH}(\text{R}_3)-\text{C}(=\text{O})-\text{NH}-\text{CH}(\text{R}_4)-\text{CH}_2-\text{COOH}$$

| Bio # | $R_1$ | $R_2$ | $R_3$ | $R_4$ | Y |
|---|---|---|---|---|---|
| 1002 | cyanomethyl | H | isobutyl | phenyl | CO |
| 1003 | cyclohexylmethyl | H | isobutyl | phenyl | CO |
| 1004 | 2-pyridylmethyl | H | isobutyl | phenyl | CO |
| 1005 | 3-pyridylmethyl | H | isobutyl | phenyl | CO |
| 1006 | 4-hydroxyphenylmethyl | H | isobutyl | 1,3-benzo-dioxol-5-yl | CO |
| 1007 | 4-pyridylmethyl | H | isobutyl | phenyl | CO |
| 1008 | phenyl | H | isobutyl | phenyl | CO |
| 1009 | 4-phenylphenylmethyl | H | isobutyl | phenyl | CO |
| 1010 | 4-chlorophenylmethyl | H | isobutyl | phenyl | CO |
| 1011 | 4-trifluoromethylphenylmethyl | H | isobutyl | phenyl | CO |
| 1013 | phenylmethyl | H | isobutyl | phenyl | $SO_2$ |
| 1014 | 3-Indolyl | H | isobutyl | phenyl | CO |
| 1015 | 4-benzamidophenylmethyl | H | isobutyl | phenyl | CO |
| 1016 | 4-aminophenylmethyl | H | isobutyl | phenyl | CO |
| 1017 | 1-phenylcyclopropyl | H | isobutyl | phenyl | CO |
| 1018 | 3-acetamidophenylmethyl | H | isobutyl | phenyl | CO |
| 1020 | 3-benzamidophenylmethyl | H | isobutyl | phenyl | CO |
| 1021 | 1-naphthylmethyl | H | isobutyl | phenyl | CO |
| 1022 | 2-naphthylmethyl | H | isobutyl | phenyl | CO |
| 1023 | 4-phenacetamidophenylmethyl | H | isobutyl | phenyl | CO |
| 1024 | 2-aminophenylmethyl | H | isobutyl | phenyl | CO |
| 1025 | 2-(bis(phenylsulfonyl)amino)-phenylmethyl | H | isobutyl | phenyl | CO |
| 1026 | 2-benzamidophenylmethyl | H | isobutyl | phenyl | CO |
| 1027 | 2-(benzyloxycarbonylamino)-phenylmethyl | H | isobutyl | phenyl | CO |
| 1028 | 4-(2-aminobenzamido)-phenylmethyl | H | isobutyl | phenyl | CO |
| 1029 | 4-[2-(N'-methylurea)-benzamido]-phenylmethyl | H | isobutyl | phenyl | CO |
| 1030 | 3-aminophenylmethyl | H | isobutyl | phenyl | CO |
| 1031 | 3-(benzyloxycarbonylamino)-phenylmethyl | H | isobutyl | phenyl | CO |
| 1032 | 3-(phenylsulfonamido)-phenylmethyl | H | isobutyl | phenyl | CO |
| 1036 | phenylmethyl | H | isobutyl | indan-5-yl | CO |
| 1037 | 4-(N'-phenylurea)-phenylmethyl | H | 2-thiazolyl-methyl | phenyl | CO |
| 1038 | phenylmethyl | H | propyl | phenyl | CO |
| 1039 | phenylmethyl | H | butyl | phenyl | CO |
| 1040 | phenylmethyl | H | sec-butyl | phenyl | CO |
| 1041 | t-butoxy | H | hydroxymethyl | phenyl | CO |
| 1042 | t-butoxy | H | phenylmethyl | phenyl | CO |
| 1043 | t-butoxy | H | 1,1-ethano | phenyl | CO |
| 1044 | t-butoxy | methyl | isobutyl | phenyl | CO |
| 1045 | phenylmethyl | H | hydroxymethyl | phenyl | CO |
| 1046 | phenylmethyl | H | phenylmethyl | phenyl | CO |
| 1047 | phenylmethyl | H | proline side-chain | phenyl | CO |
| 1048 | phenylmethyl | H | 1,1-ethano[1] | phenyl | CO |
| 1049 B | phenylmethyl | H | asparagine side-chain | phenyl | CO |
| 1050 | 4-(N'-phenylurea)-phenylmethyl | H | isobutyl | 1,3-benzo-dioxol-5-yl | CO |
| 1051 | 4-(N'-phenylurea)phenyl | H | isobutyl | phenyl | CO |
| 1052 | 2-[4-(N'-phenylurea)-phenyl]-ethyl | H | isobutyl | phenyl | CO |
| 1053 | 4-(N'-phenylurea)-phenylmethyl | methyl | isobutyl | phenyl | CO |
| 1054 | 3-(N'-phenylurea)-phenylmethyl | H | isobutyl | phenyl | CO |
| 1055 | 4-(N'-phenylurea)-phenylmethyl | methyl | isobutyl | 1,3-benzo-dioxol-5-yl | CO |
| 1056 | 3-methoxy-4-(N'-phenylurea)-phenylmethyl | H | isobutyl | 1,3-benzo-dioxol-5-yl | CO |
| 1057 | 3-hydroxy-4-(N'-phenylurea)-phenylmethyl | H | isobutyl | 1,3-benzo-dioxol-5-yl | CO |

TABLE 1-continued (I')

$$\text{R}_1\text{-Y-N}(\text{R}_2)\text{-CH}(\text{R}_3)\text{-C(=O)-NH-CH}(\text{R}_4)\text{-CH}_2\text{-COOH}$$

| Bio # | R₁ | R₂ | R₃ | R₄ | Y |
|---|---|---|---|---|---|
| 1058 | 3-methyl-4-(N'-phenylurea)-phenylmethyl | H | isobutyl | 1,3-benzo-dioxol-5-yl | CO |
| 1060 | 4-(N'-phenylurea)-phenylmethyl | H | isobutyl | phenyl | CO |
| 1063 | 4-(N'-phenylurea)-phenylmethyl | H | isobutyl | benzyl | CO |
| 1064 | 4-(N'-methylurea)-phenylmethyl | H | isobutyl | 1,3-benzo-dioxol-5-yl | CO |
| 1065 | 4-(N'-isopropylurea)-phenylmethyl | H | isobutyl | 1,3-benzo-dioxol-5-yl | CO |
| 1066 | 4-(N'-phenylurea)-phenylmethyl | H | isobutyl | indan-5-yl | CO |
| 1067 | 4-(N'-p-toluylurea)-phenylmethyl | H | isobutyl | 1,3-benzo-dioxol-5-yl | CO |
| 1068 | 4-(N'-cyclohexylurea)-phenylmethyl | H | isobutyl | 1,3-benzo-dioxol-5-yl | CO |
| 1069 | 4-(N'-phenylurea)-phenylmethyl | H | isobutyl | 2-methoxy phenyl | CO |
| 1070 | 4-hydroxyphenylmethyl | H | isobutyl | 2-methoxy phenyl | CO |
| 1072 | 4-(N'-phenylurea)-phenylmethyl | H | isobutyl | 3-methoxy phenyl | CO |
| 1073 | 4-(benzyloxycarbonylamino)-phenylmethyl | H | isobutyl | 1,3-benzo-dioxol-5-yl | CO |
| 1074 | 4-(phenylsulfonamido) phenyl-methyl | H | isobutyl | 1,3-benzo-dioxol-5-yl | CO |
| 1075 | 4-(benzamido)phenylmethyl | H | isobutyl | 1,3-benzo-dioxol-5-yl | CO |
| 1076 | 4-(N'-t-butylurea)-phenylmethyl | H | isobutyl | 1,3-benzo-dioxol-5-yl | CO |
| 1077 | 4-(N'-ethylurea)-phenylmethyl | H | isobutyl | 1,3-benzo-dioxol-5-yl | CO |
| 1078 | 4-(N'-(3-methoxyphenyl)-urea)-phenylmethyl | H | isobutyl | 1,3-benzo-dioxol-5-yl | CO |
| 1079 | 4-(N'-(2-methoxyphenyl)-urea)-phenylmethyl | H | isobutyl | 1,3-benzo-dioxol-5-yl | CO |
| 1080 | 4-(N'-(3-pyridyl)urea)-phenylmethyl | H | isobutyl | 1,3-benzo-dioxol-5-yl | CO |
| 1081 | phenylmethyl | H | isobutyl | phenyl | CO |
| 1082 | 3-phenylpropyl | H | isobutyl | phenyl | CO |
| 1083 | methyl | H | isobutyl | phenyl | CO |
| 1084 | 2-(4-hydroxyphenyl)ethyl | H | isobutyl | phenyl | CO |
| 1085 | benzyloxy | H | isobutyl | phenyl | CO |
| 1086 | N-phenylamino | H | isobutyl | phenyl | CO |
| 1087 | 2-(4-hydroxyphenyl)ethyl | methyl | isobutyl | phenyl | CO |
| 1088 | 4-(N'-phenylurea)-phenylmethyl | H | isobutyl | 4-methoxy phenyl | CO |
| 1089 | 4-(N'-phenylurea)-phenylmethyl | H | 2-(methylthio)-ethyl | 4-methoxy phenyl | CO |
| 1090 | 4-(N'-phenylurea)-phenylmethyl | H | isobutyl | 1,4-benzo-dioxan-6-yl | CO |
| 1091 | 4-hydroxyphenylmethyl | H | isobutyl | phenyl | CO |
| 1092 | 4-methoxyphenylmethyl | H | isobutyl | phenyl | CO |
| 1093 | 4-nitrophenylmethyl | H | isobutyl | phenyl | CO |
| 1094 | n-hexyl | H | isobutyl | phenyl | CO |
| 1096 | 2-hydroxyphenylmethyl | H | isobutyl | phenyl | CO |
| 1097 | 3-hydroxyphenylmethyl | H | isobutyl | phenyl | CO |
| 1098 | 3,4-dihydroxyphenylmethyl | H | isobutyl | phenyl | CO |
| 1099 | 2,2-diphenylmethyl | H | isobutyl | phenyl | CO |
| 1100 | 2-bromo-4-hydroxy-5-methoxyphenylmethyl | H | isobutyl | phenyl | CO |
| 1101 | 4-(benzyloxycarbonylamino)-phenylmethyl | H | isobutyl | phenyl | CO |
| 1102 | 2-(N'-phenylurea)-phenylmethyl | H | isobutyl | phenyl | CO |
| 1103 | 4-aminophenylmethyl | H | isobutyl | phenyl | CO |

TABLE 1-continued (I')

| Bio # | R₁ | R₂ | R₃ | R₄ | Y |
|---|---|---|---|---|---|
| 1104 | 4-(phenylsulfonamino)-phenyl-methyl | H | isobutyl | phenyl | CO |
| 1105 | 4-(benzamido)phenylmethyl | H | isobutyl | phenyl | CO |
| 1106 | 5-(N'-phenylurea)pentyl | H | isobutyl | phenyl | CO |
| 1107 | 5-(N'-t-butylurea)pentyl | H | isobutyl | phenyl | CO |
| 1108 | 4-nitrophenylamino | H | isobutyl | phenyl | CO |
| 1109 | 4-aminophenylamino | H | isobutyl | phenyl | CO |
| 1110 | 4-(N'-phenylurea)-phenylamino | H | isobutyl | phenyl | CO |
| 1111 | 3,5-dimethoxy-4-hydroxy-phenylmethyl | H | isobutyl | phenyl | CO |
| 1112 | 4-hydroxy-3-nitrophenyimethyl | H | isobutyl | phenyl | CO |
| 1113 | 3-nitrophenylmethyl | H | isobutyl | phenyl | CO |
| 1114 | phenylmethyl | methyl | isobutyl | phenyl | CO |
| 1115 | phenylmethyl | H | isobutyl | 4-chloro phenyl | CO |
| 1116 | phenylmethyl | H | 1-hydroxy-ethyl | phenyl | CO |
| 1117 | phenylmethyl | H | 1-methoxy-ethyl | phenyl | CO |
| 1119 | phenylmethyl | H | methyl | phenyl | CO |
| 1120 | phenylmethyl | methyl | methyl | phenyl | CO |
| 1122 | phenylmethyl | H | 4-methoxy-phenylmethyl | phenyl | CO |
| 1123 | phenylmethyl | H | 2-phenylethyl | phenyl | CO |
| 1124 | phenylmethyl | H | 4-benzyloxy-phenylmethyl | phenyl | CO |
| 1125 | phenylmethyl | H | 4-hydroxy-phenylmethyl | phenyl | CO |
| 1126 | phenylmethyl | H | benzyloxy-methyl | phenyl | CO |
| 1127 | phenylmethyl | H | benzylthio-methyl | phenyl | CO |
| 1128 | 4-(N'-phenylurea)-phenylmethyl | H | isobutyl | indan-5-yl | CO |
| 1129 | 4-(N'-phenylurea)-phenylmethyl | H | benzyl | 1,3-benzo-dioxol-5-yl | CO |
| 1130 | 4-(N'-phenylurea)-phenylmethyl | H | benzyl | phenyl | CO |
| 1131 | 4-(N'-phenylurea)-phenylmethyl | H | sec-butyl | phenyl | CO |
| 1132 | 4-(N'-phenylurea)-phenylmethyl | H | 4-(benzyloxy-carbonylamino)-butyl | phenyl | CO |
| 1133 | 4-(N'-phenylurea)-phenylmethyl | H | sec-butyl | 1,3-benzo-dioxol-5-yl | CO |
| 1134 | 4-(N'-phenylurea)-phenylmethyl | H | t-butoxy-carbonylamino-methyl | phenyl | CO |
| 1135 | 4-(N'-phenylurea)-phenylmethyl | H | 2-(methylthio)-ethyl | phenyl | CO |
| 1136 | 4-(N'-phenylurea)-phenylmethyl | H | 2-benzylthio-methyl | phenyl | CO |
| 1137 | phenylmethyl | H | isobutyl | 2-nitro phenyl | CO |
| 1138 | 4-(N'-phenylurea)-phenylmethyl | H | aminomethyl | phenyl | CO |
| 1139 | 4-(N'-phenylurea)-phenylmethyl | H | 4-amino-butyl | phenyl | CO |
| 1140 | phenylcarbonyl | H | isobutyl | phenyl | CH₂ |
| 1141 | phenylcarbonyl | phenacyl | isobutyl | phenyl | CH₂ |
| 1142 | 2,3-benzocyclobutyl | H | isobutyl | phenyl | CO |
| 1143 | 4-hydroxyphenylmethyl | H | isobutyl | benzyl | CO |
| 1144 | 4-hydroxyphenylmethyl | H | isobutyl | phenyl | CO |
| 1145 | 4-(t-butoxycarbonylamino)-phenylmethyl | H | isobutyl | phenyl | CO |
| 1146 | 4-hydroxyphenylmethyl | H | isobutyl | 3-methoxy phenyl | CO |

TABLE 1-continued (I')

$$\text{R}_1\text{-Y-N(R}_2\text{)-CH(R}_3\text{)-C(O)-NH-CH(R}_4\text{)-CH}_2\text{-COOH}$$

| Bio # | R₁ | R₂ | R₃ | R₄ | Y |
|---|---|---|---|---|---|
| 1147 | 4-acetamidophenylmethyl | H | isobutyl | phenyl | CO |
| 1148 | 4-hydroxyphenylmethyl | H | isobutyl | 3-pyridyl | CO |
| 1149 | 2-quinolinyl | H | isobutyl | phenyl | CO |
| 1150 | 2-phenylethyl | H | isobutyl | phenyl | CO |
| 1152 | 2,2-dimethylpropyl | H | isobutyl | phenyl | CO |
| 1153 | benzyloxy | H | isobutyl | 3-pyridyl | CO |
| 1154 | t-butylamino | H | isobutyl | phenyl | CO |
| 1155 | phenylmethyl | H | t-butyl | phenyl | CO |
| 1156 | methyl | H | t-butyl | phenyl | CO |
| 1157 | phenylmethyl | H | isobutyl | benzyl | CO |
| 1158 | phenylmethyl | H | isobutyl | 1,3-benzodioxol-5-yl | CO |
| 1159 | phenylmethyl | H | isobutyl | 2-methoxyphenyl | CO |
| 1160 | phenylmethyl | H | isobutyl | 3-methoxyphenyl | CO |
| 1162 | benzyloxy | H | isobutyl | methyl | CO |
| 1163 | 4-(N'-phenylurea)-phenylmethyl | H | 2-(methylthio)-ethyl | 1,3-benzodioxol-5-yl | CO |
| 1164 | phenylmethyl | H | 2-(methylthio)-ethyl | 1,3-benzodioxol-5-yl | CO |
| 1168 | 4-(N'-(3-methylphenyl)-urea)-phenylmethyl | H | isobutyl | 1,3-benzodioxol-5-yl | CO |
| 1169 | 4-(N'-benzylurea)-phenylmethyl | H | isobutyl | 1,3-benzodioxol-5-yl | CO |
| 1170 | 4-(N'-phenylurea)-phenylmethyl | H | morpholino-N-carbonylmethyl | 1,3-benzodioxol-5-yl | CO |
| 1173 | 4-hydroxyphenylmethyl | H | isobutyl | 4-methoxyphenyl | CO |
| 1174 | 4-hydroxyphenylmethyl | H | 2-(methylthio)-ethyl | 4-methoxyphenyl | CO |
| 1175 | phenylmethyl | H | 2-(methylthio)-ethyl | 4-methoxyphenyl | CO |
| 1176 | 4-(N'-phenylurea)-phenylmethyl | H | thiomorpholino-N-carbonylmethyl | 1,3-benzodioxol-5-yl | CO |
| 1177 | 4-(N'-phenylurea)-phenylmethyl | H | N,N-(methylpropargyl)amino carbonyl-methyl | 1,3-benzodioxol-5-yl | CO |
| 1178 | phenylmethyl | H | isobutyl | 4-methoxyphenyl | CO |
| 1179 | 4-(N'-(2-methylphenyl)-urea)-phenylmethyl | H | isobutyl | 1,3-benzodioxol-5-yl | CO |
| 1180 | 4-(N'-(2-thiazolyl)-urea)-phenylmethyl | H | isobutyl | 4-methoxyphenyl | CO |
| 1181 | 4-(N'-(3-chlorophenyl)-urea)-phenylmethyl | H | isobutyl | 1,3-benzodioxol-5-yl | CO |
| 1182 | 4-(N'-(4-pyridyl)urea)-phenylmethyl | H | isobutyl | 1,3-benzodioxol-5-yl | CO |
| 1185 | 4-(N'-(2-chlorophenyl)-urea)-phenylmethyl | H | isobutyl | 1,3-benzodiaxol-5-yl | CO |
| 1187 | 3-(N'-phenylurea)propyl | H | isobutyl | phenyl | CO |
| 1188 | 1-phenylcyclopropyl | H | isobutyl | 1,3-benzodioxol-5-yl | CO |
| 1189 | 1-indanyl | H | isobutyl | phenyl | CO |
| 1190 | 4-(N'-(2-methylphenyl)-urea)-phenylmethyl | H | isobutyl | 4-methoxyphenyl | CO |
| 1191 | 4-(N'-phenylurea)-phenylmethyl | H | 2-(N-morpholino)-ethyl | 1,3-benzodioxol-5-yl | CO |
| 1192 | 4-(N'-(2-methoxyphenyl)-urea)-phenylmethyl | H | isobutyl | 4-methoxyphenyl | CO |
| 1193 | 4-(N'-phenylurea)-phenylmethyl | methyl | isobutyl | 4-methoxyphenyl | CO |
| 1194 | 4-(N'-(2-pyridyl)urea)-phenylmethyl | H | isobutyl | 4-methoxyphenyl | CO |
| 1195 | 4-(N'-phenylurea)-phenylmethyl | H | isobutyl | 3,4-difluorophenyl | CO |

TABLE 1-continued (I')

| Bio # | R₁ | R₂ | R₃ | R₄ | Y |
|---|---|---|---|---|---|
| 1196 | 4-(N'-phenylurea)-phenylmethyl | H | isobutyl | 3,4-dimethoxy-phenyl | CO |
| 1197 | 4-(N'-(2-methylphenyl)-urea)-phenylmethyl | H | isobutyl | phenyl | CO |
| 1198 | 4-(morpholinocarbonylamino)-phenylmethyl | H | isobutyl | 1,3-benzodioxol-5-yl | CO |
| 1199 | 4-(N'-phenylurea)-phenylmethyl | H | 2-methyl-sulfinylethyl | 4-methoxyphenyl | CO |
| 1200 | 4-(N'-(2-ethylphenyl)urea)-phenylmethyl | H | isobutyl | 1,3-benzodioxol-5-yl | CO |
| 1201 | 4-(N'-(2-nitrophenyl)urea)-phenylmethyl | H | isobutyl | 1,3-benzodioxol-5-yl | CO |
| 1206 | 4-(N'-(2-isopropylphenyl)-urea)-phenylmethyl | H | isobutyl | 1,3-benzodioxol-5-yl | CO |
| 1207 | 4-(N'-(2-isopropylphenyl)-urea)-phenylmethyl | H | isobutyl | 4-methoxyphenyl | CO |
| 1208 | 4-(N'-(2-ethylphenyl)urea)-phenylmethyl | H | isobutyl | 4-methoxyphenyl | CO |
| 1209 | 4-(N'-(2-t-butylphenyl)-urea)-phenylmethyl | H | isobutyl | 1,3-benzodioxol-5-yl | CO |
| 1210 | 4-(N'-(2-methylphenyl)-urea)-phenylmethyl | H | isobutyl | 1,4-benzodioxan-6-yl | CO |
| 1212 | 4-(N'-(2-methylphenyl)-urea)-phenylmethyl | H | isobutyl | 3,4-dimethoxy-phenyl | CO |
| 1214 | 4-(N'-phenylurea)-phenylmethyl | H | N,N-dimethyl amino-carbonylmethyl | 1,3-benzodioxol-5-yl | CO |
| 1215 | 4-(N'-phenylurea)-phenylmethyl | H | 2-(N,N-dimethyl-amino)-ethyl | 1,3-benzodioxol-5-yl | CO |
| 1216 | 4-(N'-phenylurea)-phenylmethyl | H | 2-(morpholino-N-carbonyl)-ethyl | 1,3-benzodioxol-5-yl | CO |
| 1217 | 4-(N'-(2-methylphenyl) urea)-phenylmethyl | H | 4-(benzyloxy-carbonylamino)-butyl | 3,4-dimethoxy-phenyl | CO |
| 1218 | 4-(N'-(2-pyridyl)urea)-phenylmethyl | H | isobutyl | 3,4-dimethoxy-phenyl | CO |
| 1219 | 4-(N'-(3-pyridyl)urea)-phenylmethyl | H | isobutyl | 3,4-dimethoxy-phenyl | CO |
| 1220 | 4-(N'-(2-methyl-3-pyridyl) urea)-phenylmethyl | H | isobutyl | 4-methoxyphenyl | CO |
| 1221 | 3-methoxy-4-(N'-(2-methylphenyl)-urea)phenylmethyl | H | isobutyl | 1,3-benzodioxol-5-yl | CO |
| 1222 | 4-(N'-(2-chlorophenyl)-urea)-3-methoxyphenylmethyl | H | isobutyl | 1,3-benzodioxol-5-yl | CO |
| 1223 | 4-(phenylaminocarbonylamino-methyl)-phenyl | H | isobutyl | 1,3-benzodioxol-5-yl | CO |
| 1224 | 4-(N'-(2-methylphenyl)-urea)-phenylmethyl | H | 2-(methylthio)-ethyl | 3,4-dimethoxy-phenyl | CO |
| 1225 | 4-(N'-(2-methylphenyl)-urea)-phenylmethyl | H | 4-(benzyloxy-carbonylamino)-butyl | 1,3-benzodioxol-5-yl | CO |
| 1227 | 4-(N'-(2-methylphenyl)-urea)-phenylmethyl | H | methylthiomethyl | 1,3-benzodioxol-5-yl | CO |
| 1238 | 4-(N'-(2-methylphenyl)-urea)-phenylmethyl | H | 2-(methylthio)-ethyl | 4-methoxyphenyl | CO |
| 1245 | 4-(N'-(2-methylphenyl)-urea)-phenylmethyl | H | 2-(methyl-sulfonyl)-ethyl | 1,3-benzodioxol-5-yl | CO |
| 1246 | 4-(N'-(2-methylphenyl)-urea)-phenylmethyl | H | 3-(hyrdoxypropyl-thio)-methyl | 1,3-benzodioxol-5-yl | CO |
| 1248 | 4-(N'-(2-methylphenyl)-urea)-phenylmethyl | H | isobutyl | 4-fluorophenyl | CO |

TABLE 1-continued (I')

$$R_1-Y-N(R_2)-CH(R_3)-C(=O)-NH-CH(R_4)-CH_2-COOH$$

| Bio # | R₁ | R₂ | R₃ | R₄ | Y |
|---|---|---|---|---|---|
| 1270 | 4-(N'-(2-methylphenyl)-urea)-phenylmethyl | H | 4-acetylamino-butyl | 1,3-benzo-dioxol-5-yl | CO |
| 1282 | 4-(N'-(2-methylphenyl)-urea)-phenylmethyl | H | isobutyl | 1,3-benzo-dioxol-5-yl | CO |
| 1294 | 4-(N'-(2-methylphenyl)-urea)-phenylmethyl | H | 4-(methylsulfonyl-amino)-butyl | 1,3-benzo-dioxol-5-yl | CO |
| 1321 | 4-(N'-(2-methylphenyl)-urea)-phenylmethyl | H | isobutyl | 4-carboxyphenyl | CO |
| 1327 | 4-(1-indolecarboxylamino)-phenylmethyl | H | isobutyl | 1,3-benzo-dioxol-5-yl | CO |
| 1336 | 6-methoxy-5-(N'-(2-methylphenyl)urea)-2-pyridylmethyl | H | isobutyl | 1,3-benzo-dioxol-5-yl | CO |
| 1360 | 4-(N'-(2-methylphenyl)-urea)-phenylmethyl | H | isobutyl | 2,3-dihydro-benzofuran-5-yl | CO |
| 1380 | 4-(N'-phenyl-N''-methyl-guanidino)-phenylmethyl | H | isobutyl | 1,3-benzo-dioxol-5-yl | CO |
| 1382 | 4-(N'-(2-methylphenyl)-urea)-phenylmethyl | H | 4-(methylsulfonyl-amino)-butyl | 4-carbometh-oxy-phenyl | CO |
| 1390 | 4-(1,3-imidazol-2-ylamino)-phenylmethyl | H | isobutyl | 1,3-benzo-dioxol-5-yl | CO |
| 1396 | 4-(1,3-benzoxazol-2-ylamino)-phenylmethyl | H | isobutyl | 1,3-benzo-dioxol-5-yl | CO |
| 1400 | 4-(N'-(2-methylphenyl)-urea-phenylmethyl | H | isobutyl | phenylethyl | CO |

The most preferred compounds of formula (I) are: BIO-1006, BIO-1056, BIO-1089, BIO-1179, BIO-1194, BIO-1221, BIO-1224, BIO-1238, BIO-1245, BIO-1246, BIO-1248, BIO-1270, BIO-1282, BIO-1294, BIO-1321, BIO-1336, BIO-1382 and BIO-1400.

Compounds of this invention may be synthesized using any conventional technique. Preferably, these compounds are chemically synthesized from readily available starting materials, such as α-amino acids. Modular and convergent methods for the synthesis of these compounds are also preferred. In a convergent approach, for example, large sections of the final product are brought together in the last stages of the synthesis, rather than by incremental addition of small pieces to a growing molecular chain.

According to one embodiment, compounds of the present invention may be synthesized in the following manner. A protected chiral amine is added to an α,β-unsaturated ester to produce a protected β-amino acid ester. Upon suitable deprotection, the β-amino acid ester is coupled to an appropriate activated ester moiety. The coupled product, if suitably functionalized, may be further reacted with yet another activated ester moiety. This material can be further manipulated to give the desired compounds of the invention. At each step of the above sequence, the ester can be hydrolyzed to the corresponding acid to give another compound of the invention.

Alternatively, the activated ester moieties mentioned above can be attached together first, then the resulting compound can be attached to the β-amino acid ester portion. At this point the final manipulations and/or necessary deprotection steps can be performed.

Alternatively, under suitable conditions, the desired functionalities can be incorporated (protected or unprotected) in one of the activated ester moieties. That piece is then coupled with a β-amino acid ester or a moiety consisting of a β-amino ester previously coupled to an activated ester. The resulting product can then be subjected to any deprotection steps, if necessary, to give compounds of the invention.

Alternatively, the chiral β-amino acid esters used in the synthesis of the compounds of this invention may be synthesized by well-known techniques, such as those described in U.S. Pat. No. 5,344,957, the disclosure of which is herein incorporated by references.

The compounds of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

As used throughout this application, the term "patient" refers to mammals, including humans. And the term "cell" refers to mammalian cells, including human cells.

Once synthesized, the activities and VLA-4 specificities of the compounds according to this invention may be determined using in vitro and in vivo assays.

For example, the cell adhesion inhibitory activity of these compounds may be measured by determining the concentration of inhibitor required to block the binding of VLA-4-expressing cells to fibronectin- or CS1-coated plates. In this assay microtiter wells are coated with either fibronectin (containing the CS-1 sequence) or CS-1. If CS-1 is used, it must be conjugated to a carrier protein, such as bovine serum albumin, in order to bind to the wells. Once the wells are coated, varying concentrations of the test compound are then added together with appropriately labelled, VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound.

VLA-4-expressing cells that may be utilized in this assay include Ramos cells, Jurkat cells, A375 melanoma cells, as well as human peripheral blood lymophocytes (PBLs). The cells used in this assay may be fluorescently or radioactively labelled.

A direct binding assay may also be employed to quantitate the inhibitory activity of the compounds of this invention. In this assay, a VCAM-IgG fusion protein containing the first two immunoglobulin domains of VCAM (D1D2) attached above the hinge region of an IgG1 molecule ("VCAM 2D-IgG"), is conjugated to a marker enzyme, such as alkaline phosphatase ("AP"). The synthesis of this VCAM-IgG fusion is described in PCT publication WO 90/13300, the disclosure of which is herein incorporated by reference. The conjugation of that fusion to a marker enzyme is achieved by cross-linking methods well-known in the art.

The VCAM-IgG enzyme conjugate is then placed in the wells of a multi-well filtration plate, such as that contained in the Millipore Multiscreen Assay System (Millipore Corp., Bedford, Mass.). Varying concentrations of the test inhibitory compound are then added to the wells followed by addition of VLA-4-expressing cells. The cells, compound and VCAM-IgG enzyme conjugate are mixed together and allowed to incubate at room temperature.

Following incubation, the wells are vacuum drained, leaving behind the cells and any bound VCAM. Quantitation of bound VCAM is determined by adding an appropriate calorimetric substrate for the enzyme conjugated to VCAM-IgG and determining the amount of reaction product. Decreased reaction product indicates increased binding inhibitory activity.

In order to assess the VLA-4 inhibitory specificity of the compounds of this invention, assays for other major groups of integrins, i.e., $\beta 2$ and $\beta 3$, as well as other $\beta 1$ integrins, such as VLA-5, VLA-6 and $\alpha 4\beta 7$ are performed. These assays may be similar to the adhesion inhibition and direct binding assays described above, substituting the appropriate integrin-expressing cell and corresponding ligand. For example, polymorphonuclear cells (PMNs) express $\beta 2$ integrins on their surface and bind to ICAM. $\beta 3$ integrins are involved in platelet aggregation and inhibition may be measured in a standard platelet aggregation assay. VLA-5 binds specifically to Arg-Gly-Asp sequences, while VLA-6 binds to laminin. $\alpha 4\beta 7$ is a recently discovered homologue of VLA-4, which also binds fibronectin and VCAM. Specificity with respect to $\alpha 4\beta 7$ is determined in a binding assay that utilizes the above-described VCAM-IgG-enzyme marker conjugate and a cell line that expresses $\alpha 4\beta 7$, but not VLA-4, such as RPMI-8866 cells.

Once VLA-4-specific inhibitors are identified, they may be further characterized in in vivo assays. One such assay tests the inhibition of contact hypersensitivity in an animal, such as described by P. L. Chisholm et al., "Monoclonal-Antibodies to the Integrin $\alpha$-4 Subunit Inhibit the Murine Contact Hypersensitivity Response", *Eur. J. Immunol.*, 23, pp. 682–688 (1993) and in "Current Protocols in Immunology", J. E. Coligan, et al., Eds., John Wiley & Sons, New York, 1, pp. 4.2.1–4.2.5 (1991), the disclosures of which is herein incorporated by reference. In this assay, the skin of the animal is sensitized by exposure to an irritant, such as dinitrofluorobenzene, followed by light physical irritation, such as scratching the skin lightly with a sharp edge. Following a recovery period, the animals are re-sensitized following the same procedure. Several days after sensitization, one ear of the animal is exposed to the chemical irritant, while the other ear is treated with a non-irritant control solution. Shortly after treating the ears, the animals are given various doses of the VLA-4 inhibitor by subcutaneous injection. In vivo inhibition of cell adhesion-associated inflammation is assessed by measuring the ear swelling response of the animal in the treated versus untreated ear. Swelling is measured using calipers or other suitable instrument to measure ear thickness. In this manner, one may identify those inhibitors of this invention which are best suited for inhibiting inflammation.

Another in vivo assay that may be employed to test the inhibitors of this invention is the sheep asthma assay. This assay is performed essentially as described in W. M. Abraham et al., "$\alpha$-Integrins Mediate Antigen-induced Late Bronchial Responses and Prolonged Airway Hyperresponsiveness in Sheep", *J. Clin. Invest.*, 93, pp. 776–87 (1994), the disclosure of which is herein incorporated by reference. This assay measures inhibition of *Ascaris* antigen-induced late phase airway responses and airway hyperresponsiveness in asthmatic sheep.

The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of the present invention may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques Known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is coadministered.

The dosage and dose rate of the compounds of this invention effective to prevent, suppress or inhibit cell adhesion will depend on a variety of factors, such as the nature of the inhibitor, the size of the patient, the goal of the treatment, the nature of the pathology to be treated, the specific pharmaceutical composition used, and the judgment of the treating physician. Dosage levels of between about 0.001 and about 100 mg/kg body weight per day, preferably between about 0.1 and about 10 mg/kg body weight per day of the active ingredient compound are useful.

According to another embodiment compositions containing a compound of this invention may also comprise an additional agent selected from the group consisting of corticosteroids, bronchodilators, antiasthmatics (mast cell stabilizers), antiinflammatories, antirheumatics, immunosuppressants, antimetabolites, immunonodulators, antipsoriatics and antidiabetics. Specific compounds within each of these classes may be selected from any of those listed under the appropriate group headings in "Comprehensive Medicinal Chemistry", Pergamon Press, Oxford, England, pp. 970–986 (1990), the disclosure of which is herein incorporated by reference. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); and interferons (immunomodulators).

According to other embodiments, the invention provides methods for preventing, inhibiting or suppressing cell adhesion-associated inflammation and cell adhesion-associated immune or autoimmune responses. VLA4-associated cell adhesion plays a central role in a variety of inflammation, immune and autoimmune diseases. Thus, inhibition of cell adhesion by the compounds of this invention may be utilized in methods of treating or preventing inflammatory, immune and autoimmune diseases. Preferably the diseases to be treated with the methods of this invention are selected from asthma, arthritis, psoriasis, transplantation rejection, multiple sclerosis, diabetes and inflammatory bowel disease.

These methods may employ the compounds of this invention in a monotherapy or in combination with an anti-inflammatory or immunosuppressive agent. Such combination therapies include administration of the agents in a single dosage form or in multiple dosage forms administered at the same time or at different times.

In order that this invention may be more fully understood, the following examples are set forth. These examples are for the purpose of illustration only and are not to be construed as limiting the scope of the invention in any way.

GENERAL SYNTHESIS PROCEDURES

We utilized the following procedures in the synthesis of many compounds of this invention. These procedures will be referred to by the indicated letter in the subsequent examples of the synthesis of specific compounds.

Procedure A—Synthesis of Cinnamate Esters

Method A: To a cinnamic acid or substituted cinnamic acid (1.0 mmol) in $CH_2CH_2$ (10 ml) was added $(COCl)_2$ (1.5 mmol) slowly. The reaction mixture was stirred at r.t. for 4 h and the solvent was removed in vacuo to afford the acid chloride. Methanol or t-butyl alcohol (5 ml) was added to quantitatively provide the methyl or t-butyl ester after removal of the solvents.

Method B: To an appropriate aldehyde (1.0 mmol) in THF (10 ml) was added t-butoxycarbonyl methylene triphenylphosphorane (1.0 mmol, Aldrich) and the resulting mixture was stirred at room temperature for 16 h. The reaction mixture was diluted with petroleum ether (10 ml) and was filtered through a pad of celite. The filtrate was collected and concentrated in vacuo to afford the desired product.

E-1:

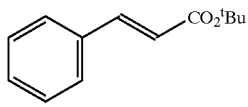

Method A; Yield: 95%; ($CDCl_3$, 300 MHz, ppm): 7.57 (d, 1H, J=16 Hz), 7.47 (m, 2H), 7.34 (m, 3H), 6.35 (d, 1H, J=16 Hz), 1.52 (s, 9H);

E-2:

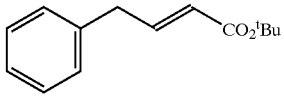

Method B; Yield: 90%; ($CDCl_{31}$ 300 MHz, ppm): 7.48 (d, 1H), 7.28–7.18 (m, 5H), 5.69 (d, 2H), 3.44 (d, 2H), 1.42 (s, 9H);

E-3:

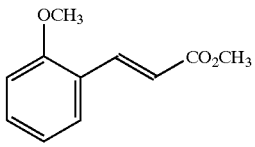

Method A; Yield: 94%; ($CDCl_3$, 300 MHz, ppm): 7.95 (d, 1H, J=16 Hz), 7.49 (d, 1H), 7.42 (t, 1H), 6.94 (dd, 2H), 6.51 (d, 2H), J=16 Hz), 3.86 (s, 3H), 3.76 (s, 3H);

E-4:

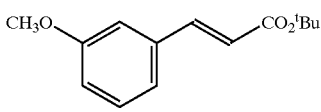

Method A; Yield: 92%; ($CDCl_3$, 300 MHz, ppm): 7.52 (d, 1H, J=15.9 Hz), 7.28 (t, 1H), 7.09 (d, 1H), 7.02 (br, s, 1H), 6.89 (d, 1H), 6.34 (d, 1H, J=15.9 Hz) 3.82 (s, 3H), 1.54 (s, 9H);

E-5:

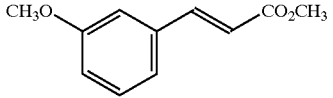

Method A: Yield: 98%; ($CDCl_3$, 300 MHz, ppm): 7.64 (d, 1H, J=16 Hz), 7.29 (t, 1H), 7.10 (d, 1H), 7.06 (br, s, 1H), 6.94 (d, 1H, J=16 Hz), 3.82 (s, 3H), 3.80 (s, 3H);

E-6:

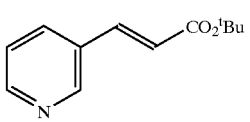

Method B; Yield: 88%; (CDCl$_3$, 300 MHz, ppm): 8.62 (br,s, 1H), 8.51 (m, 1H), 7.72 (d, 1H), 7.48 (d, 1H, J=15.9 Hz), 7.22 (m, 1H), 6.36 (d, 1H, J=15.9 Hz), 1.49 (s, 9H);

E-7:

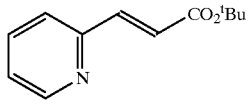

Method B; Yield: 90%; (CDCl$_3$, 300 MHz, ppm): 8.60 (br, s, 1H), 7.66 (t, 1H), 7.55 (d, 1H, J=15.9 Hz), 7.36 (d, 1H), 7.21 (m, 1H), 6.78 (d, 1H, J=15.9 Hz), 1.52 (s, 9H);

E-8:

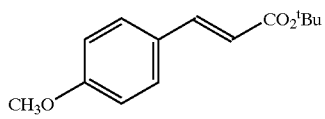

Method A; Yield: 91%; (CDCl$_3$, 300 MHz, ppm): 7.52 (d, 1H, J=15.9 Hz), 7.44 (d, 1H, J=8.0 Hz), 6.85 (d, 1H, J=8.0 Hz), 6.21 (d, 1H, J=15.9 Hz), 3.81 (s, 3H), 1.52 (s, 9H);

E-9:

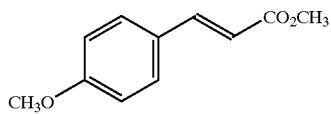

Method A; Yield: 90%; (CDCl$_3$, 300 MHz, ppm): 7.61 (d, 1H, J=16 Hz), 7.42 (d, 2H, J=7.9 Hz), 6.86 (d, 1H, J= 7.9 Hz), 6.28 (d, 1H, J=16 Hz), 3.78 (s, 3H), 3.74 (s, 3H);

E-10:

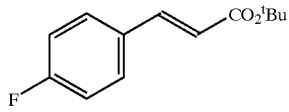

Method B; Yield: 91%; (CDCl$_3$, 300 MHz, ppm): 7.56 (d, 1H, J=16 Hz), 7.46 (t, 2H), 7.02 (t, 2H), 6.26 (d, 2H, J=16 Hz), 1.54 (s, 9H);

E-11:

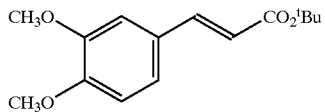

Method A; Yield: 89%; (CDCl, 300 MHz, ppm): 7.47 (d, 1H, J=15.9 Hz), 7.01 (d, 1H, J=8.3 Hz), 6.98 (br, s, 1H), 6.78 (d, 1H, J=8.3 Hz), 3.84 (s, 6H), 1.48 (s, 9H);

E-12:

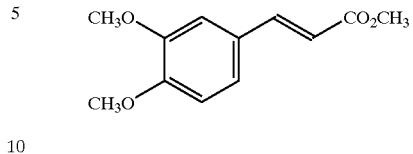

Method A; Yield: 91%; (CDCl$_3$, 300 MHz, ppm): 7.61 (d, 1H, J=15.9 Hz, 7.07 (d, 1H, J=8.3 Hz), 7.02 (br, s, 1H), 6.83 (d, 1H, J=8.3 Hz), 6.28 (d, 1H, J=15.9 Hz), 3.88 (s, 3H), 3.76 (s, 3H);

E-13:

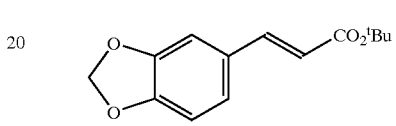

Method A; Yield: 92%; (CDCl$_3$, 300 MHz, ppm):7.46 (d, 1H, J=16.1 Hz), 6.99 (s, 1H), 6.97 (d, 1H), 6.76 (d, 1H), 6.18 (d, 1H, J=16.1 Hz), 5.96 (s, 2H), 1.50 (s, 9H);

E-14:

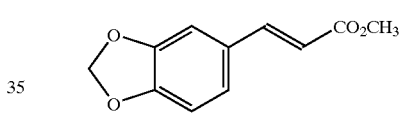

Method A; Yield: 88%; (CDCl$_3$, 300 MHz, ppm): 7.55 (d, 1H, J=15.9 Hz), 6.98–6.75 (m, 2H), 6.22 (d, 1H, J=15.9 Hz), 5.96 (s, 2H), 3.75 (s, 3H);

E-15:

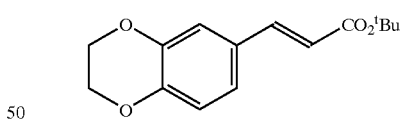

Method B; Yield: 89%; (CDCl$_3$, 300 MHz, ppm): 7.45 (d, 1H, J=15.8 Hz), 6.99 (s, 1H), 6.98 (d, 1H), 6.80 (d, 1H), 6.18 (d, 1H, J=15.8 Hz), 4.21 (br,s, 4H), 1.49 s, 9H);

E-16:

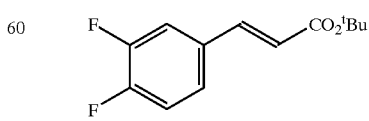

Method B; Yield: 88%.

E-17:

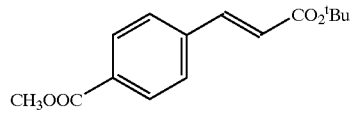

Method B; Yield: 93%; $^1$HNMR(CDCl$_3$): δ 8.00 (2H, d, J=5.5 Hz), 7.53 (2H, d. J=5.5 Hz), 7.58 (1H, d, J=10.7 Hz), 6.42 (1H, d, J=10.7 Hz), 3.90 (3H, S), 1.51 (9H, S).

Procedure B—Synthesis of β-Amino Acids

A 2 L round bottom flask, equipped with a magnetic stir bar, was charged with 1000 mL of MeOH and the flask tared with its contents. Anhydrous HCl (11 g, 0.29 mol) was bubbled in from a cylinder. To this solution was added a cinnamic acid (0.29 mol) neat in one portion. The resulting mixture was heated at reflux until the reaction was judged complete by TLC analysis. The reaction was cooled to RT, then refrigerated overnight. The crystalline product was collected by suction filtration on a medium frit and the cake washed with cold MeOH. The solid was dried on the filter to give a white or nearly white product.

Precursor to β-3: Yield: 94%; TLC (3:1 hexane/EtOAc; UV): R$_f$=0.48; mp=134–136° C.; $^1$H NMR (CDCl$_3$, 300 MHz): 7.58 (d, 1H, J=15.9 Hz), 7.00–6.97 (m, 3H), 6.79 (d, 1H, J=7.9 Hz), 6.24 (d, 1H, J=15.9 Hz), 5.98 (s, 2H), 3.77 (s, 3H); MS (FAB): 206.

Precursor to β-5: Yield: 84%; TLC (3:1 hexane/EtOAc; UV): R$_f$=0.48; mp=89–91° C.; $^1$H NMR (CDCl$_3$, 300 MHz) 7.63 (d, 1H, J=15.9 Hz), 7.46 (d, 2H, J=8.7 Hz), 6.89 (d, 2H, J=8.7 Hz), 6.29 (d, 1H, J=15.9 Hz), 3.82 (s, 3H), 3.77 (s, 3H); MS (FAB): 192.

Michael Addition of (R)-(+)-N-benzyl-1-phenylethylamine to methyl 4-methoxy-cinnamate A 1 L 3-neck round bottom flask, equipped with a stopper, thermometer, and 250 mL addition funnel with an Ar inlet was charged with (R)-(+)-N-benzyl-1-phenylethylamine hydrochloride (0.132 mol, 32.6 g, 1.1 eq based on cinnamate) and the apparatus flushed with Ar 30 min. The salt was suspended in dry THF (200 mL) and the mixture cooled to an internal temperature of −70° C. with a dry ice/acetone bath. To the suspension was added n-BuLi (2.5 M in hexanes, 0.257 mol, 103 mL, 1.95 eq based on amine hydrochloride) from the addition funnel at such a rate that the internal temperature did not exceed −65° C. The addition required 90 min. After completing the addition, the reaction was stirred at −70° C. for 1 hr. A solution of methyl 4-methoxycinnamate (0.120 mol, 23 g, 1 eq) in THF (125 mL) was added from the addition funnel over 90 min at such a rate that the internal temperature did not exceed −65° C. After completing the addition, the reaction was stirred at −70° C. 2 hrs. TLC analysis indicated complete reaction. The reaction was quenched cold by the addition of 5% citric acid (250 mL) and stirred overnight at RT. In a 2 L separatory funnel, the layers were separated and the organic washed with 5% citric acid (1×125 mL). The combined aqueous were extracted with EtOAc (1×200 mL). The combined organics were then washed with 5% NaHCO$_3$ (1×150 mL) and brine (1×150 mL) and dried (MgSO$_4$). Filtration and evaporation to constant weight provided crude product (50.04 g, 103% of theory) as a viscous oil which solidified on standing. Pure material was obtained by triturating and stirring crude product with heptane (1.5–2 mL/g, 75–100 mL total volume) at RT overnight. The solids were collected by suction filtration on a medium frit and the cake washed by flooding with cold heptane (2×50 mL). The solids were dried on the filter to give pure product (28.93 g, 60% yield) as a white powder. TLC (4:1 hexane/EtOAc): R$_f$=0.50 (12, UV); mp=87–88° C.; $^1$H NMR (CDCl$_3$, 300 MHz): 1.20 (d, 3H, J=6.9 Hz), 2.51 (dd, 1H, J=9.4, 14.8 Hz), 2.66 (dd, 1H, J=5.7, 14.8 Hz), 3.45 (s, 3H), 3.67 (ABq, 2H, J=14.7 Hz), 3.79 (s, 3H), 3.98 (q, 1H, J=6.8 Hz), 4.37 (dd, 1H, J=5.7, 9.3 Hz), 6.86 (d, 2H, J=8.6 Hz), 7.16–7.33 (m, 10H), 7.40 (d, 2H, J=7.3 Hz); MS (FAB): 404

Hydrogenolysis of Benzyl Groups

The above adduct (0.071 mol, 28 g) was suspended in MeOH (300 mL) and treated with formic acid (96%, 0.179 mol, 8.25 g, 6.8 mL, 2.5 eq) neat in one portion with stirring. To this suspension was added Degussa type E101 NE/W 10% Pd/C (50% wet, 0.00179 mol, 3.81 g, 0.025 eq) in one portion. The resulting mixture was heated at reflux for 1–2 hr until judged complete by TLC analysis. The mixture was cooled to RT, then filtered on a pad of Celite, washing the flask and pad with MeOH (150 mL). The combined filtrates were evaporated to give crude product (15.42 g, 102% of theory) as an oil. The crude product was dissolved in i-PrOH (250 mL) and heated to a gentle reflux. D-tartaric acid (0.071 mol, 10.76 g, 1 eq) was added as a solid in one portion. Heating was continued for 15 min, during which time the salt precipitated as a fine white solid. The mixture was cooled to RT, then refrigerated overnight. The crystalline salt was collected by suction filtration on a medium frit, washing with cold i-PrOH (50–75 mL), and dried on the filter to give product (23 g, 79%). The above salt was converted to the free base by dissolving in a minimum volume of H$_2$O (125 mL) and treating the solution with solid NaHCO$_3$ until the aqueous was saturated. This was extracted with EtOAc (3×100 mL). The combined organics were washed with brine (1×100 mL) and dried (MgSO$_4$). Filtration and evaporation provided pure product (11.75 g, 78%) as a nearly colorless oil which solidified on cooling. TLC (9:1 CHCl$_3$/MeOH): R$_f$=0.30 (2, UV); HPLC (reverse phase; MeCN/H$_2$O/TFA gradient: 96% pure, R$_t$=17.9 min; $^1$H NMR (CDCl$_3$, 300 MHz): 1.87 (br s, 2H), 2.62 (d, 2H, J=6.9 Hz), 3.64 (s, 3H), 2.76 (s, 3H), 4.35 (t, 1H, J=6.9 Hz), 6.84 (d, 2H, J=8.6 Hz), 7.25 (d, 2H, J=8.6 Hz); MS (FAB): 210.

S-1:

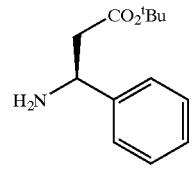

S-2:

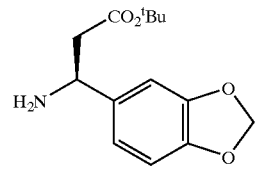

¹H NMR (CDCl₃, 300 MHz, ppm) 6.81 (d, 1H, J=1.6 Hz), 6.72 (d, 1H, J=7.9 Hz), 6.66 (d, 1H, J=7.9 Hz), 5.85 (s, 2H), 4.22 (1H, dd, J=7.5 Hz and 7.3 Hz), 2.47 (2H, dd, J=7.5 Hz and 5.6 Hz), 2.21 (s, 2H), 1.35 (9H, s).

S-3:

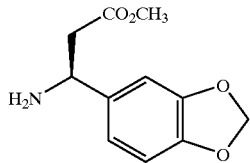

¹H NMR (CDCl₃, 300 MHz, ppm) 6.82 (d, 1H, J=1.6 Hz), 6.76 (d, 1H, J=7.9 Hz), 6.73 (d, 1H, J=7.9 Hz), 5.89 (s, 2H), 4.29 (1H, dd, J=6.9 Hz and 6.8 Hz), 3.63 (3H, s), 2.57 (d, 2H, J=6.9 Hz), 1.75 (s, 2H);

S-4:

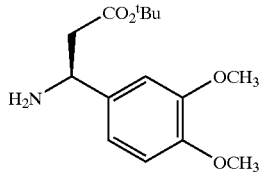

¹H NMR (CDCl₃, 300 MHz, ppm) 6.79–6.78 (m, 3H), 4.32 (t, 1H, J=6.7 Hz), 3.75 (s, 3H), 3.72 (s, 3H), 2.52 (d, 2H, J=6.8 Hz), 1.82 (br, 2H), 1.42 (s, 9H);

S-5:

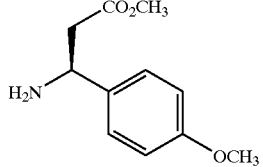

¹H NMR (CDCl₃, 300 MHz, ppm) 7.20 (d, J=8.6 Hz), 6.80 (d, 2H, J=8.6 Hz), 4.30 (t, 1H, 6.8 Hz), 3.71 (s, 3H), 3.60 (s, 3H), 2.57 (d, 2H, J=6.8 Hz), 1.91 (s, 2H);

S-6:

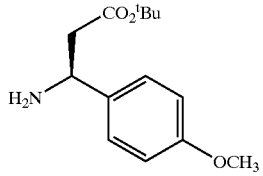

¹H NMR (CDCl₃, 300 MHz, ppm) 7.24 (d, J=8.4 Hz), 6.82 (d, 2H, J=8.4 Hz), 4.26 (t, 1H, 6.8 Hz), 3.66 (s, 3H), 2.47 (d, 2H, J=6.6 Hz), 1.41 (s, 9H);

S-7:

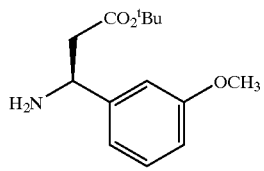

¹H NMR (CDCl₃, 300 MHz, ppm) 7.21 (dd, 1H, J=8.2 Hz and 8.1 Hz), 6.95–6.93 (m, 2H), 6.78 (d, 1H, 6.8 Hz), 4.34 (t, 1H, J=6.7 Hz), 3.79 (s, 3H), 2.54 (d, 2H, J=6.9 Hz), 1.74 (s, 2H), 1.40 (s, 9H);

S-8:

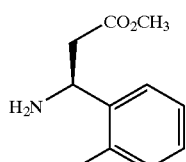

¹H NMR (CDCl₃, 300 MHz, ppm): 7.34–7.08 (m, 2H), 6.82–6.68 (m, 2H), 4.45 (m, 1H), 3.65 (s, 3H), 3.49 (s, 3H), 2.58 (d, 2H), 1.68 (br s, 2H).

S-9:

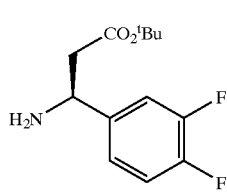

¹H NMR (CDCl₃, 300 MHz, ppm) 7.28–7.25 (m, 2H), 7.01 (d, 1H), 4.31 (t, 1H), 2.50 (d, 2H), 2.01 (br, 2H), 1.41 (s, 9H);

S-10:

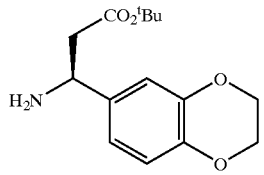

¹H NMR (CDCl₃, 300 MHz, ppm) 6.84 (s, 1H), 6.79–6.76 (m, 1H), 4.24–4.19 (m, 1H), 4.19 (s, 4H), 2.50 (d, 2H), 1.63 (br, 2H), 1.41 (s, 9H);

S-11:

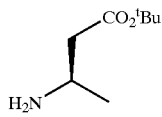

¹H NMR (CDCl₃, 300 MHz, ppm) 3.34–3.05 (m, 1H), 2.65–2.58 (m, 2H), 1.65 (d, 2H) 1.45 (fs, 9H);

S-12:

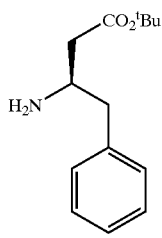

¹H NMR (CDCl₃, 300 MHz, ppm) 7.34–7.28 (m, 3H), 7.26–7.15 (m, 3H), 3.42–3.15 (m, 1H), 2.71 (dd, 1H, J=5.5 Hz and 13.3 Hz), 2.54 (dd, 1H, J=8.1 Hz and 13.3 Hz), 2.36 (dd, 1H, J=4.2 Hz and 15.7 Hz), 2.20 (dd, J=8.6 and 15.7 Hz), 1.42 (s, 9H).

To prepare β-13 amino acid

S-13:

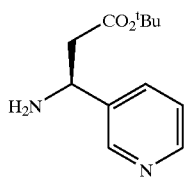

1M TMSCl in CH₂Cl₂ (33 ml, 33 mmol) was added to a mixture of (R)-α-methylbenzylamine (3.4 g, 28 mmol) and Et₃N (4 g, 40 mmol) in THF (10 ml) was added and the mixture was allowed to stir for 1 h at room temperature. After the solid was removed by filtration, the solution was concentrated to afford a liquid. This silylamine (2.4 g, 12.5 mmol) was dissolved in THF (35 ml) and was cooled to −78° C. To this cooled solution was added n-BuLi (7.8 ml of 1.6 M solution in hexanes, 12.5 mmol) slowly. After stirring for 0.5 h at the temperature, to the reaction mixture was added a solution of t-butyl trans-3-(3-pyridyl)acrylate (2.56 g, 12.4 mmol) in THF (10 ml). The stirring was continued for another ½ h and the mixture was quenched with sat. NH₄Cl (20 ml) and was allowed to warm up to room temperature and extracted with ether. The combined ether layers were dried (K₂CO₃) and concentrated to afford an oil. This oil (500 mg) was dissolved in ethanol (1.5 ml), t-butanol (15 ml), ammonium formate (1.5 g) and 10% Pd/C (1.2 g) were added. The resulting mixture was heated to reflux for 3 h followed by acid and base workup to afford the desired amine β-13 (300 mg). FAB-MS=223.

S-14:

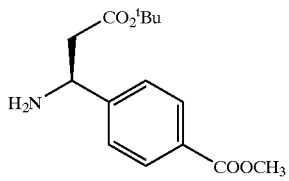

¹HNMR(CDCl₃): δ 7.97 (2H, d, J=5.4 Hz), 7.41 (2H, d, J=5.4 Hz), 4.40 (1H, t, J=4.5 Hz), 3.88 (3H,S), 2.55 (2H, d, J=4.5 Hz), 1.71 (2H, br), 1.39 (9H, S).

General Procedure for Synthesis of M-1, M-2 and M-3

To a solution of the commercially available amino acid (1.5 mmoles) in CH₂Cl₂ (4 ml) and MeOH (1 ml) cooled to 0° C., was added thionyl chloride (0.125 ml, 1.65 mmol). The reaction was warmed to 40° C. for 2 h, and concentrated to dryness in vacuo to afford the desired amino ester HCl salt.

M-1:

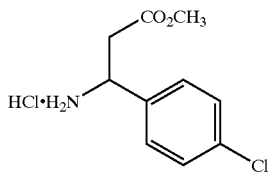

89% yield; ¹HNMR (DMSO-d⁶, 300 MHz, ppm): 9.00–8.75 (3H, bm), 7.71 (2H, d, J=7.3 Hz), 7.58 (2H, d, J=7.3 Hz) 4.71 (1H, bs), 3.64 (3H,s), 3.40–3.06 (2H, m);

M-2:

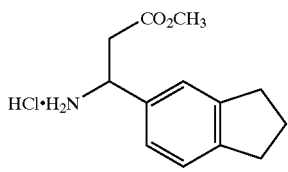

85% yield as a tan solid. ¹HNMR (CDCl₃, 300 MHz, ppm) 7.55–7.05 (6H, bm), 3.66 (3H, s), 3.65–3.45 (2H, bm), 3.10–2.77 (5H, bm), 2.17–1.95 (2H, bm);

M-3:

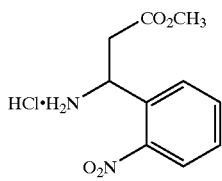

84% yield as a pale tan solid; ¹HNMR (CDCl₃, 300 MHz, ppm): 8.1–7.8 (4H, bm), 7.65–7.45 (3H, bm), 5.45 (1H, br), 3.80–3.30 (2H, bm), 3.55 (3H, s).

Procedure C—Synthesis of Coupled Amino Acids

To a solution of ethyl 3-amino-3-phenyl-1-propanoate (or other β-amino acid ester prepared by Procedure B) (0.50 g, 5.25 mmol) in CH$_2$Cl$_2$ (5 ml) was added BocLeuOSu (1.5 g, 4.67 mmol) (CbzLeuOSu is used for the Cbz protected analog) with cooling and Et$_3$N (5 drops). The mixture was stirred at room temperature for 1 h. The reaction mixture was diluted with CH$_2$Cl$_2$ (10 ml) and washed with 5% citric acid (5 ml×2), 5% NaHCO$_3$ (5 ml) and sat. NaCl (5 ml). The organic layer was dried (Na$_2$SO$_4$) and concentrated to afford 1.26 g (66%) as a white solid.

Procedure D—Synthesis of Deprotected Amino Acids

To a stirred solution of the product of Procedure C (a Boc-Leu-β-amino acid ester) (41.5 mg, 0.102 mmol) at 0–5° C. in 2 mL of CH$_2$Cl$_2$ was added 4 mL of TFA. The mixture was allowed to come to room temperature with continued stirring for 1 hour. The reaction was concentrated in vacuo; redissolved in CH$_2$Cl$_2$, concentrated two more times and placed under high vacuum to remove final traces of TFA. HPLC showed complete conversion to two new peaks of shorter retention time. The residue can taken up in DMF and TEA added with stirring until basic to litmus in preparation for further reaction. A Cbz group is removed using the following method:

The product from Procedure C (where t-butyl 3-amino-3-phenyl-1-propanoate and CbzLeuOSu were used) (110 mg, 0.23 mmol) in MeOH with a catalytic amount of 10% palladium on charcoal was stirred overnight under hydrogen at 40 psi. The reaction was filtered through Celite® and concentrated in vacuo yielding the free base Leu-β-amino acid ester (87 mg, quantitative) as a clear oil. $^1$H NMR: (CDCl$_3$, 300 MHz, ppm), 7.30 (m, 5H), 5.33 (dd, 1H, J=6, 8.82 Hz), 4.00 (m, 1H) 2.77 (dd , 1H J=9, 15 Hz), 2.90 (dd, 1H, J=6, 15 Hz), 1.69 (m, 2H), 1.45 (m, 1H), 1.29 (s, 9H), 0.90 (d, 6H, J=6 Hz).

EXAMPLE 1

Synthesis of BIO-1002

A. A stirred solution of cyanoacetic acid (13 mg, 0.15 mmol), EDC (30 mg, 0.16 mmol), and HOBt (30 mg, 0.20 mmol) in DMF (0.5 mL) was treated with a solution of the amine prepared in Procedure D (52 mg, 0.105 mmol) and diisopropylethylamine (0.30 mL, 1.7 mmol) in DMF (1.0 mL) at room temperature. After the solution was stirred for over 18 h, the reaction was partitioned in ethyl acetate (15 mL) and 60% sat. NaHCO$_3$ (10 mL). The organic phase was washed with 60% sat. aq. NaHCO$_3$ (2×10 mL), H$_2$O (5 mL), 5% citric acid (3×10 mL), H$_2$O (5 mL), and sat. aq. NaCl (10 mL). The organic phase was dried (MgSO$_4$) and concentrated in vacuo to afford BIO1002-OEt (27 mg, 69%) as a foam: $^1$H NMR (CDCl$_3$, 300 MHz, ppm) 7.58 (d, 1H), 7.45 (d, 1H), 7.40–7.20 (m, 5H), 5.28 (m, 1H), 4.46 (m, 1H), 4.05 (m, 2H), 3.23 (m, 2H), 2.79 (m, 2H), 1.78–1.53 (m, 3H), 1.23 (m, 3H), 0.90 (m, 6H).

B. A stirred solution of BIO1002-OEt (27 mg, 0.072 mmol) in methanol (3 mL) was treated with aq. LiOH (1.0 M, 0.25 mL, 0.25 mmol) at room temperature for 22 h. The reaction was acidified with trifluoroacetic acid then concentrated in vacuo. The crude products were purified by HPLC to give BIO-1002A (2.5 mg, 10%) and BIO-1002B (4.4 mg, 18%) as white solids:

BIO1002A: $^1$H NMR (CDCl$_3$, 300 MHz, ppm) 8.08 (d, 1H), 7.87 (d, 1H), 7.30–7.16 (m, 5H), 5.25 (m, 1H), 4.37 (m, 1H), 3.36 (s, 2H), 2.75 (m, 2H), 1.70–1.45 (m, 3H), 0.90 (m, 6H); HPLC (Gradient A), 16.7 min; MS, m/z 346.

BIO1002B: $^1$H NMR (CDCl$_3$, 300 MHz, ppm) 8.00–7.70 (m, 2H), 7.40–7.20 (m, 5H), 5.28 (m, 1H), 4.39 (m, 1H), 3.45 (s, 2H), 2.78 (m, 2H), 1.65–1.40 (m, 3H), 0.90 (m, 6H); HPLC (Gradient A), 20.6 min; MS, m/z 346.

EXAMPLE 2

Synthesis of BIO-1003

A. The procedure as described Example 1A was performed utilizing cyclohexylacetic acid (22 mg, 0.15 mmol), EDC (30 mg, 0.16 mmol), and HOBt (30 mg, 0.20 mmol), amine from Procedure D (52 mg, 0.105 mmol) and diisopropylethylamine (0.30 mL, 1.7 mmol) in DMF (1.0 mL) to afford BIO1003-OEt (32 mg, 71%) as a foam: $^1$H NMR (CDCl$_3$, 300 MHz, ppm) 7.42–7.18 (m, 6H), 6.08 (m, 1H), 5.36 (m, 1H), 4.50 (m, 1H), 4.05 (m, 2H), 2.81 (m, 2H), 2.11–0.80 (m, 25H).

B. The procedure as described in Example 1B was performed utilizing BIO1003-OEt (32 mg, 0.074 mmol) and aq. LiOH (1.0 M, 0.25 mL, 0.25 mmol) in MeOH (3.0 mL) to give BIO-1003A (3.5 mg, 11%) and BIO-1003B (5.3 mg, 18%) as white solids:

BIO-1003A: $^1$H NMR (CDCl$_3$, 300 MHz, ppm) 7.35–7.16 (m, 5H), 5.23 (m, 1H), 4.38 (m, 1H), 2.28 (d, 2H), 2.03 (m, 2H), 1.75–0.80 (m, 22H); HPLC (Gradient A), 34.1 min and 35.3 min (4:1); MS, m/z 403.

BIO-1003B: $^1$H NMR (CDCl$_3$, 300 MHz, ppm) 7.35–7.16 (m, 5H), 5.23 (m, 1H), 4.38 (m, 1H), 2.28 (m, 2H), 2.03 (m, 2H), 1.75–0.80 (m, 22H); HPLC (Gradient A), 34.1 min and 35.3 min (1:10); MS, m/z 403.

EXAMPLE 3

Synthesis of BIO-1014

A. Methyl 3-amino-3-phenyl-1-propanoate was coupled with BocLeuOSu by the method described in Procedure C. This material was subjected to the conditions used in Procedure D1 to give the desired TFA-amine salt.

B. The procedure as described in Example 1A was performed utilizing indole-3-carboxylic acid (19 mg, 0.12 mmol), EDC (26 mg, 0.14 mmol), HOBt (26 mg, 0.17 mmol), amine from Example 3A (44 mg, 0.11 mmol) and diisopropylethylamine (0.10 mL, 0.56 mmol) in CH$_2$Cl$_2$ (5.0 mL) to afford BIO1014-OMe (25 mg, 52%) as a foam.

C. The same procedure as described in Example 1B was performed utilizing BIO1014-OMe (25 mg, 0.057 mmol) and aq. LiOH (1.0 M, 0.115 mL, 0.115 mmol) in MeOH (5 mL) to give BIO-1014A (5.1 mg, 21%) and BIO-1014B (4.7 mg, 20%) as white solids:

BIO-1014A: $^1$H NMR (CDCl$_3$, 300 MHz, ppm) 8.52 (d, 1H), 8.13 (d, 1H), 8.10 (d, 1H), 7.81 (d, 1H), 7.46–7.03 (m, 9H), 5.20 (m, 1H), 4.58 (m, 1H), 2.69 (m, 2H), 1.75–1.45 (m, 3H), 0.90 (m, 6H); HPLC (Gradient A), 28.1 min; MS, m/z 422.

BIO-1014B: $^1$H NMR (CDCl$_3$, 300 MHz, ppm) 8.55 (d, 1H), 8.18 (d, 1H), 8.13 (d, 1H), 7.79 (d, 1H), 7.46–7.03 (m, 9H), 5.20 (m, 1H), 4.58 (m, 1H), 2.70 (m, 2H), 1.55–1.40 (m, 3H), 0.90 (m, 6H); HPLC (Gradient A), 29.5 min; MS, m/z 422.

EXAMPLE 4

Synthesis of BIO-1017

A. The procedure as described in Example 1A was performed utilizing 1-phenyl-1-cyclopropanecarboxylic acid (21 mg, 0.13 mmol), EDC (26 mg, 0.14 mmol), HOBt (26 mg, 0.17 mmol), amine from Example 3A (44 mg, 0.11 mmol) and diisopropylethylamine (0.10 mL, 0.56 mmol) in $CH_2Cl_2$ (5.0 mL) to afford BIO1017-OMe (39 mg, 68%) as a foam.

B. The procedure as described in Example 1B was performed utilizing BIO1017-OMe (39 mg, 0.089 mmol) and aq. LiOH (1.0 , 0.27 mL, 0.27 mmol) in MeOH (2 mL) to give BIO-1017A (10.3 mg, 27%) and BIO-1017B (12.2 mg, 32%) as white solids:

BIO-1017A: $^1$H NMR ($CD_3SOCD_3$, 300 MHz, ppm) 8.46 d, 1H), 7.40–7.20 (m, 10H), 6.30 (d, 1H), 5.09 (m, 1H), 4.33 (m, 1H), 2.62 (m, 2H), 1.50–1.20 (m, 5H), 0.98 (m, 2H), 0.82 (m, 6H); HPLC (Gradient A), 33.9 min; MS, m/z 423.
BIO—BIO- 1017B: $^1$H NMR ($CD_3SOCD_3$, 300 MHz, ppm) 8.55 (d, 1H), 7.48–7.15 (m, 10H), 6.30 (d, 1H), 5.08 (m, 1H), 4.35 (m, 1H), 2.63 (m, 2H), 1.48–1.15 (m, 5H), 1.10–0.88 (m, 2H), 0.85–0.64 (m, 6H); HPLC (Gradient A), 33.9 min and 34.5 min (1:9); MS, m/z 423.

EXAMPLE 5

Synthesis of BIO-1022

A. The procedure as described in Example 1A was performed utilizing 2-naphthylacetic acid (20 mg, 0.11 mmol), EDC (25 mg, 0.13 mmol), HOBt (25 mg, 0.16 mmol), amine from Example 3A (42 mg, 0.10 mmol) and diisopropylethylamine (0.10 mL, 0.56 mmol) in DMF (2.0 mL) to afford BIO1022-OMe (36 mg, 70%) as a foam.

B. The procedure as described in Example 1B was performed utilizing BIO1022-OMe (36 mg, 0.078 mmol) and aq. LiOH (1.0 M, 0.50 mL, 0.50 mmol) in MeOH (3 mL) to give BIO-1022A (1.7 mg, 4.8%) and BIO-1022B (6.8 mg, 19%) as white solids:

BIO-1022A: $^1$H NMR ($CDCl_3$, 300 MHz, ppm) 7.90–7.17 (m, 12H), 5.30 (t, 1H), 4.45 (m, 1H), 2.79 (m, 2H), 1.68–1.33 (m, 3H), 0.87 (d, 6H); HPLC (Gradient A), 25.7 min; MS, m/z 447.
BIO-1022B: $^1$H NMR ($CDCl_3$, 300 MHz, ppm) 7.90–7.17 (m, 12H), 5.35 (t, 1H), 4.49 (m, 1H), 2.79 (d, 2H), 1.58–1.33 (m, 3H), 0.82 (m, 6H); HPLC (Gradient A), 25.7 min and 26.4 min (1:9); MS, m/z 447.

EXAMPLE 6

Synthesis of BIO-1029

A. t-Butyl 3-amino-3-phenyl-1-propanoate was coupled with CbzLeuOSu using the method described in Procedure C. This material was subjected to the conditions of Procedure D2 to give the desired amine.

B. The procedure as described in Example 1A was performed utilizing 4-(2-aminobenzamido)-phenylacetic acid (18 mg, 0.067 mmol), EDC (13 mg, 0.067 mmol), and HOBt (13 mg, 0.085 mmol), amine from Example 6A (18 mg, 0.054 mmol) and diisopropylethylamine (0.048 mL, 0.27 mmol) in DMF (0.5 mL) to afford $NH_2$-BIO1029-OtBu (32 mg, 100%) as an oil: $^1$H NMR ($CDCl_3$, 300 MHz, ppm) 7.65–7.43 (m, 4H), 7.40–7.10 (m, 9H), 6.72 (m, 2H), 6.49 (d, 1H), 5.28 (m, 1H), 4.45 (m, 1H), 3.52 (s, 2H), 2.68 (m, 2H), 2.00 (bs, 2H), 1.65–1.15 (m, 13H), 0.85 (m, 6H).

C. A solution of $NH_2$-BIO1029-OtBu (16 mg, 0.027 mmol) in trifluoroacetic acid (1 mL) was stirred at room temperature for 45 min and then concentrated. The crude product was purified by HPLC to afford $NH_2$-BIO1029 (3.4 mg, 26%) as a white solid: MS, m/z 531.

D. A solution of $NH_2$-BIO1029 (3.4 mg, 0.0064 mmol), methyl isocyanate (3 drops), and diisopropylethylamine (1 drop) in $CH_2Cl_2$ (0.30 mL) was stirred at room temperature for 18 h and then concentrated in vacuo. The crude product was purified by HPLC to afford BIO1029 (2.6 mg, 69%) as a white solid: $^1$H NMR ($CD_3SOCD_3$, 300 MHz, ppm) consistent with structure; HPLC (Gradient A), 28.2 min; MS, m/z 588.

EXAMPLE 7

Synthesis of BIO-1032

A. The procedure as described in Example 1A was performed utilizing 3-amino-phenylacetic acid (29 mg, 0.19 mmol), EDC (44 mg, 0.23 mmol), and HOBt (44 mg, 0.29 mmol), amine from Example 6A (49 mg, 0.15 mmol) and diisopropylethylamine (0.17 mL, 0.95 mmol) in DMF (1;0 mL) to afford $NH_2$-BIO1032-OtBu (22 mg, 31%) as a foam after flash chromatography ($SiO_2$, 60% ethyl acetatehexane): $^1$H NMR ($CDCl_3$, 300 MHz, ppm) 7.45–7.05 (m, 7H), 6.75–6.50 (m, 3H), 5.97 (d, 1H), 5.30 (m, 1H), 4.46 (m, 1H), 3.50 (s, 2H), 2.71 (m, 2H), 1.70–1.39 (m, 3H), 1.33 (s, 9H), 0.84 (m, 6H).

B. A mixture of $NH_2$-BIO1032-OtBu (7.0 mg, 0.015 mmol), phenylsulfonyl chloride (1.7 µL, 0.014 mmol), and diisopropylethylamine (5.4 µL, 0.030 mmol) in $CH_2Cl_2$ was stirred at room temperature for 18 h. The reaction mixture was concentrated in vacuo and the residue diluted with ethyl acetate. The organic solution was washed with 60% sat. aq. $NaHCO_3$ (2×), $H_2O$, 5% citric acid (3×), $H_2O$, and sat. aq. NaCl, dried ($MgSO_4$) and concentrated. The residue (9 mg) was stirred in trifluoroacetic acid (1 mL) at room temperature for 30 min before concentrating in vacuo. The resulting crude product was purified by HPLC to afford BIO-1032 (3.9 mg, 47%) as a white solid: $^1$H NMR ($CD_3SOCD_3$, 300 MHz, ppm) 8.52 (d, 1H), 8.17 (d, 1H), 7.75 (d, 2H), 7.61–7.45 (m, 3H), 7.35–6.85 (m, 9H), 5.13 (m, 1H), 4.28 (m, 1H), 3.40 (m, 2H), 2.65 (bs, 2H), 1.50–1.12 (m, 3H), 0.79 (d, 3H), 0.71 (d, 3H); HPLC (Gradient B), 18.7 min; MS, m/z 552.

EXAMPLE 8

Synthesis of BIO-1093

A. To a stirred solution of the Boc-protected amine product of Procedure C (41.5 mg, 0.102 mmol) at 05° C. in 2 mL of $CH_2Cl_2$ was added 4 mL of TFA. The mixture was allowed to come to room temperature with continued stirring for 1 hour. The reaction was concentrated in vacuo, redissolved in $CH_2Cl_2$' concentrated two more times and placed under high vacuum to remove final traces of TFA. HPLC showed complete conversion to two new peaks of shorter retention time.

B. The material from Example 8A was redissolved in 0.75 mL DMF, cooled to 0–5° C. and DIEA was added until the mixture was basic to litmus and the ice bath was removed. This material combined with 4-nitrophenyl acetic acid (16.5 mg, 0.091 mmol), HOBt (20.4 mg, 0.151 mmol) and EDC (19.4 mg, 0.101 mmol) under conditions described in Example 1A to yield BIO 1093-OEt (21.4 mg, 50%) as a clear oil.

C. A solution of BIO 1093-OEt (21.4 mg, 0.053 mmol) in 1 ml of MeOH was stirred overnight at room temperature with 1N LiOH (130 µl, 0.13 mmol). The mixture was acidified (red to litmus) with TFA and concentrated in vacuo. Pure isomers were resolved via preparative HPLC followed by lyophilization. Repeated dissolution in 50/50 MeOH/$CH_2Cl_2$ and in vacuo concentration followed by 24 hours under high vacuum provided BIO-1093 (3 mg, 13%) of each isomer as white amorphous solids.

Isomer A: $^1$H NMR: ($CDCl_3$, 300 MHz, ppm), 8.09 (d 2H J=8.2 Hz), 7.38 (d, 2H, J=8.21 Hz), 7.15 (s, 5H), 5.21 (m, 1H), 4.32 (m, 1H), 3.28 (s, 1H), 2.67 (m, 2H), 1.40 (M, 3H), 0.75 (dd, 6H J=6.9, 7.6 Hz). FAB: 442 (M+H)$^+$, 464 (M+Na)+Mw 441.43. HPLC: Gradient 1 single peak>99% 19.5 min. Tlc: 10% MeOH/$CH_2Cl_2$ $R_f$=0.25, EtOAc plus 1% HOAc $R_f$=0.35.

Isomer B: $^1$H NMR: ($CDCl_3$, 300 MHz, ppm), 8.0 (d, 2H, J=9.7 Hz), 7.56 (d, 1H J=8.0 Hz), 7.73 d, 2H J=9.7 Hz), 7.07 (s, 5H), 5.15 (t, 1H, J=5.5 Hz), 4.29 (m, 1H), 3.45 (s, 2H), 2.65 (m, 2H), 1.45 (m, 3H), 0.78 (dd, 6H, J=6.9, 4.8 Hz). FAB: 442 (M+H)$^+$, 464(M+Na)$^+$, MW 441.43. HPLC: Single peak >99%, 19.3 min. Tlc: 10% MeOH/$CH_2Cl_2$ $R_f$=0.29, EtOAc plus 1% HOAc $R_f$=0.55.

EXAMPLE 9

Synthesis of BIO-1099

A. The amine from Example 3A (50.0 mg, 0.127 mmol) was subjected to the conditions described in Example 8B using diphenylacetic acid (25.6 mg, 0.121 mmol), HOBt (26 mg, 0.19 mmol), and EDC (27 mg, 0.14 mmol) in DMF to afford BIO 1099-OMe (49.2 mg, 83%) as a clear viscous oil.

B. BIO1099-OMe (49 mg, 0.1 mmol) was saponified and purified as described in Example 8C to provide BIO-1099A (7 mg, 15%) and BIO-1099B (5 mg, 11%) as white amorphous solids.

Isomer A: $^1$H NMR: ($CDCl_3$, 300 MHz, ppm)$_1$ 7.95 (d, 1H 8 Hz), 7.19 (m, 15H), 6.95 (d, 1H 8 Hz), 5.25 (t, 1H, J=3.2), 4.84 (s, 1H), 4.41 (m, 1H), 2.70 (dd, 2H, J=2.5, 1.3 Hz), 1.41 (m, 3H), 0.79 (dd, 6H, (J=6 Hz). FAB: (M+H) $^+$474, (M+Na)$^+$496 MW 472.54. HPLC: 1 peak; 100% pure; 30.074 min. Tlc: 10% MeOH/$CH_2Cl_2$ $R_f$=0.33; 50/50 EtOAc/Hex, 1% HOAc $R_f$=0.45.

Isomer B $^1$H NMR: ($CDCl_3$, 300 MHz, ppm) 7.72 (d, 1H, 8 Hz), 7.22 (m, 15H), 5.31 (t, 1H, 1.2 Hz), 6.70 (d, 1H 8 Hz), 4.93 (s, 1H), 4.60 (m, 1H), 2.68 (s, 1H), 2.65 (m, 2H), 1.35 (m, 3H), 0.61 (dd, 6H, J=2.5, 1.3 Hz). FAB: 473 (M+H)$^+$, 495 (M+Na)$^+$; MW 472.54. HPLC: 1 Peak; 100%; 30.38 min. Tlc: 10% MeOH/$CH_2Cl_2$ $R_f$=0.33, 50/50 EtOAc/Hex plus 1% HOAc $R_f$=0.38.

EXAMPLE 10

Synthesis of BIO-1100

A. The amine salt described in Example 6A (prepared from 40.5 mg, 0.093 mmol of Boc protected material) was taken up in 1.0 mL of DMF and TEA was added with stirring until basic to litmus.

B. The method described in Example 1A was performed using 2-bromo-5-methoxy-4-hydroxy phenyl acetic acid (23.1 mg, 0.089 mmol), HOBt (18.9 mg, 0.14 mmol), EDC (19.6 mg, 0.10 mmol) in 1.0 ml DMF and free amine prepared in Example 10A to give a white solid (49 mg, quantitative). An aliquot was purified by preparative reverse phase HPLC (gradient 2), lyophilized and dried by repeatedly dissolving in 50/50 MeOH/$CH_2Cl_2$ and concentrated under reduced pressure to yield BIO-1100 (1.8 mg) as an amorphous white solid. $^1$H NMR: ($CDCl_3$ 300 MHz, ppm), 7.25 (s, 5H), 7.05 (s, 1H), 6.30 (s, 1H), 5.28 (m, 1H), 3.81 (s, 3H), 3.59 (s, 2H), 2.77 (m, 2H), 1.45 (m, 3H), 0.82 (dd, 6H J=2.5, 1.2). FAB: (M+H)$^+$ 521, 523; (M+Na)$^+$ 543, 545; MW 521.44. HPLC: Major peak at 29.1 min; >97% purity. Tlc: 10% MeOH/$CH_2Cl_2$ $R_f$=0.16; 50/50 EtOAc/Hex plus 1% HOAc $R_f$=0.28.

EXAMPLE 11

Synthesis of BIO-1106

A. To a solution of 6-aminohexanoic acid (1.0 g, 7.6 mmol) in dioxane (6 ml) and water (6 ml) containing TEA (1.7 ml, 11.25-mmol) was added BOC-ON (2.1 g, 8.4 mmol, Aldrich). After stirring for 3 h at room temperature, the reaction was diluted with water (20 ml) and washed twice with ethyl acetate (10 ml). The aqueous was then acidified to PH=1–2 with 1N HCl and the aqueous layer extracted five times with ethyl acetate, dried over $Na_2SO_4$ and concentrated to afford 1106-1 (842 mg, 51%). $^1$HNMR ($CDCl_3$, 300 MHz, ppm): 4.61 (1H, bs), 3.15–2.95 (4H, bm), 2.55–2.23 (4H, m), 1.65–1.50 (4H), 1.46 (9H), 1.45–1.30 (2H, m).

B. t-Butyl 3-amino-3-phenyl-1-propanoate was coupled with CbzLeuOSu as described in Procedure C. This material was subjected to the conditions of Procedure D2 to give the desired free amine.

C. N-Boc 6-aminohexanoic acid (prepared in Example 11A) (17.3 mg, 0.075 mmol), HOBt (15.2 mg, 0.11 mmol) and EDC (17.3 mg, 0.09 mmol) were stirred in 0.5 ml of DMF at room temperature for 1.5 hours. The free amine from Example 11B (25 mg, 0.075 mmol) in 0.5 ml of DMF was added to the stirred solution of activated ester along with two drops of TEA so that the reaction was basic to litmus. After several hours the reaction was determined to be incomplete by HPLC. Small portions of N-Boc-6-aminohexanoic acid, HOBt, and EDC were then added to drive the reaction to completion. Purification, as detailed in Example 8C, provided BIO 1106 Boc t-butyl ester (26 mg, 63%) as a clear viscous oil. $^1$H NMR: ($CDCl_3$ 300 MHz, ppm), 7.40 (d, 1H, 8 Hz), 7.32–7.25 (m, 5H), 6.30 (d, 1H, J=8 Hz), 5.30 (q, 1H, J=7 Hz), 4.49 (m, 1H), 3.09 (bs, 2H), 2.79 (dd, 1H, J=8, 15 Hz), 2.69 (dd, 1H, J=7, 15 Hz), 2.20 (t, 2H J=8 Hz), 1.69–1.39 (m, 9H), 1.42 (s, 9H), 1.29 (s, 9H), 0.88 (m, 6H). HPLC: 1 peak, 100% purity at 28.3 min.

Both t-butyl protecting groups of BIO 1106 Boc t-butyl ester were removed as described in Example 10A. The resulting residue was stirred in 0.5 ml of DMF, made basic to litmus by the addition of two drops of TEA, followed by phenyl isocyanate (13.6 mg, 0.3 mmol) and stirred overnight. The reaction mixture was purified as detailed in Example 10B resulting in BIO-1106 (3.5 mg, 29%) as a beige amorphous solid. $^1$H NMR: ($CDCl_3$, 300 MHz, ppm), 7.97 (d, 1H, 8 Hz), 7.22 (m, 11H), 6.91 (t, 1H J=8 Hz), 5.30 (m, 1H), 4.33 (m, 1H), 3.12 (m, 6H), 2.63 (m, 2H), 2.13 (t, 2H, J=6 Hz), 1.41 (bm, 9H), 0.80 (m, 6H). FAB: (M+H)$^+$ 511, (M+Na)$^+$ 533; MW 510.59. HPLC: 1 peak; 100% at 19.4 min. Tlc: 15% MeOH/$CH_2Cl_2$ $R_f$=0.32, 10% MeOH/EtOAc plus 1% HOAc $R_f$=0.31.

EXAMPLE 12

Synthesis of BIO-1142

(±)-1-Benzocyclobutene carboxylic acid (16.3 mg, 0.11 mmol), HOBt (22.4 mg, 0.165 mmol), and EDC (23.7 mg, 0.121 mmol) were stirred in 0.5 ml DMF at room temperature for 45 minutes to give the activated ester. The product of Example 10A (15.3 mg, 0.055 mmol) was added to the activated ester and the mixture stirred for two hours. Filtration and preparative HPLC purification, as described in Example 10B, yielded BIO-1142 isomer A (4.4 mg, 70%) and BIO-1142 isomer B (4.9 mg, 22%) as white amorphous solids.

BIO-1142 isomer A: $^1$H NMR: (CDCl$_3$, 300 MHz,ppm), 7.79 (d, 1H J=8 Hz), 7.31–7.05 (m, 9H), 6.81 (d, 1H J=8 Hz), 5.24 (m, 1H), 4.36 (m, 1H), 4.15 (m, 1H), 3.00–3.50 (bm, 11H), 2.70 (m, 2H), 1.43 (m, 3H), 0.70 (m, 6H). FAB: (M+H)$^+$ 409 (M+Na)$^+$ 431; MW 408.46. HPLC: Major peak at 20.2 min; >99% purity. Tlc: 10% MeOH/CH$_2$Cl$_2$ R$_f$=0.46, EtOAc plus 1% HOAc R$_f$=0.53.

BIO-1142 isomer B: $^1$H NMR: (CDCl$_3$, 300 MHz, ppm), 7.92 (d, 1H, J=8 Hz), 7.31–7.05 (m, 9H), 6.91 (d, 1H, J=8z), 5.25 (m, 1H), 4.38 (m, 1H), 4.14 (m, 1H), 3.28 (m, 2H), 2.72 (m, 2H), 1.42 (m, 3H), 0.77 (m, 6H). FAB: (M+H)$^+$ 409 (M+Na)$^+$ 431; MW 408.46. HPLC: Major peak at 20.62 min; >96% purity. Tlc :10% MeOH/CH$_2$Cl$_2$ R$_f$=0.52; EtOAc plus 1% HOAc R$_f$=0.54.

EXAMPLE 13

Synthesis of BIO-1189

(±)-1-indancarboxylic acid (6.2 mg, 0.038 mmol), HOBt (7.7 mg, 0.057 mmol), and EDC (8.0 mg, 0.042 mmol) were stirred in 0.5 ml DMF at room temperature for two hours. The free amine prepared in Example 11B was treated with TFA and this material (10 mg, 0.038 mmol) was then added and the mixture stirred overnight. Filtration and preparative HPLC purification as described in Example 10B yielded BIO-1189 isomer A (less than 1 mg) and isomer B (2 mg, 12%) as white amorphous solids.

BIO-1189 isomer A: $^1$H NMR: (CDCl$_3$, 300 MHz, ppm), 7.3–7.1 (m, 12H), 5.32 (m, 1H), 4.48 (m, 1H), 3.91 (t, 1H J=6.6 Hz), 3.1–2.7 (m, 3H), 2.5–2.2 (m, 1H), 1.6–1.4 (m, 3H), 0.85 (m, 6H). FAB: (M+H)$^+$, 423 (M+Na)$^+$ 445; MW 422.5. HPLC: Major peak 21.2 min.; >97% purity. Tlc: 5% MeOH/CH$_2$Cl$_2$ R$_f$=0.19; EtOAc plus 1% HOAc R$_f$=0.73.

BIO-1189 isomer B: $^1$H NMR: (CDCl$_3$, 300 MHz, ppm), 7.7 (d, 1H, J=8 Hz), 7.45–7.1 (m, 9H), 6.65 (d, 1H, J=8 Hz), 5.33 (m, 1H), 4.48 (m, 1H), 3.90 (t, 1H, J=6.6 Hz), 3.1–2.8 (m, 3H), 2.45–2.3 (m, 2H), 1.48 (m, 3H), 0.80 (m, 6H). FAB: (M+H)$^+$ 423 (M+Na)$^+$ 445; MW 422.5. HPLC: Major peak 21.5 min; >94% purity. Tlc: 5% MeOH/CH$_2$Cl$_2$ R$_f$=0.12, EtOAc plus 1% HOAc R$_f$=0.60.

EXAMPLE 14

Synthesis of BIO-1006

A. Amine β-3 was coupled with BocLeuOSu according to Procedure C (product recrystallized from diethyl ether) and deprotected according to Procedure D to give the desired TFA-amine salt.

$^1$H-NMR (300 MHz, CDCl$_3$) for BOC amine: 0.90 (m, 6H), 1.42 (9H), 1.55–1.75 (m, 3H), 2.8 (m, 2H), 3.61 (s, 3H), 4.05 (m, 1H), 4.83 (m, 1H), 5.26 (m, 1H), 5.92 (s, 2H), 6.686.78 (m, 3H), 7.06 (d, 1H).

$^1$H-NMR (300 MHz, CDCl$_3$) for TFA-amine: 0.83 (d, 3H), 0.87 (d, 3H), 1.50 (m, 1H), 1.63 (bt, 2H), 2.73–2.92 (m, 2H), 3.63 (s, 3H), 4.27 (bs, 1H), 5.26 (m, 1H), 5.95 (s, 2H), 6.66–6.78 (m, 3H), 7.58 (bs, 3H), 8.02 (d, 1H).

B. A solution of amine-TFA salt of Example 14A (24 mg) in CH$_2$Cl$_2$ was added to 4-hydroxyphenylacetic acid succinimidyl ester (14 mg, 1.1 eq) and stirred at room temperature for about 2 hours. The reaction mixture was washed with 5% citric acid (2×), sat. aq. NaHCO$_3$ (2×) and brine (1×), dried (Na$_2$SO$_4$), filtered and concentrated to give 28 mg of crude BIO-1006 methyl ester. $^1$H-NMR: (300 MHz, CDCl$_3$) 0.82 (6H), 1.35–1.58 (3H), 2.62–2.82 (2H), 3.48 (2H), 3.57 (3H), 4.41 (1H), 5.70 (1H), 5.89 (2H), 6.08 (1H), 6.65–6.75 (5H), 7.04 (2H), 7.22 (1H).

C. Crude BIO-1006 methyl ester in MeOH was added to 1 N LiOH and stirred at room temperature for about 1 hour. The reaction mixture was neutralized by trifluoroacetic acid and purified by HPLC. The clean fraction was collected and dried to give BIO-1006. $^1$H-NMR (300 MHz, CDCl$_3$): 0.73 (d, J=6 Hz, 3H), 0.80 (d, J=6 Hz, 3H), 1.35 (bt, 2H), 1.45 (m, 1H), 2.40 (m, 2H), 3.223.38 (m, 2H), 4.23 (bq, 1H), 5.02 (m, 1H), 5.93 (s, 2H), 6.65 (d, J=8 Hz, 2H), 6.68–6.80 (m, 2H), 6.83 (s, 1H), 7.03 (d, J=8 Hz, 2H), 8.11 (bd, 1H). Mass Spec. M/z=457

EXAMPLE 15

Synthesis of BIO-1050

A. To a suspension of 4-amino phenylacetic acid (9 g, 60 mmol) and N-(benzyloxycarbonyloxy)succinimide (15 g, 60 mmol) in CH$_2$Cl$_2$ was added enough triethylamine to form a homogeneous solution. The mixture was stirred at room temperature for 30 min and then CH$_2$Cl$_2$ was removed by rotavapor. The resulting residue was dissolved in water and acidified with 5% HCl. The solid thus formed was filtered and washed with 5% HCl, water, and diethyl ether to give 12 g (70%) of Cbz-aminophenylacetic acid as a brownish powder. $^1$H-NMR (300 MHz, DMSO-d$_6$): 3.48 (s, 2H), 5.13 (s, 2H), 7.14 (d, 2H), 7.29–7.45 (m, 7H), 9.73 (s, 1H).

B. The method of Example 1A was performed using Cbz-aminophenylacetic acid from Example 15A (342 mg, 1.2 mmol) in DMF, HOBT (275 mg, 1.8 mmol), EDC (276 mg, 1.44 mmol), and a solution of free amine prepared in Example 14A (432 mg, 0.94 mmol) in DMF to give the coupled product which was used without further purification.

C. The product of Example 15B was subjected to hydrogenation (H$_2$, 50 psi, 10% Pd/C, MeOH/H$_2$O, overnight). The reaction mixture was filtered through a pad of Celite®, and concentrated to give 0.4 g (90%) of free amine as a brown powder. $^1$H-NMR (300 MHz, CDCl$_3$): 0.82 (m, 6H), 1.30–1.62 (m, 3H), 2.62–2.82 (m, 2H), 3.45 (s, 2H), 3.57 (s, 3H), 4.37 (m, 1H), 5.18 (m, 1H), 5.91 (s, 2H), 6.65–6.80 (m, 5H), 7.02 (d, 2H).

D. To a solution of free amine from Example 15C (22 mg) in CH$_2$Cl$_2$ was added phenylisocyanate (8 mg, 1.5 eq) with one drop of triethylamine. The solution was then stirred at room temperature for 2 hours. After diluting with ethyl acetate (15 mL), the mixture was washed with 5% citric acid (2×), sat. aq. NaHCO$_3$ (2×) and brine (1×), dried (Na$_2$SO$_4$), filtered and concentrated to give the crude phenylureamethyl ester.

E. The crude phenylureamethyl ester was dissolved in MeOH and 1 N LiOH was added at 0° C. and mixture was stirred at room temperature for 2 h. After neutralization with trifluoroacetic acid, the reaction mixture was purified by HPLC. The pure fraction was collected and dried to give BIO-1050. $^1$H-NMR: (300 MHz, DMSO-D6): 0.76 (d, 3H), 0.80 (d, 3H), 1.30–1.50 (m, 3H), 2.52–2.72 (m, 2H), 3.28–3.50 comp, 2H), 4.30 (m, 1H), 5.06 (m, 1H), 5.97 (s, 2H), 6.70 (d, 1H), 6.79–6,87 (m, 2H), 6.95 (t, 1H), 7.13 (d, 2H), 7.25 (t, 2H), 7.34 (d, 2H), 7.43 (d, 2H), 3.12 (d, 1H), 8.40 (d, 1H), 8.60 (s, 1H), 8.66 (s, 1H). Mass Spec: M/z=575.

EXAMPLE 16

Synthesis of BIO-1068

The procedure of Example 15D was followed utilizing cyclohexylisocyanate for phenylisocyanate. The resulting product was hydrolyzed as described in Example 15E and the pure fraction from HPLC purification was collected and dried to give BIO-1068. $^1$H—NMR (300 MHz, DMSO-d$_6$): 0.73 (d, J=6 Hz, 3H), 0.80 (d, J=6 Hz, 3H), 1.05–1.85 (m, 13H), 2.50–2.75 (m, 2H), 3.23–3.50 (m, 3H), 4.28 (bq, 1H), 5.05 (bq, 1H), 5.95 (bs, 2H), 6.02 (d, J=8 Hz, 1H), 6.72 (bd, 1H), 6.71 (d, J=8 Hz, 1H), 6.84 (bs, 1H), 7.08 (d, J=8 Hz, 2H), 7.25 (d, J=8 Hz, 2H), 8.07 (d, J=8 Hz, 1H), 8.20 (s, 1H), 8.40 (d, J=8 Hz, 1H). Mass Spec. M/z=581.

EXAMPLE 17

Synthesis of BIO-1079

The procedure of Example 15D was followed utilizing 2-methoxyphenylisocyanate for phenylisocyanate. The resulting product was hydrolyzed as described in Example 15E and the pure fraction from HPLC purification was collected and dried to give Bio-1079. $^1$H-NMR (300 MHz, DMSO-d6): 0.75 (d, 3H), 0.80 (d, 3H), 1.30–1.50 (m, 3H), 2.50–2.72 (m, 2H), 3.30–3.45 (m, 2H), 3.85 (s, 3H), 4.28 (m, 1H), 5.06 (m, 1H), 5.96 (bs, 2H), 6.69–7.02 (m, 8H), 7.13 (d, 2H), 7.34 (d, 2H), 8.05–8.15 (m, 3H), 8.42 (bd, 1H), 8.87 (s, 1H), 9.13 (s, 1H). Mass Spec. M/z=605.

EXAMPLE 18

Synthesis of BIO-1082

A. Triethylamine was added to a solution of the TFA-amine salt prepared in Procedure D (43 mg) in CH$_2$Cl$_2$ at 0° C. until pH reached 9.0 was reached, followed by the addition of 4-phenylbutyryl chloride (26 mg). After stirring at room temperature for 2 h, the reaction mixture was diluted with ethyl acetate (20 mL) and then washed with 5% citric acid (2×), sat. aq. NaHCO$_3$ (2×) and brine (1×), dried (Na$_2$SO$_4$), filtered and concentrated to give the desired product as an ethyl ester.

B. The crude ethyl ester was dissolved in MeOH, 1 N LiOH was added at 0° C. and the mixture was stirred at room temperature for 2 h. After neutralization with trifluoroacetic acid, the reaction mixture was purified by HPLC. Two diastereomers were separated and the pure fractions were collected and dried to give Bio-1082-A and Bio-1082-B. Bio-1082-B $^1$H-NMR (300 MHz, DMSO-d$_6$): 0.79 (d, 3H), 0.83 (d, 3H), 1.29–1.37 (m, 2H), 1.47 (m, 1H), 1.70–1.83 (m, 2H), 2.08–2.17 (m, 2H), 2.48–2.58 (m, 2H), 2.67 (bt, 2H), 4.31 (m, 1H), 5.03 (m, 1H), 7.12–7.32 (m, 10H), 7.90 (d, 1H), 8.45 (d, 1H). Mass. Spec. M/z=425.

EXAMPLE 19

Synthesis of BIO-1148

A. Amine β-13 was coupled with BocLeuOSu using the method described in procedure C. This material was subjected to the conditions of Procedure D1 to give the desired amine salt 1148-1.

B. To a solution of 4-hydroxyphenylacetic acid (3.0 g, 20 mmol) in DMF was added HOBT (3.7 g, 24 mmol) followed by EDC (4.2 g, 22 mmol) and the mixture was stirred at room temperature for 30 min. N-hydroxysuccinimide (2.3 g, 20 mmol) was added and stirred at room temperature overnight. The resulting mixture was diluted with ethyl acetate (150 ml), extracted with 5% citric acid (2×), saturated NaHCO$_3$ (2×) and brine (1×) and was dried over anhydrous Na$_2$SO$_4$. Following removal of the solvent in vacuo the product was dissolved in CH$_2$Cl$_2$ and precipitated with hexanes to afford 4-hydroxyphenylacetic acid succinimidyl ester (3.9 g, 78%). $^1$H NMR (300 MHz, DMSO-d$_6$): 2.79 (s, 4H), 3.93 (s, 2H), 6.72 (d, J=8.5 Hz, 2H), 7.12 (d, J=8.5 Hz, 2H), 9.41 (s, 1H).

C. Amine salt 1148-1 was hydrolysed under MeOH/aqueous LiOH conditions to give an acid. A solution of this acid, triethylamine, and 4-hydroxyphenylacetic acid-OSu (prepared in Example 19B) in CH$_2$Cl$_2$ was stirred at room temperature for 1 h. The reaction mixture was purified by HPLC and the pure fraction was collected and dried to give Bio-1148 as a mixture of two diastereomers. $^1$H-NMR (300 MHz, DMSO-d$_6$): 0.70–0.90 (m, 6H), 1.29–1.63 (m, 3H), 2.73–2.85 (m, 2H), 3.17–3.40 (m, 2H), 4.15–4.30 (m, 1H), 5.12–5.28 (m, 1H), 6.58–6.68 (m, 2H), 6.94–7.06 (m, 2H), 7.54–7.67 (m, 1H), 7.93–8.16 (m, 2H), 8.53–8.75 (m, 3H). Mass. Spec. M/z=414.

EXAMPLE 20

Synthesis of BIO-1168

The procedure that was used in Example 15D was followed utilizing 3-methylphenylisocyanate for phenylisocyanate. The resulting product was hydrolyzed as described in Example 15E and the pure fraction from HPLC purification was collected and dried to give Bio-1168. $^1$H-NMR (300 MHz, DMSO-d$_6$): 0.76 (d, 3H), 0.82 (d, 3H), 1.30–1.52 (m, 3H), 2.28 (s, 3H), 2.54–2.70 (m, 2H), 3.35–3.48 (m, 2H), 4.28 (m, 1H), 5.07 (m, 1H), 5.96 (m, 2H), 6.68–6,86 (m, 4H), 7.10–7.25 (m, 4H), 7.30 (s, 1H), 7.35 (d, 2H), 8.11 (d, 1H), 8.44 (d, 1H), 8.63 (s, 1H), 8.67 (s, 1H). Mass Spec. M/z=589.

EXAMPLE 21

Synthesis of BIO-1179

The procedure that was used in Example 15D was followed utilizing 2-methylphenylisocyanate for phenylisocyanate. The resulting product was hydrolyzed as described in Example 15E and the pure fraction from HPLC purification was collected and dried to give Bio-1179. $^1$H-NMR (300 MHz, DMSO-d$_6$): 0.75 (d, 3H), 0.80 (d, 3H), 1.27–1.51 (m, 3H), 2.23 (s, 3H), 2.62 (m, 2H), 3.40 (m, 2H), 4.28 (m, 1H), 5.06 (m, 1H), 5.98 (bs, 2H), 6.71 (bd, 1H), 6.80 (d, 1H), 6.83 (bs, 1H), 6.92 (bt, 1H), 7.05–7.20 (m, 4H), 7.38 (d, 2H), 7.82 (d, 1H), 7.87 (s, 1H), 8.10 (d, 1H), 8.42 (d, 1H), 8.93 (s, 1H). Mass Spec. M/z=589.

EXAMPLE 22

Synthesis of BIO-1195

A. Amine β-9 was coupled with BocLeuOSu according to Procedure C to give the desired product. ¹H-NMR (300 MHz, CDCl₃): 0.90 (m, 6H), 1.32 (s, 9H), 1.42 (s, 9H), 1.58–1.90 (m, 3H), 2.61–2.80 (m, 2H), 4.08 (m, 1H), 4.89 (bd, 1H), 5.37 (bq, 1H), 6.95–7.15 (m, 3H), 7.45 (bd, 1H).7

B. The product of Example 22A was treated with TFA as described in Procedure D to give the corresponding TFA-amine salt 1195-2.

C. A mixture of 4-amino-phenylacetic acid (10.0 g, 66.1 mmol) and 98% phenyl isocyanate (8.27 g, 68.0 mmol) in ethyl acetate (100 mL) was stirred at RT for 1 h then refluxed for 1.5 h. The mixture was allowed to cool to RT and the product was filtered, washed with ethyl acetate, methanol, and then ether affording phenylureaphenylacetic acid 1195-3 (17.5 g, 98%) as a white powder. ¹HNMR (DMSO-d⁶, 300 MHz, ppm): 8.72–8.64 (m, 2H), 7.44 (d, 2H), 7.36 (d, 2H), 7.28 (d, 2H), 7.16 (d, 2H), 6.96 (t, 1H), 3.52 (s, 2H). FAB-MS=272.

C. A solution of phenylureaphenylacetic acid 1195-3, HOBT, and EDC in DMF was stirred at room temperature for 30 min and then the free amine prepared from the product of Example 22B and TEA treatment was added. After stirring at room temperature overnight, the reaction mixture was purified by HPLC and the pure fraction was collected and dried to give Bio-1195. ¹H-NMR (300 MHz, DMSO-d₆): 0.71 (d, 3H), 0.78 (d, 3H), 1.25–1.46 (m, 3H), 2.56–2.72 (m, 2H), 3.26–3.41 (m, 2H), 4.21 (bq, 1H), 5.07 (bq, 1H), 6.90 (bt, 1H), 7.02–7.14 (m, 3H), 7.17–7.42 (m, 8H), 8.10 (d, 1H), 8.47 (d, 1H), 8.58 (s, 1H), 8.63 (s, 1H). Mass Spec. M/z=567.

EXAMPLE 23

Synthesis of BIO-1198

A. To a solution of phosgene in $CH_2Cl_2$ at 0° C. was added a solution of morpholine and triethylamine in $CH_2Cl_2$ dropwise. The reaction was then stirred at room temperature for 30 min and concentrated in vacuo to give a white solid. This crude product was dissolved in $CH_2Cl_2$ and 4-aminophenylacetic acid t-butyl ester was added. The mixture was stirred at room temperature overnight, diluted with ethyl acetate (20 mL), washed with 5% citric acid (2×), sat. aq NaHCO₃ (2×) and brine (1×), dried (Na₂SO₄), filtered and concentrated to give morpholineurea t-butyl ester 1198-1. ¹H-NMR (300 MHz, CDCl₃): 1.40 (s, 9H), 3.38–3.46 (m, 4H), 3.60–3.70 (m, 6H), 6.67 (s, 1H), 7.13 (d, 2H), 7.27 (d, 2H).

B. The morpholineurea t-butyl ester 1198-1 was dissolved in $CH_2Cl_2$ and trifluoroacetic acid was added. The solution was stirred at room temperature for 3 h. and concentrated to give 26 mg of the corresponding carboxylic acid 1198-2.

C. The method described in Example 1A was performed using carboxylic acid 1198-2 (26 mg) dissolved in DMF, HOBT, EDC, and the amine prepared in Example 14A to give 27 mg of crude methyl ester 1198-3.

D. A solution of crude methyl ester 1198-3 was treated as described in Example 14C to give Bio-1198. ¹H-NMR (300 MHz, DMSO-d₆) for BIO 1198: 0.75 (d, 3H), 0.82 (d, 3H), 1.27–1.50 (m, 3H), 2.53–2.70 (m, 2H), 3.28–3.45 (m, 6H), 3.55–3.60 (m, 4H), 4.27 (m, 1H), 5.07 (bq, 1H), 5.96 (bs, 2H), 6.72 (bd, 1H), 6.82 (d, 1H), 6.85 (bs, 1H), 7.09 (d, 2H), 7.35 (d, 2H), 8.08 (d, 1H), 8.42 (d, 1H), 8.47 (s, 1H). Mass Spec. M/z=569

EXAMPLE 24

Synthesis of Bio-1190

A. Amine β-5 was coupled with BocLeuOSu as described in Procedure C. This material was subjected to the conditions of Procedure D1 to give the desired amine salt.

B. The protocol described in Example 1A was performed using 2-methylphenylureaphenylacetic acid (135 mg, 0.47 mmol) in DMF (2.5 ml), HOBt (135 mg, 0.88 mmol), EDC (0.71 mmol) and the amine salt from Example 29A (200 mg, 0.46 mmol) (treated with Et₃N until pH 10 was reached) to give 1190-1 (235 mg, 89%) as a white solid.

C. To a stirred solution of 1190-1 (20 mg, 0.034 mmol) in MeOH (3 mL) was added aqueous LiOH (3 mL of 2N). After stirring at room temperature overnight, the reaction mixture was cooled to 0° C. and acidified by adding TFA until pH=3–4 (pH paper). The desired product was isolated and purified by LC (Vydac C18 column; gradient 8) to give 10 mg (0.017 mmol; 50%) of BIO-1190 as a white solid. ¹H NMR (DMSO-d⁶, 300 MHz, ppm) 8.95 (s, 1H, NH), 8.39 (d, 1H, J=9 Hz, NH), 8.11 (d, 1H, J=9 Hz, NH), 7.88 (s, 1H, NH), 7.83 (d, 1H, J=8 Hz, Ar), 7.36 (d, 2H, J=8.4 Hz, Ar), 7.2–7.1 (comp, 6H, Ar), 6.92 (m, 1H, Ar), 6.83 (d, 2H, J=9 Hz, Ar), 5.08 (m, 1H), 4.28 (m, 1H), 3.70 (s, 3H, OMe), 3.39 (d, 1H, J=8 Hz), 3.31 (d, 1H, J=7 Hz), 2.63 (m, 1H), 2.23 (s, 3H, Me), 1.50–1.25 (comp, 3H), 0.81 (d, 3H, J=6 Hz), 0.75 (d, 3H, J=6 Hz); FABMS, m/z 575 ($C_{32}H_{38}N_4O_6$ of M⁺1 requires 575).

EXAMPLE 25

Synthesis of Bio-1197

A. Amine β-1 (0.884 g, 4.0 mmol) was coupled with BocLeuOSu (1.32 g, 4.0 mmol) as described in Procedure C. This material was subjected to the conditions of Procedure D1 to give the desired amine salt (1.42 g, 85%) as a white solid. ¹H NMR (CDCl₃, 300 MHz, ppm): 7.31–7.22 (m, 5H), 7.14 (d, 1H), 5.37–5.30 (m, 1H), 4.84 (m, 1H), 4.10 (m, 1H), 2.85–2.66 (m, 2H), 1.721.58 (m, 2H), 1.51–1.49 (m, 1H), 1.48 (s, 9H), 1.29 (s, 9H), 0.91 (m, 9H).

B. The procedure of Example 1A was performed using 2-methylphenylureaphenylacetic acid (34 mg, 0.12 mmol), HOBT (20 mg, 0.14 mmol), EDC (26 mg, 0.134 mmol) and the amine salt of Example 25A (30 mg, 0.079 mmol) in the presence of Et₃N to give 15 mg (0.028 mmol; 35%) of Bio-1197 as a white foam: FABMS, m/z 545 ($C_{31}H_{36}N_4O_5$ of M⁺1 requires 545).

EXAMPLE 26

Synthesis of BIO-1201

A. The procedure of Example 15D was performed using the free amine from Example 15C (40 mg, 0.086 mmol) and 2-nitrophenyl isocyanate (28 mg, 0.172 mmol) to give 50 mg (92%) of 1201-1 as a light yellow oil. ¹H NMR (DMSO-d⁶, 300 MHz, ppm) 8.55 (d, 1H, NH), 8.50 (d, 1H, NH), 8.15 (d, 1H, NH), 8.05 (d, 1H, NH), 7.6–6.7 (11H, Ar), 5.85 (bs, 2H), 5.25 (m, 1H), 4.6 (m, 1H), 3.83.55 (comp), 3.5 (s, 3H, OMe), 2.75 (m, 2H), 1.7–1.4 (comp, 3H), 0.85 (m, 6H).

B. The procedure of Example 24C was performed using 1201-1 (50 mg, 0.079 mmol) to give 17 mg (0.027 mmol; 35%) of BIO-1201 as a light yellow solid. FABMS, m/z 620 ($C_{31}H_{35}N_5O_9$ of M⁺1 requires 620).

EXAMPLE 27

Syntheis of Bio-1217

A. Amine β-4 (30 mg, 0.1 mmol) was coupled with Nα-t-Boc-Nε-CBZ-$_L$-Lysine-N-Hydroxysuccinimide (50 mg, 0.1 mmol) as described in Example 25A to give 60 mg (93%) of 1217-1 as a white foam. $^1$H NMR (CDCl$_3$, 300 MHz, ppm) 7.35–7.25 (comp, 5H, Ar), 6.8–6.7 (comp, 3H, Ar), 5.35.1 (comp, 2H), 4.95 (m, 1H), 4.05 (m, 1H), 3.8 (s, 3H, OMe), 3.78 (s, 3H, OMe), 3.1 (m, 2H), 2.7 (m, 2H), 1.9–1.4 (comp), 1.35 (s, 9H, But), 1.3 (s, 9H, But).

B. Compound 1217-1 (60 mg, 0.09 mmol) in CH$_2$Cl$_2$ (5 mL) was deprotected with trifluoroacetic acid (0.5 mL) as described in Procedure D1 to give 56 mg (100%) of 1217-2 as a white foam. $^1$H NMR (CDCl$_3$, 300 MHz, ppm) 8.75 (bs), 7.35–7.15 (comp, Ar), 6.85–6.65 (comp, Ar), 5.4 (m), 5.2–4.9 (bs, Bn), 4.15 (m), 3.75 (bs), 3.15–2.6 (comp), 1.8 (m),1.4–1.0 (comp).

C. The procedure of Example 1A was performed using 2-methylphenylureaphenylacetic acid (40 mg, 0.14 mmol), HOBT (23 mg,0.167), EDC (30 mg, 0.158 mmol) and amine 1217-2 (56 mg, 0.093 mmol) was added in the presence of Et$_3$N to give 21 mg (30%) of BIO-1217 as a white foam. $^1$H NMR (DMSO-d$_6$, 300 MHz, ppm) 9.05 (m, 1H, NH), 8.4 (m, 1H, NH), 8.1 (m, 1H, NH), 8.0 (m, 1H, NH), 7.4–6.7 (comp, Ar), 5.1 (m, 1H), 5.0 (bs, 2H), 4.2 (m, 1H), 3.7 (bs, 6H, OMe), 2.9–2.6 (comp), 2.2 (s, 3 H, Me),1.6–1.1 (comp); FABMS, m/z 754 (C$_{41}$H$_{47}$N$_5$O$_9$ of M$^+$1 requires 754)

EXAMPLE 28

Synthesis of BIO-1225

A. Amine β-3 (90 mg, 0.4 mmol) coupled with Nα-t-Boc-Nε-CBZ-L-Lysine-N-Hydroxysuccinimide (193 mg, 0.4 mmol) as described in Example 25A to give 220 mg (94%) of 1225-1 as a white foam. $^1$H NMR (CDCl$_3$, 300 MHz, ppm) 7.4–7.25 (5H, Ar), 7.1 (m, 1H, NH), 6.8–6.65 (3H, Ar), 5.9 (s, 2H), 5.25 (m, 1H), 5.15 (m, NH), 5.05 (s, 2H), 4.85 (m, 1H), 4.0 (m, 1H), 3.6 (s, 3H, OMe), 3.15 (m, 2H), 2.80 (m, 2H), 1.90–1.20 (6H), 1.4 (s, 9H).

B. The BOC protecting group of 1225-1 (170 mg, 0.29 mmol) was removed as described in Procedure D1 to give 100 mg (71%) of free amine 1225-2 as a white foam.

$^1$H NMR (CDCl$_3$, 300 MHz, ppm) 8.07 (d, 1H, J=9 Hz), 7.47.2 (comp, 5H), 6.80–6.65 (comp, 3H), 5.90 (s, 2H), 5.25 (m, 1H), 5.05 (s, 2H), 4.98 (bs, 1H), 3.58 (s, 3H, OMe), 3.32 (m, 1H), 3.16 (m, 2H), 2.27 (m, 2H), 1.90–1.70 (comp, 3H), 1.6–1.25 (comp, 5H).

C. The procedure of Example 1A was performed using 2-methylphenylureaphenylacetic acid (44 mg, 0.155 mmol), HOBT (36 mg, 0.264 mmol), EDC (47 mg, 0.248 mmol) and free amine 1225-2 (50 mg, 0.103 mmol) to give 46 mg (80%) of BIO-1225-3 as a white foam. $^1$H NMR (DMSO-d$^6$, 300 MHz, ppm) δ 9.0–6.7 (21H, Ar & NH),5.96 (s, 2H), 5.1 (m, 2H), 4.98 (s, 2H), 4.2 (m, 1H), 3.50 (s, 3H, OMe), 3.48–3.4 (comp, 2H), 2.88 (m, 2H), 2.71 (m, 2H), 2.24 (s, 3H, Me),1.6–1.0 (comp, 6H); FABMS, m/z 752 (C$_{\_}$H$_{45}$N$_5$O$_9$ of M$^+$1 requires 752).

D. BIO-1225-3 (25 mg, 0.033 mmol) was treated as described in Example 24C to give 15 mg (62%) of BIO1225 as a white solid. FABMS, m/z 738 (C$_{40}$H$_{43}$N$_5$O9 of M$^+$1 requires 738).

EXAMPLE 29

Synthesis of BIO-1036

A. The method described in Procedure C was followed using methyl 3-amino-5-indanyl-1-propanoate (ester M-1, preparation described in Procedure B) (85 mg, 0.33 mmol) to give 1036-1 as a yellow foam (96 mg, 0.22 mmol, 67%) which was used without further purification in the next step. $^1$H NMR (CDCl$_3$): δ 7.15 (3H)$_1$ 6.95 (1H), 5.30 (1H), 4.95 (1H), 4.15 (1H), 3.55 (3H), 2.90–2.80 (6H), 2.05 (3H), 1.70 (2H), 1.35 (9H), 0.85 (6H).

B. Compound 1036-1 (98 mg, 0.22 mmol) was treated as described in Procedure D to produce the corresponding amine salt. The method described in Example 1A was performed using phenylacetic acid and the resulting amine salt (in the presence of TEA) to give 1036-2 as a yellowish solid (75 mg, 0.17 mmol, 77%), which was used without further purification in the next step. $^1$H NMR(CDCl$_3$): δ 7.35–6.8 (9H), 6.25 (1H), 5.25 (1H), 4.45 (1H) 3.6 (1.5H) 3.5 (1.5H), 2.80–2.60 (6H), 2.00 (2H), 1.70–1.30 (5H), 0.85 (6H).

C. Using the general procedure above a small portion of compound 1036-2 was hydrolyzed as described in Example 1B, purified by HPLC and the clean fractions collected to afford Bio-1036A (~2 mg) m/z=437 (98% pure by HPLC) along with Bio-1036B (~2 mg) m/z=437 (98% pure by HPLC) as white solids.

Bio-1036A: $^1$H NMR (300 MHz, DMSO-d$_6$): δ 8.45 (1H, d, J=7.3 Hz), 8.21 (1H, d, J=7.3 Hz), 7.37–7.05 (8H, m), 5.20 (1H, m), 4.37 (1H, m), 3.57–3.43 (2H, m), 2.86 (4H, m), 2.69 (2H, m), 2.03 (2H, m), 1.60 (1H, m), 1.49 (2H, m), 0.91 (3H, d, J=6.3 Hz), 0.84 (3H, d, J=6.3 Hz).

Bio-1036B: $^1$H NMR (300 MHz, DMSO-d$_6$): δ 8.45 (1H, d. J=8.4 Hz), 8.22 (1H, d, J=8.4 Hz), 7.40–7.00 (8H, m), 5.18 (1H, m), 4.35 (1H, m), 3.55 (2H, m), 2.85 (4H, m), 2.57 (2H, m) 2.05 (2H, m), 1.55 (1H, m), 1.40 (2H, m), 0.90 (3H, d, J=6.3 Hz), 0.75 (3H, d, J=6.3 Hz).

EXAMPLE 30

Synthesis of BIO-1137

A. The method described in Procedure C was followed using methyl 3-amino-3-(2-nitrophenyl)-1-propanoate (ester M-3, preparation described in Procedure B) (58 mg, 0.22 mmol) to afford 1137-1 (106 mg, 0.22 mmol, 100%) as a thick pale yellow oil. $^1$H NMR(CDCl$_3$) δ 7.95 (1H), 7.85–7.35 (5H), 5.85 (1H), 4.95 (1H), 4.15 (1H), 3.55 (1.5H), 3.50 (1.5H), 2.90 (2H), 1.70–1.60 (2H), 1.45 (9H), 0.90 (6H).

B. Compound 1137-1 (106 mg, 0.22 mmol) was treated as described in Example 29B to afford 1137-2 (69 mg, 0.16 mmol, 73%) as a yellow semi-solid. $^1$H NMR (CDCl$_3$): δ 7.90–7.15 (10H), 6.35 (0.5H), 6.20 (0.5H), 5.75 (1H), 4.45 (1H), 3.55 (1.5H), 3.50 (1.5H), 2.85 (4H), 1.70–1.30 (3H), 0.70 (6H).

C. A small portion of compound 1137-1 was hydrolyzed as described in Example 1B, purified by HPLC and the clean fractions isolated to afford Bio-1137A (~1 mg) m/z=442 (97% pure by HPLC) and Bio-1137B (~2 mg) m/z=442 (100% pure by HPLC).

EXAMPLE 31

Synthesis of BIO-1043

A. The commercially available N-BOC-1-aminocyclopropane carboxylic acid (80 mg, 0.4 mmol) in DMF (3 mL) was activated at room temperature using BOP (221 mg, 0.5 mmol). After 15 minutes the methyl 3-amino-3-phenyl-1-propanoate HCl salt (86 mg, 0.4 mmol) (neutralized with excess Hunig's base (0.15 mL, 0.8 mmol)) was added in DMF (1 mL). After stirring overnight at room temperature the reaction was diluted with ethyl acetate (10 mL), washed with 60% sat. bicarbonate (2×10 mL), 5% citric acid (2×5 mL) and brine (10 mL), dried over sodium sulfate and concentrated to afford 1043-1 as a white foam (143 mg, 0.4 mmol, 100%). $^1$H NMR (CDCl$_3$): δ 7.6 (1H), 7.2 (5H), 5.4–5.3 (2H), 3.55 (3H), 2.85–2.70 (2H), 1.55 (2H), 1.40 (9H), 0.9 (2H).

B. A small portion of compound 1043-1 was hydrolysed as described in Example 1B and purified by HPLC. Collection of the pure fractions afforded Bio-1043 (~3 mg) m/z=349 (100% pure by HPLC) as a white solid. $^1$H NMR (300 MHz, DMSO-d$_5$): δ 8.55–8.05 (2H, bm), 7.57.15 (5H, m), 5.40 (2H, bm), 3.0–2.65 (2H, m), 1.45 (9H, s) 1.43–1.10 (2H, m), 0.97 (1H, bm), 0.85 (1H, bm).

EXAMPLE 32

Synthesis of BIO-1115

A. The method described in Procedure C was followed using methyl 3-amino-3-(4-chlorophenyl)-1-propanoate HCl salt (ester M-1, preparation described in procedure B) (68 mg, 0.27 mmol) to afford 1115-1 (94 mg, 0.22 mmol, 82%) as a white foam. $^1$H NMR (CDCl$_3$): δ 7.35 (1H), 7.25–7.10 (4H), 5.35 (1H), 4.95 (1H), 4.05 (1H), 3.60 (1.5H), 3.55 (1.5H), 2.80–2.65 (2H), 1.65 (2H), 1.40 (10H), 0.80 (6H).

B. Compound 1115-1 (68 mg, 0.27 mmol) was treated as described in Example 29B to afford crude 11152 (67 mg, 0.15 mmol, 68%) as a pale yellow solid. $^1$H NMR: δ 7.50 (1H), 7.40–7.00 (9H), 6.20 (1H), 5.25 (1H), 4.45 (1H), 3.60 (1.5H), 3.55 (1.5H), 2.7–2.55 (4H), 1.65–1.40 (3H), 0.80 (6H).

C. A small portion of crude 1115-1 was hydrolysed, purified by LC and the pure fractions collected to afford Bio-1115A (~1 mg) m/z=431 (100% pure by HPLC) along with Bio-1115B (~2 mg) m/z=431 (100% pure by HPLC) as white solids.

Bio-1115A: $^1$H NMR (300 MHz, DMSO-d$_6$): δ 8.46 (1H, d, J=8.2 Hz), 8.27 (1H, d, J=8.2 Hz), 7.46–7.18 (9H, m), 5.20 (1H, m), 4.35 (1H, m), 3.60–3.45 (2H, m), 2.71 (2H, d, J= 7.3 Hz), 1.63 (1H, m), 1.48 (2H, m), 0.91 (3H, d, J=6.4 Hz), 0.84 (3H, d, J=6.4 Hz).

Bio-1115B: $^1$H NMR (300 MHz, DMSO-d$_5$): δ 8.60 (1H, d, J=8 Hz), 8.26 (1H, d, J=8 Hz), 7.45–7.15 (9H, m), 5.18 (1H, m), 4.35 (1H, m), 3.50 (2H, m), 2.70 (2H, m), 1.50 (1H, m), 1.42 (2H, m), 0.85 (3H, d, J=6.3 Hz), 0.75 (3H, d, J=6.3 Hz).

EXAMPLE 33

Synthesis of BIO-1129

A. To a solution of 4-(phenylurea)phenylacetic acid (540 mg, 2.0 mmol; prepared in Example 22C) in DMF (5 mL) was added EDC (460 mg., 2.4 mmol). After stirring at room temperature for 15 min, phenylalanine t-butyl ester HCl salt (515 mg, 2.0 mmol) which was neutralized with excess Hunig's base (0.7 mL, 4.0 mmol) was added in DMF (3 mL). After stirring overnight the reaction was diluted with ethyl acetate (20 mL) and washed with 60% sat. bicarbonate (2×10 mL), citric acid (2×10 mL), brine (2×10 mL), dried over sodium sulfate and concentrated to afford crude 1129-1 (662 mg, 1.40 mmol, 70%) as a thick pale yellow oil. $^1$H NMR (CDCl$_3$): δ 7.45–6.90 (16H), 6.45 (1H), 4.70 (1H), 3.4 (2H), 3.15–2.90 (2H), 1.35 (9H).

B. To crude product 1129-1 (662 mg, 1.40 mmol) was added methylene chloride (5 mL) followed by TFA (1 mL). After stirring overnight the reaction was concentrated to dryness and dried on a vacuum pump. A small portion (21 mg, 0.05 mmol) was dissolved in DMF (1 mL) and HOBt (11 mg, 0.07 mmol) was added followed by EDC (14 mg, 0.06 mmol). After stirring for 15 min at room temperature amine β-3 (13 mg, 0.05 mmol) was added in DMF (0.5 mL). After stirring overnight the reaction was diluted with ethyl acetate (20 mL), washed with sat. bicarbonate (2×10 mL), citric acid (10 mL), brine (10 mL) dried over sodium sulfate and concentrated to afford crude 1129-2 (26 mg, 0.04 mmol, 80%) as a light tan solid. $^1$H NMR (CDCl$_3$): δ 8.4 (1H), 7.4–6.5 (19H), 5.95 (2H), 5.7 (1H), 5.25 (1H), 4.70 (1H), 3.65–3.50 (5H), 3.10–2.65 (4H).

C. A small aliquot of crude 1129-2 was hydrolysed as described in Example 1B and purified by HPLC to afford Bio-1129A (~1.5 mg) m/z=609 (80:20 ds) (100% pure by HPLC) and Bio-1129B (~2 mg) m/z=609 (9:91 ds) (100% pure by HPLC) as white solids.

Bio-1129A: $^1$H NMR (300 MHz, DMSO-d$_5$): δ 8.18 (1H, s), 8.14 (1H, s), 8.50 (1H, bd), 8.23 (1H, bd), 7.50 (2H, d, J=8.1 Hz), 7.40–7.10 (9H, m), 7.08–6.72 (6H, m), 6.04 (2H, s), 5.15 (1H, m), 4.07 (1H, m), 3.38 (2H, m, 3.052.70 (2H, m), 2.62 (2H, s).

EXAMPLE 34

Synthesis of BIO-1131

A. The method of Example 1A was performed using phenylureaphenyl acetic acid (prepared in Example 22C) and isoleucine methyl ester HCl salt (362 mg, 2.0 mmol) (treated with TEA) to afford crude 1131-1 (344 mg, 1.0 mmol, 51%) as a clear thick oil. $^1$H NMR (CDCl$_3$): δ7.7 (1H), 7.35–6.95 (10H), 6.60 (1H) 4.55 (1H), 3.65 (3H), 3.45 (2H), 1.90 (1H), 1.45–1.20 (3H), 0.85 (5H).

B. To a solution of crude 1131-1 (344 mg, 0.95 mmol) in methanol (5 mL) was added 2N LiOH (2 mL). After stirring overnight the methanol was removed, H$_2$O (5 mL) added and the pH adjusted to pH=1–2. The aqueous layer was extracted with ethyl acetate (5×20 mL) dried over sodium sulfate and concentrated to give 1131-2 (365 mg, 0.95 nmol, 100%) as a tan solid. $^1$H NMR (CDCl$_3$): δ 8.70 (2H), 8.30 (1H), 7.60–7.20 (8H), 7.00 (1H), 4.25 (1H), 3.55 (2H), 1.90 (1H), 1.55 (1H), 1.30 (2H), 0.85 (5H).

C. Prepared from 1131-2 (27 mg, 0.07 mmol) and amine β-3 (11 mg, 0.07 mmol) as described in Example 1A to afford crude 1131-3 (34 mg, 89%), as a pale brownish solid. $^1$H NMR(CDCl$_3$): δ 8.3 (2H), 7.45–6.65 (16H), 5.45 (1H), 4.45–4.30 (1H), 3.55 (2H), 3.2–2.90 (2H), 2.00–0.70 (9H).

D. A small aliquot of crude 1131-3 was hydrolysed as described in Example 1B and purified by HPLC to afford Bio-1131A (~2 mg)m/z=531 (100:0 ds) (100% pure by HPLC) and Bio-1131B (~3 mg) m/z=531 (0:100 ds) (100% pure by HPLC) as white solids.

Bio-1131A: $^1$H NMR (300 MHz, DMSO-d$_6$): δ 8.69 (1H, s), 8.63 (1H, s), 8.50 (1H, d, J=8.1H$_z$), 7.50 (2H, d, J=7.8H$_z$), 7.44–7.22 (8H, m), 7.19 (2H, d, J=8.4H$_z$), 7.00 (1H, m), 5.27 (1H, m), 4.36 (1H, m), 3.52 (2H, m), 3.00 (2H, bm), 2.71 (2H, d, J=7.3H=), 1.70 (1H, bm), 1.44–1.26 (1H, m), 1.22–1.00 (3H, m), 0.95–0.78 (5H, m).

Bio-1131B: $^1$H NMR (300 MHz, DMSO-d$_6$): δ 8.73 (1H, s), 8.68 (1H, s), 8.60 (1H, d, J=8 Hz), 8.15 (1H, d, J=8 Hz), 7.50 (2H, d, J=7.9 Hz), 7.42 (2H, d, J=8.4 Hz), 7.37–7.23 (5H, m), 7.20 (2H, d, J=8.4 Hz), 7.00 (1H, m), 5.35 (1H, m), 4.23 (1H, m), 3.50 (2H, m), 3.05 (2H, bm), 2.71 (2H, m), 1.72 (1H, bm), 1.20 (3H, m), 0.72–0.60 (5H, m).

EXAMPLE 35

Synthesis of BIO-1136

A. The method described in Example 1A was performed utilizing commercially available N-BOC-S-benzyl-cysteine (25 mg, 0.08 mmol) and methyl 3-amino-3-phenyl-1-propanoate (17 mg, 0.09 mmol) to afford crude protected amine 1136-1 (42 mg, 0.08 mmol, 100%). $^1$H NMR (CDCl$_3$): δ 7.35 (10H), 5.40–5.20 (2H), 4.20 (1H), 3.65 (1.5H), 3.55 (1.5H), 3.54 (1.5H), 3.25–2.65 (6H), 1.45I.30 (9H).

B. The protected amine 1136-1 was treated as described in Procedure D to give the TFA-amine salt 1136-2.

C. The method described in Example 22D was performed utilizing free amine 1136-2 (42 mg, 0.08 mmol) (TEA treatment) to afford crude 1136-3 which was used in the hydrolysis step without further purification.

D. A small aliquot of crude 1136-3 was hydrolysed as described in Example 1B and purified by HPLC to afford Bio-1136 (~4 mg)m/z=611 (100% pure by HPLC) as a white solid. $^1$H NMR (300 MHz, DMSO-d$_5$): δ 9.05 (2H, bm), 8.90 (1H, br), 8.37 (1H, br), 7.50 (1H, d, J=7.7 Hz), 7.45 (1H, d, J=8.3 Hz), 7.4–7.2 (9H, m), 7.00 (1H, m) 5.25 (1H, br), 4.65 (1H, br), 3.5–3.2 (4H, m), 2.70 (2H, bm).

EXAMPLE 36

Synthesis of BIO-1176

A. To a solution of commercially available N-BOC-aspartic acid α-benzyl ester (500 mg, 1.55 mmol) in DMF (5 mL) was added HOBt (283 mg, 2.10 mmol) followed by EDC (343 mg, 1.80 mmol). After stirring for 15 minutes at room temperature thiomorpholine (500 mg, 1.54 mmol) was added followed by Hunig's base (0.7 mL, 92 mmol) and the reaction mixture stirred at room temperature overnight. The reaction was worked up by diluting with ethyl acetate (25 mL) and washing with 60% sat. bicarbonate (5 mL), 5% citric acid (5 mL) and brine (5 mL). The organics were separated, dried over sodium sulfate and concentrated to give ester 1176-1 as a thick orange oil (421 mg, 1.03 mmol, 69%). $^1$H NMR (CDCl$_3$): δ 7.13 (5H, m), 5.69 (1H, bd, J=9.4 Hz) 5.03 (1H, d, J=12.6H$^z$), 4.42 (1H, m), 3.61 (1H, m), 3.60–3.40 (4H, m), 2.96 (1H, bm), 2.58 (1H, bm), 2.35 (4H, m) 1.22 (9H, s)

B. Ester 1176-1 (100 mg, 0.25 mmol) was treated as described in Example 1B to afford acid 1176-2 (76 mg, 0.24 mmol, 96%) as a clear thick oil. $^1$H NMR (CDCl$_3$): δ 7.39–7.28 (5H, m), 7.15–6.70 (1H, br), 5.70 (1H, bs, J=6.3 Hz), 4.55 (1H, br), 4.40–3.40 (4H, m) 3.15 (1H, m), 2.80–2.52 (5H, m), 1.43 (9H, s).

C. The method of Example 1A was performed using acid 1176-2 (32 mg, 0.10 mmol), in DMF, HOBT, EDC, and amine β-3 to afford 1176-3 (36 mg, 0.07 mmol, 70%) as a thick pale yellow oil. $^1$H NMR (CDCl$_3$): δ 7.71 (1H, br), 6.61 (3H, m) 6.00 (0.5H, br), 5.90 (1H, s), 5.77 (0.5H, br), 5.21 (1H, m), 4.51 (1H, bm), 3.90–3.40 (4H, m), 3.39 (3H, s), 3.12–3.00 (1H, m), 2.85–2.65 (3H, m), 2.63–2.45 (4H, m), 1.43 (4.5H, s), 1.43 (4.5H, s).

D. The protected amine 1176-3 (36 mg, 0.07 mmol) was treated as described in Procedure D to give TFA-amine salt 1176-4 (51 mg, 0.07 mmol, 100%) as a pale yellow solid.

E. The method described in Example 22D was performed utilizing free amine 1176-4 (42 mg, 0.08 mmol) (after TEA treatment) to afford crude 1176-5 which was used in the hydrolysis step without further purification.

$^1$H NMR (CDCl$_3$): δ 7.95–6.9 (13H, m), 6.61 (3H, s), 5.85 (2H, s) 5.23 (1H, m), 4.88 (1H, m), 3.89–3.60 (4H, s), 3.55 (3H, s), 3.43 (2H, br), 3.11–2.96 (2H, m), 2.71 (2H, m), 2.46 (4H, m).

F. Crude 1176-5 was hydrolyzed as described in Example 1B and injection of a small aliquot into the HPLC afforded Bio-1176 (~4 mg) m/z=662 (>99% pure by HPLC) as a white solid. $^1$H NMR: (DMSO-d$_6$) δ 8.69 (2H, d, J=9.8 Hz), 8.33 (1H, d, J=8.0 Hz), 8.26 (1H, d, J=8.0 Hz), 7.61 (2H, d, J=8.0 Hz), 7.43 (2H, d, J=8.0 Hz), 7.34 (2H, m), 7.21 (2H, d. J=8.0 Hz), 7.10–6.95 (4H, m), 6.11 (2H, s), 5.13 (1H, m), 4.68 (1H, m), 3.71 (4H, br), 3.56–3.18 (2H, m), 2.73–2.46 (8H, m).

EXAMPLE 37

Synthesis of BIO-1177

A. The procedure described in Example 36A was carried out using methylpropargylamine in place of thiomorpholine to afford crude 1177-1 (374 mg, 0.99 mmol, 66%) as a white foam. $^1$H NMR (CDCl$_3$): δ 7.20 (5H), 5.25 (1H), 5.10 (2H), 4.45 (1H), 4.15–3.8 (2H), 3.15–2.65 (5H), 2.2–2.15 (1H), 1.30 (9H).

B. Crude 1177-1 was treated as described in Example 1B to afford acid 1177-2 (76 mg, 0.26 mmol, 96%) as a clear oil. $^1$H NMR (CDCl$_3$): δ 5.35 (1H), 4.55 (1H), 4.35–3.8 (2H), 3.30–2.65 (5H), 2.4–2.25 (1H), 1.45 (9H).

C. The method of Example 1A was performed using acid 1177-2 (76 mg, 0.26 mmol), in DMF, HOBT, EDC, and amine β-3 to afford crude 1177-3 (78 mg, 0.15 mmol) as a white foam. $^1$H NMR (CDCl$_3$): δ 7.70 (1H), 7.35 (3H), 6.65 (2H), 5.80 (1H) 5.30–5.00 (2H), 4.60 (1H), 4.45–3.80 (2H), 3.60 (3H), 3.30–2.70 (5H), 2.30 (1H), 1.45 (4.5H), 1.40 (4.5H).

D. The protected amine 1177-3 (78 mg, 0.15 mmol) was treated as described in Procedure D to afford TFA-amine salt 1177-4.

E. The method described in Example 22D was performed utilizing free amine 1177-4 to afford 1177-5 (52 mg, 0.08 mmol, 77%) as a tan solid. $^1$H NMR: (CDCl$_3$) δ 7.5–6.9 (14H), 6.65 (3H), 5.85 (2H) 5.25–5.00 (2H), 4.85 (1H), 4.25–3.70 (2H), 3.60 (3H), 3.55 (2H), 3.302.65 (5H), 2.22 (1H).

F. A small portion of 1177-5 was hydrolyzed as described in Example 1B to afford Bio-1177 (~2 mg) m/z=628 (100% pure by HPLC) as a white solid. $^1$H NMR: (DMSO-d$_6$) δ 8.64 (2H, bd), 8.27 (2H, bm), 7.55–7.13 (7H, m), 7.11–6.75 (3H, m) 6.15 (2H, s), 5.12 (1H, bm), 4.65 (1H, bm), 4.25 (2H, bm), 3.25 (2H, m), 3.05 (2H, br) 2.88 (1H, bm), 2.62 (2H, m).

EXAMPLE 38

Synthesis of BIO-1214

A. The procedure described in Example 36A was carried out on the N-BOC-aspartic acid α-benzyl ester (1.60 g, 4.9 mmol) using dimethylamine in place of thiomorpholine to afford ester 1214-1 (1.43 g, 4.1 mmol, 83%) as a thick colorless oil. $^1$H NMR (CDCl$_3$): δ 7.32 (5H, m), 5.85 (1H, br), 5.15 (2H, m) 4.55 (1H, br), 3.12 (1H, m), 2.94 (3H, s), 2.88 (3H, s), 2.73 (1H, m), 1.40 (9H, s).

B. Ester 1214-1 (124 mg, 0.33 mmol) was dissolved in ethyl acetate (2 mL) and 10% Pd/C (~50 mg) was added and the mixture was hydrogenated under pressure (40 psi) for 2 h. The reaction was filtered through Celite® and concentrated to afford acid 1214-2 (95 mg, 0.33 mmol, 100%), as a colorless oil. $^1$H NMR: (CDCl$_3$) δ 5.81 (1H, bm), 4.48 (1H, bs), 3.15 (1H, m), 3.00 (3H, s), 2.93 (3H, s), 2.59 (1H, m), 1.39 (9H, s).

C. The method of Example 1A was performed using acid 1214-2 (28 mg, 0.10 mmol) and amine β-3 (17 mg, 0.80 mmol) to afford protected amine 1214-3 (55 mg, 0.10 mmol, 100%) as a white foam. $^1$H NMR: (CDCl$_3$) δ7.77 (1H, bd), 6.71 (3H, m), 6.11 (1H, bd), 5.91 (2H, s) 5.25 (1H, m), 4.51 (1H, br), 3.60 (3H, s), 3.12 (1H, m), 2.94 (3H, s), 2.90 (3H, s), 2.88–2.68 (2H, m), 2.48 (1H, m), 1.43 (9H, s).

D. The protected amine 1214-3 (55 mg, 0.10 mmol) was treated as described in Procedure D to afford TFA-amine salt 1214-4.

E. The method described in Example 22D was performed utilizing free amine 1214-4 to afford 1214-5 (31 mg, 0.05 mmol, 50%) as a tan solid. $^1$H NMR (CDCl$_3$): δ 7.45–6.90 (13H, m), 6.61 (3H, m), 5.85 (2H, s), 5.24 (1H, m), 4.82 (1H, m), 3.55 (3H, s), 3.47 (2H, m), 3.082.94 (1H, m), 2.92 (3H, s), 2.84 (3H, s), 2.77–2.50 (2H, m), 2.45 (1H, m).

F. A small portion of 1214-5 was hydrolyzed as described in Example 1B to afford BIO-1214 (~2 mg) m/z=604 (100% purity by HPLC) as a white solid.

EXAMPLE 39

Synthesis of BIO-1215

A. To a solution of amide 1214-1 (prepared in Example 38A) (671 mg, 1.9 mmol) in dry tetrahydrofuran (5 mL) cooled to 0° C. was added 1 N BH$_3$/THF solution (4.1 mL, 3.8 mmol) dropwise. After stirring the reaction mixture for 2 h at room temperature the reaction was quenched with methanol (2 mL) and concentrated to dryness. Methanol (5 mL) was added and removed three times to remove all (MeO)$_3$B formed. Drying under high vacuum afforded amine 1215-1 (623 mg, 1.7 mmol, 90%) as a thick colorless oil. $^1$H NMR (CDCl$_3$) δ 7.38 (5H, m), 5.48 (1H, bm), 2.65–2.35 (8H, m), 1.95 (2H, m), 1.42 (9H, s).

B. Amine 1215-1 (124 mg, 0.34 mmol) was subjected to catalytic hydrogenation using methanol/ethyl acetate/acetic acid as solvent and 10% Pd/C (~50 mg). After 2 h the reaction mixture was filtered and concentrated to give acid 1215-2 (90 mg, 0.33 mmol, 97%) as a thick colorless oil. $^1$H NMR (CDCl$_3$) δ 5.91 (1H, br), 3.95 (1H, br), 3.54 (1H, bm), 2.71–2.42 (8H, m), 2.15 (2H, br), 1.33 (9H, s).

C. The method of Example 1A was performed using acid 1215-2 (55 mg, 0.12 mmol) and the amine β-3 (22 mg, 0.10 mmol) to afford protected amine 1215-3 (44 mg, 0.09 mmol, 90%) as a white foam.

$^1$H NMR(CDCl$_3$) δ 6.75 (3H, m), 6.51 (1H, bd), 5.91 (2H, s), 5.30 (1H, m), 4.37–4.12 (2H, m), 3.61 (3H, s), 2.902.65 (2H, m), 2.55–2.00 (10H, m), 1.42 (9H, s).

D. The protected amine 1215-3 (44 mg, 0.09 mmol) was treated as described in Procedure D to afford TFA-amine salt 1215-4.

E. The method described in Example 22D was performed utilizing free amine 1215-4 to afford 1215-5 (38 mg, 0.06 mmol, 70%) as a white solid. $^1$H NMR (CDCl$_3$) δ 7.41–6.90 (13H, s), 6.71 (3H, m), 5.91 (2H, s), 5.29 (1H, m), 4.21 (1H, m), 3.61 (3H, s), 3.45 (2H, m), 2.902.70 (2H, m), 2.40–1.95 (10H, m).

F. A small portion of 1214-5 was hydrolyzed as described in Example 1B to afford BIO-1215 (~3 mg) m/z=590 (100% pure by HPLC) as a white solid.

EXAMPLE 40

Synthesis of BIO-1227

A. The method as described in Example 1B was performed using commercially available BOC-S-methylcysteine (28 mg, 0.12 mmol) and amine β-3 (21 mg, 0.10 mmol) to afford protected amine 1227-1 (32 mg, 0.07 mmol, 70%) as a white foam. $^1$H NMR (CDCl$_3$) δ 7.38 (1H, bd), 6.81–6.67 (3H, m), 5.90 (2H, s), 5.40 (1H, bd), 5.37 (1H, m), 4.20 (1H, m), 3.59 (3H, s), 2.95–2.68 (4H, m), 2.10 (3H, s), 1.43 (9H, s).

B. The protected amine 1227-1 (32 mg, 0.07 mmol) was treated as described in Procedure D to afford TFA-amine salt 1227-2.

C. The method described in Example 22D was performed utilizing free amine 1227-2 and the 2-methylphenylureaphenylacetic acid (28 mg. 0.10 mmol) to afford crude ester 1227-3 (29 mg, 0.047 mmol, 67%) as a light tan solid. $^1$H NMR (CDCl$_3$) δ 7.62 (1H, bd), 7.46.9 (12H, m), 6.80 (3H, m) 5.90 (2H, s) 5.15 (1H, m), 4.45 (1H, m), 3.63–3.45 (5H, m), 3.15–2.61 (4H, m), 2.21 (3H, s), 2.10 (3H, s).

D. A small aliquot of crude ester 1227-3 was hydrolyzed as described in Example 1B to afford BIO-1227 (~4 mg) m/z=593 (>99% pure by HPLC) as a white solid. $^1$H NMR (DMSO-d$_6$): δ 9.01 (1H, s), 8.67 (1H, d, J=7.9 Hz), 8.31 (1H, d, J=8.3 Hz), 7.97 (1H, s), 7.90 (1H, d, J=8 Hz), 7.44 (2H, d, J=8.3 Hz), 7.23 (4H, m), 6.99 (2H, m), 6.85 (2H, m), 6.03 (2H, s), 5.16 (1H, m), 4.54 (1H, m), 3.39 (2H, m), 2.81–2.58 (4H, m) 2.30 (3H, s), 2.05 (3H, s).

EXAMPLE 41

Synthesis of BIO-1149

A. To a solution of the product from Procedure C (272 mg, 0.67 mmol) in CH$_2$Cl$_2$ (2.5 ml) was added TFA (2.5 ml) slowly and the mixture was stirred at room temperature for 1 h. The solvents were removed to give an oil. This oil was dissolved in CH$_2$Cl$_2$ (2.5 ml). To this solution was added Et$_3$N to pH 9 and then succinimidyl 2-quinolinecarboxylic acid (170 mg, 0.63 mmol). The mixture was stirred at room temperature for 1 h followed by usual workup (5% citric acid, 5% NaHCO$_3$ and sat. NaCl) to afford ester 1149-1 (200 mg, 76%) as a white solid.

B. Compound 1149-1 (200 mg, 0.43 mmol) was dissolved in methanol (1.5 ml) and to the solution was added 1M aqueous LiOH (0.5 ml). The mixture was stirred at room temperature for 3 h and neutralized with 5% citric acid to pH 3 and was extracted with EtOAc (3×5 ml). The combined extracts were dried (Na$_2$SO$_4$) and concentrated to afford 155 mg (82.5%) crude 1149. A small amount of the crude product (30 mg) was purified by HPLC to give BIO-1149, and the diastereomers were separated. HPLC: Retention time; A: 36 min; B:38 min. FAB-MS=434. $^1$H NMR: (CDCl$_3$, 300 MHz, ppm) 8.72 (m, 1H), 8.30–7.98 (m, 3H), 7.82–7.64 (m, 2H), 7.60–7.51 (m, 1H), 7.30–7.09 (m, 5H), 5.46–5.38 (m, 1H), 4.86–4.72 (m, 1H), 2.92–2.74 (m, 2H), 1.88–1.61 (m, 3H), 0.96–0.83 (m, 6H).

EXAMPLE 42

Synthesis of BIO-1152

A. To a solution of the product of Procedure D2 (33 mg, 0.1 mmol) in CH$_2$Cl$_2$ (0.5 ml) was added 2,2-dimethylbutyric acid chloride (14 mg, 0.1 mmol) and Et$_3$N (50 μl). The mixture was stirred at room temperature for 16 h. The usual workup (5% NaHCO$_3$, 5% citric acid and sat. NaCl) afforded 1152-2 (37 mg, 76%) as a white solid. $^1$H NMR: (CDCl$_3$, 300 MHz, ppm) 7.32–7.19 (m, 5H), 6.08 (s, 1H), 5.36–5.27 (m, 1H), 4.53–4.44 (m, 1H), 2.86–2.61 (m, 2H), 2.05 (s, 2H), 1.26 (s, 9H), 1.01 (s, 9H), 0.99–0.84 (s, 9H).

B. Ester 1152-2 was dissolved in CH$_2$Cl$_2$ (2.5 ml) and TFA (2.5 ml) and stirred at room temperature for 3 h to afford an oil. The purification of the oil by HPLC to give a pure BIO-1152. $^1$H NMR: (CDCl$_3$, 300 MHz, ppm) 8.29 (d, 1H), 7.44 (d, 1H), 7.34–7.18 (m, 5H), 5.44–5.32 (m, 1H), 4.78–4.69 (m, 1H), 3.21–3.14 (m, 2H), 2.98–2.77 (dd, 2H), 1.59–1.38 (m, 3H)$_1$ 0.96 (s, 9H), 0.84 (d, 3H), 0.73 (d, 3H).

EXAMPLE 43

Synthesis of BIO-1089

A. To a solution of amine β-6 (2.2 g, 8.76 mmol) in CH$_2$Cl$_2$ (25 ml) was added N-BOC-methionine succinimidyl ester (2.77 g, 8.0 mmol) and Et$_3$N (5 drops) and the mixture was stirred at room temperature for 1.5 h. The mixture was washed with 5% citric acid (2×10 ml), 5% NaHCO$_3$ (2×10 ml) and sat. NaCl (15 ml), dried (Na$_2$SO$_4$) and concentrated to give 1089-1 (3.2 g, 83%) as a white solid. $^1$H NMR: (CDCl$_3$, 300 MHz, ppm) 7.27 (d, 2H), 6.81 (d, 2H), 5.31–5.20 (m, 2H), 4.38–4.28 (m, 1H), 3.72 (s, 3H), 2.82–2.64 (m, 2H), 2.12 (s, 3H), 1.44 (s, 9H), 1.30 (s, 9H).

B. To a solution of 1089-1 (3.2 g, 6.64 mmol) in EtOAc (15 ml) was added a 1M HCl-EtOAc solution (40 ml) and the mixture was stirred at room temperature for 4.5 h. The reaction mixture was quenched with H$_2$O (60 ml) and the aqueous layer was collected. It was neutralized with solid NaHCO$_3$ to pH 8 and was extracted with EtOAc (2×45 ml). The combined organic extracts were washed with sat. NaCl (20 ml), dried (Na$_2$SO$_4$) and concentrated to afford 1089-2 (1.7 g, 67%) as an oil. $^1$H NMR: (CDCl$_3$, 300 MHz, ppm) 7.98 (d, 1H), 7.19 (d, 2H, J=8.3 Hz), 6.81 (d, 2H, J=8.3 Hz), 5.32–5.18 (m, 1H), 3.74 (s, 3H), 3.48–3.44 (m, 1H), 2.82–2.62 (m, 2H), 2.53 (t, 2H), 2.182.06 (m, 1H), 2.04 (s, 3H), 1.8–1.66 (1H), 1.31 (s, 9H).

C. The method of Example 22D was performed using 1089-2 (1.7 g, 4.45 mmol) to afford 1089-3 (2.3 g, 81.6%) as a solid. This material was used in the next step without further purification. $^1$H NMR: (DMSO-d$^6$, 300 MHz, ppm) 8.60 (d, 2H), 8.41 (d, 1H), 8.24 (d, 1H), 7.44 (d, 2H), 7.31(d, 2H), 7.1–6 (t, 2H), 7.13 (t, 2H), 6.91 (t, 1H), 6.79 (d, 2H), 5.10–5.01 (m, 1H), 4.36–4.33 (m, 1H), 3.68 (s, 3H), 3.29 (s, 2H), 2.61–2.58 (m, 2H), 1.89 (s, 3H), 1.26 (s, 9H).

D. Compound 1089-3 (2.3 g, 3.63 mmol) was dissolved in 4N HCl-dioxane (8 ml) and the solution was stirred at room temperature for 16 h. After the dioxane was removed, ether (15 ml) was added and mixture was stirred for 10 min. The precipitate was collected and was recrystallized from methanol to give pure BIO-1089 as a pale brown solid. FAB-MS=579. $^1$H NMR: (DMSO-d$^6$, 300 MHz, ppm) 8.76 (d, 2H), 8.52 (d, 1H), 7.54 (d, 2H), 7.46 (d, 2H), 7.36 (t, 1H), 7.34–7.26 (m, 4H), 7.04 (t, 1H), 6.95 (d, 2H), 5.22–5.20 (m, 1H), 4.46–4.35 (m, 1H), 3.81 (s, 3H), 3.50, (s, 2H), 3.20 (m, 2H), 2.79–2.73 (m, 2H), 2.35 (t, 2H), 2.03 (s, 3H), 1.87–1.80 (m, 2H).

EXAMPLE 44

Synthesis of BIO-1090

A. The method described in Procedure C was followed using amine β-10 (28 mg, 1.0 mmol) to afford 1090-1 (38 mg, 84%) as a white solid. $^1$H NMR: (CDCl$_3$, 300 MHz, ppm) 7.08 (m, 1H), 6.82 (s, 1H), 6.74–6.70 (m, 2H), 5.24–5.15 (m, 1H), 4.98–4.93 (m, 1H), 4.16–4.13 (m, 4H), 2.74–2.53 (m, 2H), 1.62–1.42 (m, 3H), 1.44 (s, 9H), 1.40 (s, 9H), 0.89 (m, 6H).

B. The white solid of 1090-1 (38 mg, 0.77 mmol) was treated as described in Procedure D1 to give 1090-2 as an oil. This compound was used in next step without further purification. $^1$H NMR: (CDCl$_3$, 300 MHz, ppm) 7.24–7.15 (m, 2H), 6.84–6.61 (m, 3H), 5.81–5.78 (m, 1H), 4.23 (s, 4H), 4.19–4.08 (m, 1H), 2.88–2.62 (m, 2H), 1.70–1.46 (m, 3H), 0.90–0.81 (m, 6H).

C. The method of Example 22D was performed using amine 1090-2 to afford crude 1090 (27 mg, 59%). The purification of crude product by HPLC gave pure BIO1090 as a white solid. FAB-MS=603.

EXAMPLE 45

Synthesis of BIO-1194

A. To a well-stirred cold solution of methyl p-aminophenylacetate (9.8 g, 59.4 mmol) in CH$_2$Cl$_2$ (200 ml) and Et$_3$N (25 ml, 18 g, 178.2 mmol) was added COCl$_2$ (96 ml of 1.9M solution in toluene) through an additional funnel for 1 h. The reaction mixture was stirred at 0° C. for another 1 h. The reaction mixture was concentrated and ether: pet ether (3:1) (125 ml) was added. The solid was filtered and the filtrate was collected. Removal of the solvents gave crude 1194-1 as a brown liquid. The purification of crude product by distillation (118120° C./10 mm) gave pure 1194-1 (8.5 g, 75%) as a colorless liquid. $^1$H NMR: (CDCl$_3$, 300 MHz, ppm) 7.20 (d, J=8.4 Hz), 7.02 (d, J=8.4 Hz), 3.69 (s, 3H), 3.48 (s, 2H).

B. To a solution of 1194-1 (5.73 g, 30.0 mmol) in CH$_2$Cl$_2$ (60 ml) was added 2-aminopyridine (2.82 g, 30 mmol) in portions. The mixture was stirred at room temperature for 0.5 h then 35° C. for 0.5 h. The resulting mixture was diluted with pet ether (60 ml) and a white solid was formed. Filtration of the solid gave pure 1194-2 (8.35 g, 98%) as a white solid. $^1$H NMR: (CDCl$_3$, 300 MHz, ppm): 8.20 (s, 2H), 7.62–7.51 (m, 3H), 7.33 (d, 2H), 7.01 (d, 2H), 6.89–6.85 (m, 1H), 3.70 (s, 3H), 3.59 (s, 2H).

C. Compound 1194-2 (5.7 g, 20.0 mmol) was dissolved in methanol (20 ml) and to this was added 1N NaOH (40 ml). The mixture was heated until a clear solution was formed and was stirred at room temperature for 16 h, followed by a careful neutralization with 1N HCl to pH 7 then with acetic acid to pH 3. The white solid thus formed was filtered and washed with methanol (15 ml) and ether (2×30 ml) to give 1194-3 (4.7 g, 87%) as a white powder. $^1$H NMR: (DMSO-D$^6$, 300 MHz, ppm) 10.62 (br, s, 1H), 9.53 (br, s, 1H), 8.39 (d, 1H), 7.82 (t, 1H), 7.63–7.55 (m, 1H), 7.33–7.27 (d, 2H), 7.14–7.08 (m, 1H), 3.62 (s, 3H).

D. Standard Procedure C was followed to prepare 1194-4 by coupling amine β-6 (2.65 g, 10.56 mmol) with BocLeuOSu (3.28 g, 10 mmol) in CH$_2$Cl$_2$ (25 ml) and Et$_3$N (5 drops) then followed by deprotection (TFA/CH$_2$Cl$_2$) to afford 1194-4 (4.5 g, 83.6%) in two steps. 1194-4-Boc: $^1$H NMR: (CDCl$_3$, 300 MHz, ppm) 7.18 (d, 2H), 6.36 (d, 2H), 5.13–5.10 (m, 1H), 4.12–4.01 (m, 1H), 3.72 (s, 3H), 2.79–2.60 (m, 2H), 1.62–1.40 (3H), 1.38 (s, 9H), 1.26 (s, 9H), 0.85–0.80 (m, 6H).

1194-4: $^1$H NMR: (CDCl$_3$, 300 MHz, ppm) 7.10 (d, 2H), 6.78 (d, 2H), 5.43–5.27 (m, 1H), 4.21–4.06 (m, 1H), 3.71 (s, 3H), 2.95–2.76 (m, 1H), 2.75–2.56 (m, 1H), 1.62–1.32 (m, 6H).

E. The method of Example 1A was followed using acid 1194-3 (1.36 g, 5.0 mmol) and amine 1194-4 to afford crude BIO-1194 (2.1 g, 78%) as a white solid. The pure product (purity>97.5%) was obtained by crystallization from methanol. $^1$H NMR: (CDCl$_3$, 300 MHz, ppm) 8.03–7.97(m, 2H), 7.59 (m, 1H), 7.51 (d, 2H), 7.18–7.07 (m, 4H), 6.27 (d, 2H), 5.24 (m, 1H), 4.39–4.36 (m, 1H), 3.61 (s, 3H), 3.43 (s, 2H), 2.69–2.66 (m, 2H), 1.54–1.33 (m, 2H), 0.860.75 (m, 6H).

EXAMPLE 46

Synthesis of BIO-1180

A. The method described in Example 45A was followed using t-butyl p-aminophenylacetate to give 1180-1 in 94% yield. FAB-MS=234. $^1$H NMR: (CDCl$_3$, 300 MHZ, ppm) 7.18 (d, 2H, J=8.2 Hz), 6.98 (d, 2H, 8.2 Hz), 3.49 (s, 3H), 1.45 (s, 9H).

B. To a solution of isocyanate 1180-1 (233 mg, 1.0 mmol) in CH$_2$Cl$_2$ (5 ml) was added 2-aminothiazole (100 mg, 1.0 mmol) and the mixture was heated until a clear solution was formed and was stirred at room temperature for 1 h. Removal of the solvents gave 1180-2 (335 mg) as a brown-yellow solid. This solid was dissolved in CH$_2$Cl$_2$ (2.5 ml), and to this was added TFA (2.5 ml). The mixture was stirred at room temperature for 1.5 h and was concentrated to afford 1180-3 (300 mg) as a yellow solid. FAB-MS=278.

C. To a solution of 1180-3 (28 mg, 0.1 mmol) in DMF (0.25 ml) was added EDC (60 mg, 0.31 mmol) and DMAP (55 mg). The mixture was stirred at room temperature for 10 min. and to this was added amine-TFA salt P-3 (23 mg, 0.051 mmol). The resulting reaction mixture was stirred at room temperature for 16 h. The usual workup (5% citric acid, 5% NaHCO$_3$, sat. NaCl) drying (Na$_2$SO$_4$), and concentration gave crude 1180-4 (22 mg, 72%). FAB-MS=596.

D. The crude 1180-4 was hydrolyzed as described in Example 1B to give crude Bio-1180. Purification of the crude product by HPLC afforded pure BIO1180. HPLC: retention time: 26.3 min.>99% purity. FAB-MS=582. $^1$H NMR: (DMSO-D$^6$, 300 MHz, ppm) 9.00 (br, s 1H), 8.52 (d, 2H, J=8.3 Hz), 8.24 (d, 2H, J=8.3 Hz), 7.50–7.47 (m, 3H), 7.28 (d, 2H, J=8.5 Hz), 7.20 (1H, d, J=3.5 Hz), 6.95–6.81 (m, 3H), 6.08 (d, 1H, J=1.4), 5.19–5.16 (m, 1H), 4.4–4.2 (m, 1H), 3.51 (dd, J=14.1 Hz and 23.8 Hz), 2.76–2.65 (m, 1H), 1.57–1.50 (m, 1H), 1.501.44 (m, 2H), 0.92 (d, 2H, J=6.3 Hz), 0.86 (d, J=6.3 Hz).

EXAMPLE 47

Synthesis of BIO-1199

To a solution of BIO-1089 (15 mg) in DMSO (1.0 ml), H$_2$O (2 ml) was added Oxone® (20 mg) and the mixture was stirred at room temperature. The HPLC trace showed that Bio-1089 (Retention time=20 min) was disappearing and a new peak (Retention time=16.9 min) was forming. After stirring at room temperature for 16 h, the starting Bio-1089 was almost totally consumed. Bio-1199 (retention time=16.9 min) was isolated by HPLC and was >99% pure. FAB-MS=595.

EXAMPLE 48

Synthesis of BIO-1207

A. Procedure C was carried out using amine β-5 (220 mg, 1.053 mmol), this product was then subjected to the conditions descibed in Procedure D1 to afford 1207-1 (383 mg, 88% for two steps).

B. The method of Example 1A was followed using p-Cbz-aminophenylacetic acid (260 mg, 0.91 mmol) and amine 1207-1 (375 mg, 0.86 mmol) (treated with Et$_3$N) afford 1207-2 (415 mg, 82%) as a pale brown solid.

C. Compound 1207-2 (390 mg, 0.66 mmol) was deprotected as described in Procedure D2 to afford 1207-3 (140 mg, 47%) as a pale brown solid.

D. To a solution of 2-isopropylaniline (135 mg, 1.0 mmol) in CH$_2$Cl$_2$ (2 ml) and Et$_3$N (0.5 ml) was added COCl$_2$ (1.6 ml of 1.9 M solution in toluene, 3.0 mmol) solution at 0° C. slowly and the resulting mixture was stirred at room temperature for 1 h and diluted with ether (15 ml). Removal of the solid thus formed and the solvents gave 1207-4 (165 mg) as a brown liquid. $^1$H NMR: (CDCl$_3$, 300 MHz, ppm) 7.87–7.64 (m, 4H), 3.83–3.74 (m, 1H), 1.81 (d, 6H).

E. To a solution of 1207-4 (12 mg, 0.074 mmol) in DMF (0.12 ml) was added 1 drop of Et$_3$N and 1207-3 (28 mg, 0.062 mmol). The resulting mixture was stirred for 1 h (FAB-MS=617) and was added to methanol (2 ml) and 2M LiOH (0.25 ml). This mixture was stirred at room temperature for 16 h and was subjected to HPLC. The pure fractions were collected and concentrated to afford BIO1207 as a white solid. FAB-MS=603. HPLC: retention time=31.2 min; >98.5% purity.

EXAMPLE 49

Synthesis of BIO-1210

The procedure described in Example 22D was followed using 2-methylphenylureaphenylacetic acid and the free amine of the TFA-amine salt prepared in Example 44B (65 mg). The resulting product was subjected to HPLC. The pure fractions were collected and concentrated to afford BIO-1210 as a white solid. FAB-MS=603. HPLC: retention time=28.6 min, >99% purity.

EXAMPLE 50

Synthesis of BIO-1224

A. Procedure C was performed using amine β-4 (48 mg, 0.2 mmol) to afford 1224-1 (82 mg, 91%) as a white solid. $^1$H NMR: (CDCl$_3$, 300 MHz, ppm) 7.49–7.39 (1H), 6.73–6.62 (m, 3H), 5.35–5.28 (m, 1H), 5.19–5.06 (m, 1H), 4.16–4.08 (m, 1H), 3.74 (s, 3H), 3.69 (s, 3H), 2.72–2.51 (m, 2H), 2.40–2.36 (m, 2H), 1.98–1.75 (m, 2H), 1.90 (s, 3H), 1.28 (s, 9H), 1.19 (s, 9H).

B. Compound 1224-1 (60 mg, 0.13 mmol) was dissolved in $CH_2Cl_2$ (1.5 ml) and TFA (1.5 ml). The mixture was stirred at room temperature for 5 h and the solvents were removed to give 1224-2 as a TFA salt. This compound was used in the next step without purification. $^1H$ NMR: ($CDCl_3$, 300 MHz, ppm) 7.92 (br, 1H), 6.82–6.78 (m, 3H), 5.44–5.26 (m, 1H), 4.40–4.28 (m, 1H), 3.84–3.72 (m, 6H), 2.92–2.70 (m, 4H), 2.60–2.25 (m, 2H), 1.92 (s, 3H).

C. The method described in Example 22D was followed using 2-methylphenylureaphenylacetic acid (37 mg, 0.13 mmol) and amine 1224-2 (0.13 mmol). The resulting product was subjected to HPLC. The pure fractions were collected and dried to afford BIO-1224 as a white solid. FAB-MS=623. HPLC: retention-time=23.8 min, >99% purity. $^1H$ NMR: ($CDCl_3$, 300 MHz, ppm) 7.38 (d, 1H), 6.98 (d, 2H), 6.74 (d, 2H), 6.72 (m, 2H), 6.51 (t, 1H), 6.43–6.40 (m, 1H), 6.35–6.31 (m, 1H), 4.84–4.76 (m, 1H), 4.04–3.97 (m, 1H), 3.39 (s, 6H), 3.33 (s, 2H), 2.36–2.18 (m, 2H), 1.91–1.75 (m, 2H), 1.72 (s, 3H), 1.19–0.99 (m, 2H), 0.46–0.37 (m, 6H).

EXAMPLE 51

Synthesis of BIO-1056

A. A mixture of 3-methoxy-4-nitrobenzoic acid (2.01 g, 10.2 mmol) and thionyl chloride (2.3 mL, 31.5 mmol) was stirred at 80–90° C. for 1.5 h. The reaction was concentrated and the residue diluted with ether. The organic solution was washed with sat. aq. $NaHCO_3$ (2×), $H_2O$, then sat. aq. NaCl, dried ($MgSO_4$) and concentrated to afford 3-methoxy-4-nitrobenzoyl chloride (1.92 g, 87%) as a white solid: $^1H$ NMR ($CDCl_3$, 300 MHz, ppm) 7.95–7.70 (m, 3H), 4.06 (s, 3H).

B. To a cold (0C) solution of $TMSCHN_2$ (2 M in hexane, 1.5 mL, 3.0 mmol) and triethylamine (420 µL, 3.0 mmol) was added a solution of 3-methoxy-4-nitrobenzoyl chloride (0.52 g, 2.4 mmol) in acetonitrile (8.5 mL). The reaction was stirred at 0° C. for 24 h and then concentrated. The residue was slurried with sat. aq. $NaHCO_3$ and the mixture extracted with ether (3×). The combined ether washes were washed with water, then sat. aq. NaCl, dried ($MgSO_4$) and concentrated to afford ω-diazo-3-methoxy-4-nitroacetophenone (0.53 g, 100%) as a yellow foam: $^1H$ NMR ($CDCl_3$, 300 MHz, ppm) 7.88 (d, 10 Hz, 1H), 7.61 (s, 1H), 7.27 (d, 10 Hz, 1H), 5.97 (s, 1H), 4.02 (s, 3H).

C. To a refluxing solution of ω-diazo-3-methoxy-4-nitroacetophenone (7.95 g, 35.9 mmol) in tBuOH (100 mL) was added a filtered solution of silver benzoate (2.50 g, 10.9 mmol) in triethylamine (15 mL) dropwise over 1 h. After refluxing for 45 min, decolorizing carbon was added and the hot mixture filtered thru a pad of Celite. The filtrate was concentrated and the residue diluted with ethyl acetate. The organic solution was washed with 5% aq. $NaHCO_3$ (2×), $H_2O$, 5% aq. citric acid, $H_2O$, then sat. aq. NaCl, dried ($MgSO_4$) and concentrated to afford t-butyl 3-methoxy-4-nitrophenylacetate (8.92 g, 93%) as a brown oil: $^1H$ NMR ($CDCl_3$, 300 MHz, ppm) 7.83 (d, 8.3 Hz, 1H), 7.03 (s, 1H), 6.93 (d, 8.3 Hz, 1H), 3.97 (s, 3H), 3.58 (s, 2H), 1.45 (s, 9H).

D. A mixture of t-butyl 3-methoxy-4-nitrophenylacetate (0.144 g, 0.539 mmol) and 10% Pd on carbon (0.155 g) in ethyl acetate (8 mL) and methanol (2 mL) was stirred under $H_2$ (40–60 psi) for 2 h. The mixture was filtered through Celite and the filtrate concentrated to afford t-butyl 4-amino-3-methoxyphenylacetate (0.123 g, 96%) as a light yellow oil: $^1H$ NMR ($CDCl_3$, 300 MHz, ppm) 6.70 (m, 3H), 4.04 (bs, 2H), 3.84 (s, 3H), 3.42 (s, 2H), 1.43 (s, 9H).

E. To a solution of t-Butyl 4-amino-3-methoxyphenylacetate (0.123 g, 0.52 mmol) in methylene chloride (2.0 mL) was added phenyl isocyanate (60 µL, 0.55 mmol). The reaction was stirred for 45 min then concentrated to afford t-butyl 3-methoxy-4-phenylureidophenylacetate (0.190 g, 100%) as a pale yellow foam: $^1H$ NMR ($CDCl_3$, 300 MHz, ppm) 8.00 (d,11 Hz, 1H) 7.65–6.94 (m, 7H), 6.80 (d, 9.0 Hz, 1H), 6.74 (s, 1H), 3.68 (s, 3H), 3.45 (s, 2H), 1.44 (s, 9H).

F. A solution of t-butyl 3-methoxy-4-phenylureidophenylacetate (0.108 g, 0.303 mmol) in trifluoroacetic acid (5.0 mL) was stirred for 30 min. The reaction was concentrated and the residue coevaporated with methylene chloride (2×) then ether to afford 3-methoxy-4-phenylureidophenylacetic acid (0.090 g, 99%) as a white foam: $^1H$ NMR ($CD_3SOCD_3$, 300 MHz, ppm) 9.28 (s, 1H), 8.18 (s, 1H), 8.02 (d, 7.5 Hz, 1H), 7.58–7.15 (m, 5H), 6.91 (bm, 2H), 6.77 (d, 7.5 Hz, 1H), 3.85 (s, 3H), 3.49 (s, 2H).

G. A solution of 3-methoxy-4-phenylureidophenylacetic acid (0.33 g, 0.88 mmol), Leu-β2 (0.27 g, 0.90 mmol), prepared utilizing procedures C and D, BOP (0.39 g, 0.90 mmol) and DIPEA (0.77 mL, 4.4 mmol) in DMF (5 mL) was stirred for 18 h. The reaction was diluted with ethyl acetate and washed with 60% sat. aq. $NaHCO_3$ (3×), $H_2O$, 5% aq. citric acid (3×), $H_2O$, then sat. aq. NaCl, dried ($MgSO_4$) and concentrated to afford crude product (0.49 g). The crude product was purified by flash chromatography (silica gel, 1:4 hexane-ethyl acetate) to give BIO1056 t-butyl ester (0.35 g, 60%) as a white foam: $^1H$ NMR ($CDCl_3$, 300 MHz, ppm) 8.00 (d,8.1 Hz, 1H), 7.55–7.20 (m, 8H), 7.05 (m, 1H), 6.70 (m, 5H), 5.89 (s, 2H), 5.18 (m, 1H), 4.50 (s, 1H), 3.63 (s, 3H), 3.47 (s, 2H), 2.67 (m, 2H), 1.68–1.40 (bm, 3H), 1.33 (s, 9H).

H. To a cold (0° C.) solution of BIO1056 t-butyl ester (0.35 g, 0.53 mmol) in methylene chloride (5.0 mL) was added trifluoroacetic acid (5.0 mL). The reaction was allowed to warm to RT and stirred for 1 h then concentrated to afford crude BIO1056 (0.315 g). The crude product was purified by HPLC in two portions to give BIO1056 (0.16 g, 50%) as a white solid: $^1H$ NMR ($CD_3SOCD_3$, 300 MHz, ppm) 9.25 (s, 1H), 8.43 (d, 8.2 Hz, 1H), 8.15 (m, 2H), 8.01 (d, 8.2 Hz, 1H), 7.50–6.55 (m, 10H), 5.97 (s, 2H), 5.08 (m, 1H), 4.31 (m, 1H), 3.85 (s, 3H), 3.41 (m, 2H), 2.64 (m, 2H), 1.55–1.22 (bm, 3H), 0.80 (m, 6H); HPLC (Gradient A), 35.2 min, (Gradient B), 19.4 min; MS, m/z 605.

EXAMPLE 52

Synthesis of BIO-1221

A. To a solution of t-butyl 4-amino-3-methoxyphenylacetate (0.024 g, 0.10 nmol) in methylene chloride (2.0 mL) was added o-tolyl isocyanate (15 µL, 0.12 mmol). The reaction was stirred for 2 h then concentrated to afford t-Butyl 3-methoxy-4-otolylureidophenylacetate (0.036 g, 97%) as a tan foam: $^1H$ NMR ($CDCl_3$, 300 MHz, ppm) 8.05 (d, 7.9 Hz, 1H), 7.55 (d, 7.9 Hz, 1H), 7.45–7.05 (m, 5H), 6.78 (m, 2H), 3.73 (s, 3H), 3.48 (s, 2H), 2.23 (s, 3H), 1.44 (s, 9H).

B. A solution of t-butyl 3-methoxy-4-otolylureidophenylacetate (0.016 g, 0.043 mmol) in trifluoroacetic acid (1.0 mL) was stirred for 1 h. The reaction was concentrated and the residue coevaporated with methylene chloride (2×) then ether to afford 3-methoxy-4-o-tolylureidophenylacetic acid (0.0135 g, 100%) as a white residue.

C. The procedure described in Example 51G was performed using 3-methoxy-4-o-tolylureidophenylacetic acid (0.0135 g, 0.043 mmol) and amine salt prepared from β-3 utllizing procedures C and D (0.0185 g, 0.041 mmol) to afford BIO1221 methyl ester (0.016 g, 60%) as a white foam: $^1$H NMR (CDCl$_3$, 300 MHz, ppm) 8.10 (d, 1H), 7.61 (d, 1H), 7.45–7.00 (m, 7H), 6.85–6.65 (m, 5H), 5.93 (s, 2H), 5.20 (m, 1H), 4.37 (m, 1H), 3.85 (s, 3H), 3.61 (s, 3H), 3.52 (s, 2H), 2.75 (m, 2H), 2.30 (s, 3H), 1.65–1.10 (bm, 3H), 0.86 (m, 6H).

D. BIO1221 methyl ester (0.016 g, 0.025 mmol) was hydrolyzed using the method described in Example 1B to give BIO-1221 (0.0087 g, 56%) as a white powder: $^1$H NMR (CDCl$_3$, 300 MHz, ppm) 7.93 (d, 1H), 7.70 (d, 1H), 7.49 (d, 1H), 7.37–6.92 (m, 6H), 6.78–6.55 (m, 5H) 5.81 (s, 2H), 5.09 (m, 1H), 4.27 (m, 1H), 3.73 (s, 3H), 3.40 (s, 2H), 2.58 (m, 2H), 2.19 (s, 3H), 1.48–1.25 (bm, 3H), 0.76 (m, 6H); HPLC (Gradient A), 35.2 min; MS, m/z 619.

EXAMPLE 53

Synthesis of BIO-1238

A. The procedure described in Example 43A was performed using amine β-5 to give 1238-1. Yield: 92%. $^1$HNMR (CDCl$_3$, 300 MHz, ppm): 7.19 (d, 2H, J=8.6 Hz), 6.82 (d, 2H, J=8.6 Hz), 5.36–5.28 (m, 2H), 4.25–4.22 (m, 1H), 3.72 (s, 3H), 3.56 (s, 3H), 2.72–2.66 (m, 2H), 2.49–2.41 (m, 2H), 2.1 (s, 3H), 1.92–1.78 (m, 1H), 1.48 (s, 9H). The Boc group was removed by TFA/CH$_2$Cl$_2$ to afford TFA salt 1238-1. $^1$HNMR (CDCl$_3$, 300 MHz, ppm): 7.12 (d, 2H, J=8.5 Hz), 6.74 (d, 2H, J=8.5 Hz), 5.32 (m, 1H), 4.38 (m, 1H), 3.68 (s, 3H), 3.51 (s, 3H), 2.77–2.69 (m, 2H), 2.55–2.38 (m, 1H), 2.36–2.31 (m, 1H), 2.16–2.02 (m, 2H), 1.91 (s, 3H).

B. The procedure described in Example 1A was performed using 2-methylphenylureaphenylacetic acid (20 mg, 0.7 mmol) and TFA salt 1238-1 (30 mg, 0.7 mmol) to give 1238-2 (35 mg, 83%) as a white solid. $^1$HNMR (DMSO-d$^6$, 300 MHz, ppm): 7.91 (d, 1H), 7.52 (d, 2H, J=8.5 Hz), 7.35–7.30 (m, 4H), 7.02 (d, 1H), 6.80 (d, 2H, J=8.5 Hz), 5.79–5.68 (m, 1H), 4.40–4.28 (m, 1H), 3.71 (s, 3H), 3.63 (s, 3H), 3.35–3.38 (m, 2H), 2.49 (br, s, 2H), 2.00 (s 3H).

C. A solution of 1238-2 (20 mg, 0.033 mmol) in MeOH (3 mL) and aqueous LiOH (3 mL of 2N) was stirred at room temperature overnight, the reaction mixture was cooled to 0° C. and acidified by adding TFA until pH=3–4 (pH paper). The desired product was isolated and purified by LC (Vydac C18 column; gradient 8) to give 12 mg (0.017 mmol; 61%) of BIO-1238 as a white solid: FAB-MS=595.

EXAMPLE 54

Synthesis of BIO-1245

A. 1245-1 was prepared from commercially available N-BOC-methionine sulfone (562 mg, 2.0 mmol) and amine β-3 (470 mg, 2.10 mmol) using the method described in Example 1A to afford crude 1245-1 (962 mg, 1.90 mmol, 95%) as a white foam which was used without further purification. $^1$HNMR(CDCl$_3$): δ 7.31 (1H, d, J=8.3 Hz), 6.77–6.73 (3H, m), 5.91 (2H, s), 5.40 (1H, d, J=7.6 Hz), 5.27 (1H, m), 4.30 (1H, br), 3.61 (3H, s), 3.15 (1H, m), 2.93 (1H, m), 2.89 (3H, s), 2,85 (2H, m), 2.22 (2H, m), 1.42 (9H, s).

B. Compound 1245-1 (962 mg, 1.90 mmol) was treated with 4N HCl/dioxane as the reagent. Concentration affords the hydrochloride salt 1245-2 as a white solid (800 mg, 1.89 mg, 1.89 mmol, 99%) which was used without further purification. $^1$HNMR(CDCl$_3$): δ 8.75 (1H, br), 8.20 (2H, br), 6.91–6.55 (3H, m), 5.90 (2H, bs), 5.42 (1H, br), 4.55 (1H, br) 3.60 (3H, s), 3.45–3.0 (2H, bm), 2.90 (3H, s), 2.85–2.40 (4H, bm).

C. The procedure described in Example 22D was performed using compound 1245-2 (800 mg, 1.89 mmol) and o-methylphenylureaphenyl acetic acid (543 mg, 1.89 mmol) to afford crude 1245-3 (1.15 g, 1.76 mmol, 93%) as a white solid which used without further purification.

$^1$HNMR(DMSO=d$_6$): δ 7.95 (1H, s), 7.89 (1H, d, J=7.9 Hz), 7.43 (2H, D, J=7.9 Hz), 7.20 (4H, m), 7.00–6.78 (4H, m), 6.03 (2H, s), 5.18 (1H, m), 4.40 (1H, m), 3.58 (3H, s), 3.49 (3H, s), 3.39 (2H, br), 2.90–2.49 (2H, m), 2.29 (3H, s), 2.00 (2H, m).

D. Compound 1245-3 (1.1 g, 1.7 mmol) was hydrolyzed as described in Example 1B to afford crude BIO-1245 (490 mg, 0.77 mmol, 45%) as a white solid>90% pure by HPLC. A small amount (~150 mg) was purified by prep HPLC to afford pure BIO-1245 (81 mg, 54% recovery) as a white solid m/z=639 (100% pure by HPLC). $^1$HNMR(DMSO-d$_6$): δ 8.60(0.5H, bs), 8.57 (1H, d, J=8.1 Hz), 8.37 (1H, d, J=8.1 Hz), 8.18 (1H, s), 8.05(0.5H, s), 7.89 (1H, d, J=8.0 Hz), 7.43 (2H, d, J=8.04z), 7.21 (4H, m), 6.976.81 (4H, m), 6.03 (2H, s), 5.13 (1H, m), 4.43 (1H, m), 3.80 (1H, br), 3.49 (3H, s), 2.93 (2H, m), 2.45 (2H, m), 2.30 (3H, s), 2.01 (2H, m).

EXAMPLE 55

Synthesis of BIO-1246

A. To a suspension of L-cysteine (1.5 g, 12.4 mmol) in methanol (8 mL) was added excess sodium methoxide (2.0 g, 37.2 mmol) followed by a catalytic amount of sodium iodide (~100 mg). After stirring at room temperature for 30 min. 1-bromo-2-propanol (1.7 g, 12.4 mmol) was added and the reaction was stirred overnight. The reaction mixture was then neutralized to pH-7, diluted with water (20 mL) and concentrated to remove the methanol. The solution was then diluted with dioxane (20 mL) and triethylamine (7.0 mL, 50 mmol) was added followed by BOCON (3.1 g, 12.4 mmol) and the reaction was stirred at room temperature for 3 h. The reaction was worked up by diluting with water (20 mL) and extracting with ethyl acetate (3×25 mL). The organic extracts were discarded and the aqueous solution acidified to pH=1 with 1N HCl. The aqueous was extracted with ethyl acetate (4×30 mL), dried over sodium sulfate and concentrated to afford 1246-1 (2.87 g, 10.4 mmol, 83%, 2 steps) as a thick pale yellow syrup. $^1$HNMR(CDCl$_3$) δ 5.60–5.50 (1H, br), 4.60–4.50 (1H, br), 4.44 (2H, t, J=6.3 Hz), 3.02 (2H, bm), 32.65 (2H, br) 2.03 (2H,M), 1.45 (9H, S).

B. The procedure of Example 1A was performed using 1246-1 (33 mg, 0.11 mmol) and amine β-3 (22 mg, 0.10 mmol) to afford 1246-2 (39 mg, 0.08 mmol, 80%) as a pale yellow foam which was used without purification in the next step. $^1$HNMR(CDCl$_3$): δ 6.80–6.60 (3H, m), 5.91 (2H, s), 5.50 (1H, bm)., 4.35 (1H, bm), 3.71, (2H, bt), 3.61 (3H, s), 3.15–2.65 (6H, m), 1.85 (2H, m), 1.46 (9H, s).

C. Compound 1246-2 (39 mg, 0.08 mmol) was treated with TFA to give the corresponding amine-TFA salt of 1246-2 which was subjected to the conditions described in Example 54C to give a white solid which was directly hydrolysed as described in Example 1B to the free acid. A small aliquot was purified by HPLC. The clean fractions were collected to afford BIO-1246(~3 mg) M/Z=637(100% pure by HPLC) as a white solid.

¹HNMR(DMSO-d₆): δ 9.01 (1H, s), 8.66 (1H, d, J=5.3 Hz), 8.30 (1H, d, J=5.5 Hz), 7.94 (1H, s), 7.88 (1H, d, J=5.3 Hz), 7.42 (2H, d, J=5.5 Hz), 7.20–7.15 (4H, m), 7.00–6.94 (2H, m), 6.88–6.79 (2H, m), 6.02 (2H, s), 5.12 (1H, m), 4.48 (1H, m), 3.65 (2H, m), 2.90–2.45 (6H, m), 2.28 (3H, s), 1.65 (2H, m).

EXAMPLE 56

Synthesis of BIO-1248

A. A mixture of 4-fluorobenzaldehyde (2.48 g; 20 mmol), malonic acid (2.5 g, 24 mmol) and ammonium acetate (2.16 g; 28 mmol) in ethanol (100 mL) was refluxed under argon overnight. After cooling to room temperature, the solid precipitate was collected by filtration and washed with ethanol (3×30 mL) and dried under vacuum to give 1.0 g (27%) of white solid, which was used without further purification.

To a suspension of the white solid (1.0 g, 9.4 mmol) in methanol was added SOCl₂ (6.01 mmol; 5.2 mL of 2 M in CH₂Cl₂). The resultant solution was stirred at room temperature overnight. After removal of excess solvent, the residue was dissolved in EtOAc, basified with sat. NaHCO₃, and dried with Na₂SO₄. The organic solution was concentrated under reduced pressure to give 900 mg (84%) of amine 1248-1 as a light yellow oil: ¹H NMR (CDCl₃, 300 MHz, ppm) 7.28 (m, 2H, Ar), 6.96 (m, 2H, Ar), 4.46 (t, J=6.8, 1H), 3.62 (s, 3H, OMe), 2.58 (d, J=6.8 Hz, 2H), 1.69 (s, 2H, NH); TLC, 10% MeOH/CH₂Cl₂, R$_f$=0.5.

B. Amine 1248-1 (300 mg, 1.52 mmol) was coupled with Nα-t-Boc-Nε-leu-N-hydroxysuccinimide (300 mg, 1.52 mmol) using the method described in Procedure C. The resulting adduct was deprotected with trifluoroacetic acid and, then basified with Et₃N as described in Procedure D1 to give the amine 1248-2 in 84%: ¹H NMR (CDCl₃, 300 MHz, ppm) 8.20 (d, J=7.1 Hz, 1H), 7.24 (m, 2H, Ar), 6.97 (m, 2H, Ar), 5.33 (m, 1H), 3.58 (s, 3H, OMe), 3.38 (m, 1H)₆ 2.82 (m, 2H), 1.66 (m, 2H), 1.30 (m, 1H), 1.22 (s, 2H), 0.91 (m, 6H); TLC, 10% MeOH/CH₂Cl₂, R$_f$=0.47 and 0.38.

C. 2-Methylphenylureaphenylacetic acid (77 mg, 0.27 mmol) was coupled with amine 1248-2 (70 mg, 0.23 mmol) using the method described in Example 22D to give 1248-3 in 61% yield. ¹H NMR (DMSO-d⁶, 300 MHz, ppm) δ 9.15 (d, J=5.9 Hz, 1H), 8.53 (t, J=7.5 Hz, 1H), 8.17 (d, J=8.2 Hz, 1H), 8.0 (s, 1H), 7.84 (d, J=8.0 Hz, 2H), 7.35 (m, 4H), 7.13 (m, 6H), 6.92 (t, J=8.2 Hz, 1H), 5.20 (m, 1H), 4.30 (m, 1H), 3.52 (s, two peaks, 3H, OMe), 3.45–3.24 (m, 2H), 2.75 (m, 2H), 2.24 (s, 3H, Me), 1.57–1.33 (m, 3H), 0.82 (m, 6H); HPLC (gradient 1**) 21.2 min and 21.5 min (1:24); FABMS, m/z 577 (C₃₃H₃₇N₄O₅F of M⁺1 requires 577).

D. A solution of 1248-3 (22 mg, 0.038 mmol) in DMSO (1 mL) and MeOH (2 mL) was hydrolyzed with aqueous LiOH as described in Example 1B. The product was purified on a Vydac reverse-phase C18 column (22 mm×25 cm) using a linear gradient of 15% CH₃CN/H₂O (0.1% TFA) to 40% CH₃CN/H₂O (0.1% TFA) with a flow rate of 10 mL/min to give BIO-1248 in 29% isolated yield. ¹H NMR (DMSO-d⁶, 300 MHz, ppm) δ 8.93 (s, 1H), 8.46 (d, J=8.3 Hz, 1H), 8.25 (d, J=8.2 Hz,1H), 7.87 (s, 1H), 7.82 (d, J=8.0 Hz, 1H), 7.33 (m, 5H), 7.12 (m, 5H) 6.93 (m, 1H), 5.15 (m, 1H), 4.28 (m, 1H), 3.35 (m, 2H), 2.65 (d, J=7.2 Hz, 2H), 2.22 (s, 3H, Me), 1.55 (m, 1H), 1.43 (m, 2H), 0.83 (m, 6H); HPLC (gradient 1) 18.7 min and 19.3 min (1:24); FABMS, m/z 563 (C₃₁H₃₅N₄O₅F of M⁺1 requires 563).

EXAMPLE 57

Synthesis of BIO-1270

A. Amine β-3 (500 mg, 2.24 mmol) was coupled with Nα-Cbz-Nε-t-Boc-$_L$-Lys-N-hydroxysuccinimide (1.0 g, 2.1 mmol) using Procedure C to give the coupled adduct 1270-1 (1.1 g, 82%). This adduct was deprotected with trifluoroacetic acid and was basified with Et₃N as previously described in Procedure D to give 1270-2 in 54% yield. ¹H NMR (CDCl₃, 300 MHz, ppm) δ 7.31 (m, 6H), 6.72 (m, 3H), 5.90 (s, 2H), 5.58 (d, J=9 Hz, 1H), 5.26 (m, 1H), 5.07 (s, 2H), 4.15 (m, 1H), 3.58 (s, 3H, OMe), 2.77 (m, 2H), 2.61 (m, 2H), 1.79 (m, 1H), 1.59 (m, 1H), 1.41–1.30 (m, 6H); TLC, 10% MeOH/CH₂Cl₂, R$_f$=0.11.

B. To a stirred solution of 1270-2 (15.5 mg, 0.032 mmol) and pyridine (10.1 mg, 0.128 mmol) in CH₂Cl₂ at rt is added acetyl chloride (7.5 mg, 0.096 mmol). After stirring for 3 hours the reaction is concentrated and reverse phase chromatography provided 1270-3 (16.3 mg, 95%) as a white foam. ¹HNMR(CDCl₃, 300 MHz, ppm) 7.32(S, 5H), 6.70 (m, 3H) 5.91 (s, 2H), 5.82 (m, 1H), 5.55 (m, 1H), 5.25 (m, 1H), 5.09 (s, 1H), 4.13 (m, 1H), 3.60(S, 3H), 3.28(M, 2H), 2.9–2.4 (m, 3H), 1.94(S, 3H), 1.9–1.76 (m, 1H) 1.70–1.58 (m, 1H), 1.52–1.42 (m, 2H), 1.36–1.22 (m, 2H).

C. Procedure D2 was performed using 1270-3 (reaction progress was followed by HPLC) to give compound 1270-4 (14.1 mg, quantitative yield) as a clear oil which was used as the crude material.

D. The procedure of Example 54C was performed using 1270-4 (14.1 mg, 0.036 mmol). Purification was carried out via preperative HPLC and provided Bio 1270-OMe (9.1 mg, 38%) as a white solid. ¹HNMR(DMSO$_{D6}$, 300 MHz, ppm), 8.13 (d, 1H J=10.35), 8.03 (s, 1H), 7.93 (d, 1H J=10.35), 7.83 (m, 1H), 7.49 (d, 2H J=10.35), 7.28 (m, 5H), 7.10–6.81 (m. 5H), 6.08 (s, 2H), 5.20 (dd, 1H J=9.66, 17.25), 4.33 (dd, 1H J=8.97, 15.18), 3.63 (s, 3H), 3.5 (s, 2H), 3.1–2.95 (m, 2H), 2.85–2.74 (m, 2H), 2.33 (s, 3H), 1.86 (s, 3H), 1.72–1.49 (m, 2H), 1.5–1.32 (m, 3H), 1.311.09 (m, 2H).

E. To Bio 1270-OMe (9.1 mg, 0.016) in 1 ml of DMSO$_{D6}$ (NMR sample) was added 20 ul of 2N LiOH (0.041 mmol) and the reaction was stirred at rt. overnight. The reaction was acidified (red to litmus) with 3 drops of TFA and purified by preparative HPLC This afforded BIO-1270 (6.2 mg, 60%) as a white solid. ¹HNMR(DMSO$_{D6}$, 300 MHz, ppm), 8.5 (d, 12H J=10.35), 8.19 (d, 1H J=10.35), 7.99 (s, 1H), 7.93 (d, 1H J=10.35), 7.82 (m, 1H), 7.45 (d, 2H J=10.35). 7.28 (m, 4H), 7.05 (m, 1H), 6.98–6.89 (m, 2H) 6.86 (m, 1H), 6.09(S, 2H), 5.66 (dd, 1H J=8.28, 16.56) 4.32 (dd, 1H J=7.59, 13.8), 3.27 (s, 2H), 2.98 (m, 2H) 2.75 (m, 2H), 2.33 (s, 3H), 1.87 (s, 3H), 1.69–1.48 (m, 2H), 1.46–1.32 (m, 3H), 1.28–1.12 (m, 2H); MS, m/z 646; HPLC (Gradient 1) 19.73 min. 100%.

Gradient 3 15% B→65% B 50 min.

Gradient 1 20% B→70% B 50 min.

EXAMPLE 58

Synthesis of BIO-1282

A. A solution of ethyl 3-pyridylacetate (1.65 g, 9.90 mmol) in 32% peracetic acid (10 mL) was stirred at 80–90° C. for 2 h. The reaction was concentrated and the residue coevaporated with methanol (2×) then methylene chloride to afford ethyl 3-pyridylacetate N-oxide (1.80 g, 100%) as a white solid: $^1$H NMR (CDCl$_3$, 300 MHz, ppm) 8.38 (s, 1H), 8.22 (d, 1H), 7.39 (d, 1H), 4.20 (q, 2H), 3.62 (s, 2H), 1.26 (t, 3H).

B. A solution of salicylamide (4.14 g, 30.2 mmol) and conc. sulfuric a-id (3 drops) in acetone (40 mL) was refluxed for 5 h. The reaction was concentrated and the residue taken up in ethyl acetate. The organic solution was washed with 1 N NaOH (2×), 1 N HCl (2×), H$_2$O, then sat. aq. NaCl, dried (MgSO$_4$) and concentrated to afford 2,2-dimethyl-4-keto-1,3-benzoxazine (2.50 g, 47%) as a white solid: $^1$H NMR (CDCl$_3$, 300 MHz, ppm) 7.92 (d, 1H), 7.60 (bs, 1H), 7.47 (m, 1H), 7.06 (m, 1H), 6.92 (d, 1H), 1.65 (s, 6H).

C. A solution of 2,2-dimethyl-4-keto-1,3-benzoxazine (1.77 g, 10.0 mmol) and PCl$_5$ (2.09 g, 10.0 mmol) in POCl$_3$ (3.0 mL) was stirred at RT for 1 h then at 50–60° C. for 2 h. The reaction was concentrated and the product distilled (90–95° C./2–3 mm Hg) to afford 4-chloro-2,2-dimethyl-3H-1,3-benzoxazine. (0.496 g, 25%) as a clear oil: $^1$H NMR (CDCl$_3$, 300 MHz, ppm) 7.58 (d, 1H), 7.48 (m, 1H), 6.97 (m, 1H), 6.94 (d, 1H), 1.63 (s, 6H).

D. A mixture of 4-chloro-2,2-dimethyl-3H-1,3benzoxazine (0.145 g, 0.741 mmol) and ethyl 3-pyridylacetate N-oxide (0.270 g, 1.49 mmol) in methylene chloride (5.0 mL) was refluxed for 20 h. The reaction was concentrated and the residue taken up in ethyl acetate. The organic mixture was washed with 60% sat. aq. NaHCO$_3$ (2×), H$_2$O, sat. aq. NaCl, dried (MgSO$_4$), and concentrated to afford an oily residue (0.148 g).

The crude oily residue (0.148 g) in conc. HCl (10 mL) was refluxed for 18 h. The reaction was concentrated and the residue partitioned in H$_2$O and methylene chloride. The aqueous solution was washed with methylene chloride (2×) and then concentrated to afford a white solid (0.105 g).

A solution of the white solid (0.105 g) in methanol (5.0 mL) was treated with thionyl chloride (0.5 mL, 7 mmol) dropwise over 30 min. The reaction was stirred for 2 h then concentrated. The residue was taken up in 5% aq. NH$_4$OH and extracted with methylene chloride (3×). The organic extracts were dried (MgSO$_4$) and concentrated to afford methyl 5-(2-aminopyridyl)acetate (0.012 g, 10% for three steps) as a white solid: $^1$H NMR (CDCl$_3$, 300 MHz, ppm) 7.93 (s, 1H), 7.40 (d, 1H), 6.50 (d, 1H), 4.52 (bs, 2H), 3.70 (s, 3H), 3.49 (s, 2H); MS, m/z 167.

E. To a solution of methyl 5-(2-aminopyridyl)acetate (0.012 g, 0.072 mmol) in methylene chloride (1.0 mL) was added o-tolyl isocyanate (10 µL, 0.081 mmol). The reaction was stirred for 1 h then concentrated to afford a white residue (0.020 g) containing methyl 5-(2-o-tolylureido)pyridylacetate.

F. A solution of crude methyl 5-(2-o-tolylureido)pyridylacetate (0.020 g) in methanol (1.0 mL) was treated with 2 M LiOH (100 µL, 0.20 mmol). The reaction was stirred for 18 h then concentrated. The crude product was purified by HPLC to afford 5-(2-o-tolylureido)pyridylacetic acid (0.013 g, 65%) as a white powder: $^1$H NMR (CDCl$_3$, 300 MHz, ppm) 8.10 (s, 1H), 7.87 (bd, 1H), 7.75 (bd, 1H), 7.21 (m, 1H), 7.08 (m, 1H), 3.62 (s, 2H), 2.38 (s, 3H); MS, m/z 286.

G. The procedure described in Example 1A was performed using 5-(2-o-tolylureido)pyridylacetic acid (0.013 g, 0.045 mmol) and the amine prepared in Example 14A (0.022 g, 0.049 mmol) to afford BIO1282 methyl ester (0.020 g, 60%): $^1$H NMR (CDCl$_3$, 300 MHz, ppm) 8.18–7.73 (m, 4H), 7.55 (d, 1H), 7.35–6.65 (m, 10H), 5.93 (s, 1H), 5.28 (m, 1H), 4.45 (m, 1H), 3.69–3.45 (m, 5H), 2.81 (bm, 2H), 2.20 (s, 3H), 1.54 (bm, 3H), 0.92 (m, 6H).

H. To a mixture of BIO1282 methyl ester (0.020 g, 0.033 mmol) in methanol (02.0 mL) was added 2.0 M LiOH (200 µL, 0.40 mmol). The reaction was stirred for 20 h then concentrated. The residue (containing a 4:5 mixture of BIO1282 and starting ester) was dissolved in DMF (0.5 mL) and methanol (0.5 mL) then stirred for an additional 28 h. The reaction was acidified with trifluoroacetic acid and concentrated. The crude product was purified by HPLC to give BIO-1282 (0.0056 g, 24%) as a white powder: $^1$H NMR (CDCl$_3$, 300 MHz, ppm) 8.44 (d, 8.1 Hz, 1H), 8.26 (d, 8.3 Hz, 1H), 8.15 (s, 1H), 8.04 (d, 8.0 Hz, 1H), 7.66 (d, 8.7 Hz, 1H), 7.32–7.13 (m, 3H), 7.05–6.94 (m, 1H), 6.85–6.65 (m, 3H), 5.96 (s, 2H), 5.06 (m, 1H), 4.29 (m, 1H), 3.45 (m, 2H), 2.63 (m, 2H), 2.31 (s, 3H), 1.57–1.20 (m, 3H), 0.78 (m, 6H); HPLC (Gradient A), 27.0 min; MS, m/z 590.

EXAMPLE 59

Synthesis of BIO-1294

A. To a stirred solution of the amine prepared in Example 57A (102 mg, 0.21 mmol) in CH$_2$Cl$_2$ (20) was added CH$_3$SO$_2$Cl (48 mg, 32 µL, 0.42 mmol) and Et$_3$N (50 µL). The resulting mixture was stirred at RT for 18 h. The reaction mixture was diluted with CH$_2$Cl$_2$ (40 mL), washed with 5% citric acid (20 mL), H$_2$O (10 mL), Sat. NaHCO$_3$ (20 mL), Sat. NaCl (20 mL) and dried with Na$_2$SO$_4$. The organic solution was concentrated under reduced pressure to give 110 mg (92%) of 1294-1 as a white solid: $^1$H NMR (CDCl$_3$, 300 MHz, ppm) δ 7.30 (m, 6H), 6.74 (m, 3H), 5.90 (s, 2H), 5.70 (m, 1H), 5.25 (m, 1H), 5.07 (s, 3H), 4.16 (m, 1H), 3.58 (s, 3H, OMe), 3.02 (m, 2H), 2.88 (s, 3H), 2.75 (m, 2H), 1.76 (m, 1H), 1.60 (m, 1H), 1.50 (m, 2-H), 1.32 (m, 2H); TLC, 10% MeOH/CH$_2$Cl$_2$, R$_f$=0.67.

B. To a solution of compound 1294-1 (110 mg, 0.195 mmol) was dissolved in methanol (10 ml) was added acetic acid (0.2 ml) and Pd(OH)$_2$ (110 mg). The resulting mixture was hydrogenated (H$_2$, 50 psi) at RT for 48 h. After standard work-up, 1294-2 (35 mg, 42%) was obtained as colorless oil: $^1$H NMR (CDCl$_3$, 300 MHz, ppm) δ 8.06 (m, 1H), 6.75 (m, 3H), 5.92 (s, 2H), 5.25 (m, 1H), 5.02 (m, 1H), 3.61 (s, 3H), 3.35 (m, 1H), 3.10 (m, 2H), 2.94 (s, 3H), 2.80 (m, 2H), 1.87–1.30 (m, 8H); HPLC (gradient 8) 12 min.

C. 2-Methylphenylureaphenylacetic acid (35 mg, 0.12 mmol) was coupled with the amine 1294-2 (35 mg, 0.08 mmol) as described in Example 1A to give compound 1294-3 in 88%. $^1$H NMR (CDCl$_3$, 300 MHz, ppm) δ 8.50 (m, 1H), 8.30 (s, 1H), 8.16 (m, 1H), 7.82 (m, 1H), 7.40 (m, 2H), 7.22-7.05 (m, 5H), 7.00–6.70 (m, 5H), 5.98 (s, 2H), 5.11 (m, 1H), 4.22 (m, 1H), 3.52 (s, 3H), 3.36 (m, 2H), 2.91–2.62 (m, 7H), 2.25 (s, 3H), 1.60–1.05 (m, 6H); HPLC (gradient 8) 31 min; FABMS, m/z 696 (C$_{34}$H$_{41}$N$_5$O$_9$S of M$^+$1 requires 696).

D. A solution of compound 1294-3 (50 mg, 0.07 mmol) in MeOH (3 mL) was hydrolyzed with aqueous LiOH as previously described. The product was purified on a Vydac reverse-phase C18 column (22 mm×25 cm) using a linear gradient of 15% CH$_3$CN/H$_2$O (0.1% TFA) to 40% CH$_3$CN/H$_2$O (0.1% TFA) with a flow rate of 10 mL/min to give BIO-1294 in 41% isolated yield. $^1$H NMR (CDCl$_3$, 300 MHz, ppm) δ 8.95 (m, 1H), 8.42 (d, J=8.2 Hz, 1H), 8.08 (d, J=8.1 Hz, 1H), 7.88 (s, 1H), 7.83 (d, J=8.0 Hz, 2H), 7.36 (d, J=8.2 Hz, 2H), 7.15 (m, 4H), 7.10–6.71 (m, 5H), 5.97 (s, 2H), 5.04 (m, 1H), 4.22 (m, 1H), 3.41–3.25 (m, 2H), 2.83–2.80 (m, 6H), 2.23 (s, 3H), 1.70–1.04 (m, 6H); HPLC (gradient 8) 27 min; FABMS, m/z 682 (C$_{33}$H$_{39}$N$_5$O$_9$S of M$^+$1 requires 682).

EXAMPLE 60

Synthesis of BIO-1321

A. A mixture of methyl 4-formylbenzoate (3.48 g; 20 mmol), malonic acid (2.5 g, 24 mmol) and ammonium acetate (2.16 g; 28 mmol) in ethanol (100 mL) was refluxed under argon overnight. After cooling to room temperature, the solid precipitate was collected by filtration and washed with ethanol (3×30 mL). The white solid was dried under vacuum overnight to give 2.8 g (63%) of 13211.

B. To a suspension of compound 1321-1 (1.0 g, 4.48 mmol) in methanol (50 mL) was added $SOCl_2$ (5.4 mmol; 2.7 mL of 2 M in $CH_2Cl_2$). The resultant solution was stirred at room temperature overnight. After removal of excess solvent, the residue was dissolved in EtOAc, basified with sat. $NaHCO_3$, and dried with $Na_2SO_4$. The organic solution was concentrated under reduced pressure to give 780 mg (53%) of the amine 1321-2 as a light yellow oil: $^1H$ NMR ($CDCl_3$, 300 MHz, ppm) 7.99 (m, 2H, Ar), 7.56 (d, J=8.1 Hz, 1H, Ar), 7.42 (d, J=8.0 Hz, 1H, Ar), 4.46 (t, J=6.7, 1H), 3.85 (s, 3H, OMe), 3.65 (s, 3H, OMe), 2.65 (d, J=6.8 Hz, 2H), 1.88 (s, 2H, NH).

C. The amine 1321-2 (500 mg, 1.11 mmol) was coupled with Nα-t-Boc-Nε-Leucine-N-Hydroxysuccinimide (380 mg, 1.0 mmol) as described in Procedure C to give material which was deprotected with trifluoroacetic acid and, then basified with $Et_3N$ as described in Procedure D1 to give amine 1321-3 in 70% yield: $^1H$ NMR ($CDCl_3$, 300 MHz, ppm) 8.32 (t, J=9.1 Hz, 1H), 8.20 (d, J=8.3 Hz, 2H), 7.34 (m, 2H, Ar), 5.40 (m, 1H), 3.86 (s, 3H, OMe), 3.58 (s, 3H, OMe), 3.41 (m, 1H), 2.85 (m, 2H), 1.67 (m, 2'. H), 1.53 (s, 2H), 1.30 (m, 1H), 0.90 (m, 6H).

D. 2-Methylphenylureaphenylacetic acid (54 mg, 0.19 mmol) was coupled with amine 1321-3 (70 mg, 0.23 mmol) using the method described in Example 22D to give the 1321-4 in 87% yield: —H NMR (DMSO-$d^6$, 300 MHz, ppm) δ 8.62 (m, 1H), 8.18 (d, J=8.1 Hz, 1H), 8.10 (m, 1H), 7.94–7.82 (m, 4H), 7.48–7.34 (m, 4H), 7.17–7.13 (m, 4H), 6.91 (t, J=7.3 Hz, 1H), 5.24 (m, 1H), 4.30 (m, 1H), 3.53 (s, two peaks, 3H, OMe), 3.39–3.34 (m, 2H), 3.05 (m, 2H), 2.24 (s, 3H, Me), 1.60–1.36 (m, 3H), 0.83 (m, 6H); HPLC (gradient 8) 40 min (1:1); FABMS, m/z 617 ($C_{33}H_{40}N_4O_7$ of $M^+1$ requires 617).

E. A solution of 1321-4 (70 mg, 0.11 mmol) in DMSO (1 mL) and MeOH (2 mL) was hydrolyzed with aqueous LiOH as described in Example 1B. The product was purified on a Vydac reverse-phase C18 column (22 mm×25 cm) using a linear gradient of 15% $CH_3CN/H_2O$ (0.1% TFA) to 40% $CH_3CN/H_2O$ (0.1% TFA) with a flow rate of 10 mL/min to give BIO-1321 (22 mg, 34% isolated yield): $^1H$ NMR (DMSO-$d^6$, 300 MHz, ppm) δ 8.95 (d, J=4.6 Hz, 1H), 8.57 (m, 1H), 8.13 (d, J=8.3 Hz, 1H), 7.88–7.81 (m, 4H), 7.44–7.32 (m, 4H), 7.17–7.10 (m, 4H), 6.92 (t, J=7.4 Hz, 1H), 5.20 (m, 1H), 4.31 (m, 1H), 3.46–3.27 (m, 2H), 2.70 (m, 2H), 2.22 (s, 3H, Me), 1.59–1.32 (m, 3H), 0.81 (m, 6H); HPLC (gradient 8) 27.8 min and 28.1 min (1:1); FABMS, m/z 589 ($C_{31}H_{36}N_4O_7$ of $M^+1$ requires 589)

EXAMPLE 61

Synthesis of BIO-1336

A. A slurry of 2,6-dichloro-3-nitropyridine (92%, 9.9 g, 47 mmol) and $K_2CO_3$ powder (6.5 g, 47 nmol) in methanol (100 mL) was stirred for a week at RT. The reaction was filtered and concentrated. The residue was partitioned in ethyl acetate and 60% sat. aq. $NaHCO_3$. The organic solution was washed with 60% sat. aq. $NaHCO_3$ (2×), $H_2O$, then sat. aq. NaCl, dried ($MgSO_4$) and concentrated to afford 2-chloro-6-methoxy-5-nitropyridine and 2-chloro-6-methoxy-3-nitropyridine (8.9 g, 100%) as a light yellow solid: $^1H$ NMR ($CDCl_3$, 300 MHz, ppm) 8.31 (d, 8.3 Hz, 1H), 8.28 (d, 8.9 Hz, 1H), 7.10 (d, 8.3 Hz, 1H)# 6.82 (d, 8.9 Hz, 1H), 4.15 (s, 3H), 4.06 (s, 3H).

B. A mixture of 2-chloro-6-methoxy-5-nitropyridine and 2-chloro-6-methoxy-3-nitropyridine (8.9 g, 47 mmol), t-butyl methyl malonate (10 mL, 60 mmol), and NaH (95%, 3.1 g, 120 mmol) in THF (250 mL) was stirred at RT for 24 h. The reaction was concentrated and the residue treated with trifluoroacetic acid (200 mL) for 2 h. The reaction was concentrated and the product separated by flash chromatography (silica gel, 95:5 hexane-ethyl acetate) to afford methyl 6-(2-methoxy-3-nitro)pyridylacetate (3.3 g, 62%) as a yellow oil: $^1H$ NMR ($CDCl_3$, 300 MHz, ppm) 8.27 (d, 8.0 Hz, 1H), 7.04 (d, 8.0 Hz, 1H), 4.09 (s, 3H), 3.85 (s, 2H), 3.75 (s, 3H).

C. A mixture of methyl 6-(2-methoxy-3-nitro)pyridylacetate (0.047 g, 0.21 mmol) and 10% Pd on carbon (0.063 g) in ethyl acetate (2 mL) and ethanol (1 mL) was stirred under $H_2$ (40–50 psi) for 6 h. The mixture was filtered thru Celite and the filtrate concentrated to afford methyl 6-(3-amino-2-methoxy)pyridylacetate (0.041 g, 100%) as a light yellow oil: $^1H$ NMR ($CDCl_3$, 300 MHz, ppm) 6.82 (d, 7.6 Hz, 1H), 6.65 (d, 7.6 Hz, 1H), 3.94 (s, 3H), 3.70 (s, 3H), 3.65 (s, 2H).

D. To a solution of methyl 6-(3-amino-2-methoxy)pyridylacetate (0.078 g, 0.33 mmol) and triethylamine (50 mL, 0.36 mmol) in methylene chloride (1.0 mL) was added o-tolyl isocyanate (41 μL, 0.36 mmol). The reaction was stirred for 4 h then concentrated. The crude product was purified by flash chromatography (silica gel, 3:2 hexane-ethyl acetate) to afford the Methyl 6-(2-methoxy-3-o-tolylureido)pyridylacetate (0.060 g, 55%) as a white powder: $^1H$ NMR ($CDCl_3$, 300 MHz, ppm) 8.33 (d, 7.9 Hz, 1H), 7.51 (d, 7.8 Hz, 1H), 7.41 (s, 1H), 7.17 (m, 2H), 7.08 (m, 2H), 6.77 (d, 7.9 Hz, 1H), 3.81 (s, 3H), 3.71 (s, 3H), 3.67 (s, 2H), 2.20 (s, 3H).

E. A solution of methyl 6-(2-methoxy-3-otolylureido)pyridylacetate (0.023 g, 0.070 mmol) in methanol (1.0 mL) was treated with 2 M LiOH (90 μL, 0.18 mmol). The reaction was stirred for 18 h, diluted with $H_2O$ (5.0 mL) and washed with ether (2×). The aqueous solution was then acidified with 5% aq. citric acid. The product was filtered and washed with $H_2O$ then ether to give 6-(2-Methoxy-3-o-tolylureido)pyridylacetic acid (0.014 g, 64%) as a white solid: $^1H$ NMR ($CD_3OD$, 300 MHz, ppm) 8.50–8.25 (m, 3H), 7.60 (bd, 1H), 7.28–7.00 (m, 3H), 4.01 (s, 3H), 3.69 (s, 2H), 2.30 (s, 3H); MS, m/z 316.

F. Procedure C was performed using amine β-2. The resulting product was subjected to the conditions described in Procedure D1 to provide TFA-amine salt 1336-1.

G. The procedure described in Example 1A was performed using 6-(2-methoxy-3-o-tolylureido)pyridylacetic acid (0.014 g, 0.044 mmol) and amine-TFA salt 1336-1 (0.017 g, 0.045 mmol) to afford BIO1336 t-butyl ester (0.024 g, 79%) as a white foam: $^1H$ NMR ($CDCl_3$, 300 MHz, ppm) 8.40 (d, 7.9 Hz, 1H), 7.63 (d, 8.3 Hz, 1H), 7.50 (d, 7.9 Hz, 1H), 7.43–7.06 (m, 6H), 6.80–6.67 (m, 4H), 5.92 (s, 2H), 5.19 (m, 1H), 4.47 (m, 1H), 3.91 (s, 3H), 3.61 (s, 3H), 2.65 (m, 2H), 2.31 (s, 3H), 1.58 (m, 3H), 1.31 (s, 9H).

H. To a solution of BIO1336 t-butyl ester (0.024 g, 0.035 mmol) in methylene chloride (3.0 mL) was added trifluoroacetic acid (3.0 mL). The reaction was stirred for 2 h then concentrated. The crude product was purified by HPLC to afford BIO-1336 (0.011 g, 50%) as a white powder: $^1$H NMR (CD$_3$SOCD$_3$, 300 MHz, ppm) 8.73 (s, 1H), 8.52 (s, 1H), 8.47 (d, 8.3 Hz, 1H), 8.31 (d, 7.9 Hz, 1H), 8.11 (d, 8.3 Hz, 1H), 7.81 (d, 7.9 Hz, 1H), 7.21–7.09 (m, 2H), 7.00–6.70 (m, 5H), 5.98 (s, 2H), 5.08 (m, 1H), 4.36 (m, 1H), 3.97 (s, 3H), 3.52 (m, 2H), 2.64 (m, 2H), 2.25 (s, 3H), 1.55–1.25 (m, 3H), 0.81 (m, 6H); HPLC (Gradient B), 20.0 min; MS, m/z 620.

EXAMPLE 62

Synthesis of BIO-1382

A. To methyl 6-amino-2(S)-N-BOC-aminohexanoate hydrochloride salt (200 mg, 0.60 mmol) in CH$_2$Cl$_2$ (5 ml) and TEA (basic to litmus) is added methanesulfonyl chloride (76.2 mg, 0.67 mmol) dropwise over 2 min. at rt. Following 1 hour of stirring the reaction is diluted with CH$_2$Cl$_2$ (10 ml) partitioned 3 times with 5% citric acid (3×0.5 ml), water (1×1 ml), brine (1×1 ml), and dried over MgSO$_4$. The organic phase was concentrated in vacuo to yield 1382-1 (230 mg, 100%) as a clear oil. $^1$HNMR(CDCl$_3$, 300 MHz, ppm) 7.26 (s, 5H), 5.58 (d, 1H, J=8), 5.02 (s, 2H), 4.27 (m, 1H), 3.64 (s, 3H), 3.02 (m, 2H), 2.78 (s, 3H) 1.85–1.20 (m, 6H). HPLC (Gradient 3) 24.26 min. 98% MS, mz 373.

B. To 1382-1 (225 mg, 0.60 mmol) in 10 ml MeOH at rt with stirring is added 2N LiOH (0.91 ml, 1.8 mmol) dropwise over 2 min. Stirring is continued overnight. The reaction mixture is acidified with TFA (red to litmus) and concentrated in vacuo. The clear crude gum was taken up in EtOAc (20 ml) and worked up as described in Example 62A yielding 1382-2 (122 mg, 57%) as a clear gum.

$^1$HNMR(CDCl$_3$, 300Mz, ppm), 7.33 (s, 4H), 5.54 (d, 1H J=7.89), 4.39 (m, 1H), 3.47(S, 3H), 3.09 (m, 2H), 1.92–1.28 (m, 6H). HPLC (Gradient 3) 19.23 min. (100%). MS, mz 359.

C. The procedure described in Example 1A was performed using 1382-2 (48 mg, 0.13 mmol) and amine β-14 (25 mg, 0.09 mmol) to give 1382-3 (51 mg, 62%). $^1$HNMR (CDCl$_3$, 300 MHz, ppm), 7.97 (d, 2H J=7.38), 7.35 (m, 7H), 5.51 (m, 1H), 5.35 (dd, 1H J=5.77, 13.50), 5.09 (s, 2H), 4;75 (m, 1H), 4.14 (m, 1H), 3.88 (s, 3H), 3.62 (s, 3H), 3.09 (m, 2H), 2.73 (m, 2H), 1.92–1.77 (m, 1H), 1.70–1.55 (m, 1H), 1.551.49 (m, 2H), 1.49–1.15 (m, 13H).

D. The CBZ protecting group of compound 1382-3 was removed under catalytic hydrogenation conditions as described in Procedure D2 to give (13.2 mg, 35%) of product 1382-4. $^1$HNMR(CDCl$_3$, 300 MHz, ppm). 8.23–8.12 (m, 2H), 8.02–7.82 (m, 2H), 7.49–7.38 (m, 2H), 5.50–5.31 (m, 1H), 3.86 (s, 3H), 3.57 (s, 3H), 3.20–2.65 (m, 4H), 1.89172 (m, 1H), 1.50–1.10 (m, 14H).

E. The procedure described in Example 49 was performed using 1382-4 (15.5 mg, 0.05 mmol) to give Bio 1382 t-butyl ester (22.6 mg, 111%) as a white solid.

$^1$HNMR(CDCl$_3$, 300 MHz, ppm). 8.02 (d, 1H J=8.1), 7.87 (d, 2H J=8.0), 7.59 (d, 1H J=8.1), 7.29–7.19 (m, 5H), 7.11–7.02 (m, 4H), 6.92 (t, 1H J=7.19), 5.25–5.16 (m, 1H), 4.20–4.30 (m, 1H), 3.8 (s, 3H), 3.39 (s, 2H), 2.86–2.73 (m, 5H), 2.682.58 (m, 2H), 2.17 (s, 3H), 1.65–1.18 (m, 15H). MS, mz 752.

F. Bio 1382 t-butyl ester (27.6 mg, 0.027 mmol) is stirred in CH$_2$Cl$_2$ (1 ml) at 5° C. TFA (1.0 ml) is added in one portion; the ice bath is removed and stirring is continued for 2 hours. The reaction mixture is concentrated in vacuo and subjected to preparative HPLC purification to provide BIO-1382 (14 mg, 75%) as a white solid. $^1$HNMR(DMSO$_{D6}$, 300 MHz, ppm) 8.71(d, 1H J=7.82), 8.21 (d, 1H J=8.01), 8.04–7.91 (m, 3H), 7.59–7.44 (m, 3H), 7.32–7.20 (m, 3H), 7.01–6.98(m.2H), 5.30 (dd, 1H J=7.50, 14.93) 4.35 (m, 1H), 3.93 (s, 3H), 3.84–3.62 (m, 2H), 3.093.45 (m, 2H), 2.99–2.78 (m, 6H), 2.32 (s, 3H) 1.75–1.15 (m, 6H). HPLC (Gradient 3) 27.8 min. (95%). MS, mz 696.

EXAMPLE 63

Synthesis of BIO-1400

A. To 4-phenyl-1-butene (3.47 g, 3.94 mL, 26 mmol) at RT was added chlorosulfonyl isocynate (3.54 g, 2.17 mL, 25 mmol) under argon. The resulting mixture was stirred overnight. The reaction mixture was added dropwise to a rapidly stirring solution of NaHCO$_3$ (5 g), NaHSO$_3$ (1.5 g) and H$_2$O/CH$_2$Cl$_2$ (15 mL/10 mL) at 0° C. After 1 h, the solution was concentrated under reduced pressure and the residue was extracted with EtOAc (2×50 mL). After separation, the organic layer was washed with sat. NaCl (30 mL), dried with Na$_2$SO$_4$ and concentrated under reduced pressure to give 600 mg (14%) of the beta lactam 1400-1 as a light yellow oil: $^1$H NMR (CDCl$_3$, 300 MHz, ppm) δ 7.30–7.13 (m, 5H, Ar), 6.45 (s, 1H, NH), 3.0 (ddd, J=14.8, 4.7, 1.7 Hz, 1H), 2.64 (t, J=7.6 Hz, 2H), 2.52 (d, J=14.8 Hz, 1H), 1.92 (m, 2H); TLC, 50% Hex/EtOAc, R$_f$=0.27.

B. A solution of the beta lactam 1400-1 (500 mg, 2.86 mmol), MeOH (25 mL), and HCl (1 mL of 33%) was stirred at RT for 18 h. The reaction mixture was diluted with EtOAc (100 mL) and basified with Et$_3$N until pH=9–10 (pH paper). The resulting solution was washed with H$_2$O (10 mL), Sat. NaHCO$_3$ (30 mL), Sat. NaCl (30 mL), dried with Na$_2$SO$_4$, and concentrated under reduced pressure to give 270 mg (52%) of amine 1400-2 as a yellow oil: $^1$H NMR (CDCl$_3$, 300 MHz, ppm) δ 7.28-7.15 (m, 5H, Ar), 3.66 (s, 3H, OMe), 2.66 (m, 2H), 2.48 (dd, J=15.7, 4.0 Hz, 1H), 2.29 (dd, J=15.7, 8.8 Hz, 1H), 1.70 (m, 2H), 1.54 (s, 2H, NH); TLC, 10% MeOH/CH$_2$Cl$_2$, R$_f$=0.35; FABMS, m/z 207 (C$_{12}$H$_{17}$NO$_2$ of M$^+$1 requires 207).

C. Free amine 1400-2 (100 mg, 0.55 mmol)) was coupled with Nα-t-Boc-Nε-leu-N-hydroxysuccinimide (163 mg, 1.52 mmol) as described in Procedure C to give material which was deprotected with trifluoroacetic acid (0.5 mL) and then basified with Et$_3$N as described in Procedure D1 to give the amine 1400-3 in 95% yield: $^1$H NMR (CDCl$_3$, 300 MHz, ppm) δ 9.02 (d, J=9.0 Hz, 1H), 7.27–7.14 (m, 5H, Ar), 4.26 (m, 1H), 3.64 (s, two peaks, 3H, OMe), 3.44 (m, 1H), 2.79 (s, 2H), 2.62 (t, J=7.8 Hz, 1H), 2.54 (d, J=4.9 Hz, 1H), 1.87 (m, 2H), 1.68 (m, 2H), 1.36 (m, 1H), 0.92 (m, 6H); TLC, 10% MeOH/CH$_2$Cl$_2$, R$_f$=0.47 and 0.18; HPLC (gradient 1) 12.2 min and 13.6 min (1:1); FABMS, m/z 321 (C$_{18}$H$_{28}$N$_2$O$_3$ of M$^+$1 requires 321).

D. 2-Methylphenylureaphenylacetic acid (64 mg, 0.24 mmol) was coupled with free amine 1400-3 (64 mg, 0.20 mmol) as described in Example 49 to give compound 1400-4 in 60%: $^1$H NMR (DMSO-d$^6$, 300 MHz, ppm) δ 9.50 (d, J=6.8 Hz, 1H), 8.26–8.17 (m, 2H), 7.97 (d, J=6.1 Hz, 1H), 7.84 (d, J=8.0 Hz, 1H), 7.38-(m, 4H), 7.27–7.09 (m, 9H), 6.91 (t, J=7.3 Hz, 1H), 4.26 (m, 1H), 4.03 (m, 1H), 3.52 (s, two peaks, 3H, OMe), 3.38 (m, 2H), 2.572.40 (m, 4H), 2.25 (s, 3H), 1.70–1.41 (m, 5H), 0.86 (m, 6H); FABMS, m/z 587 (C$_{34}$H$_{12}$N$_4$O$_5$ of M$^+$1 requires 587).

E. Compound 1400-4 (70 mg, 0.119 mmol) in DMSO (1 mL) and MeOH (2 mL) was hydrolyzed with aqueous LiOH as described in Example 1B. The product was purified on a Vydac reverse-phase C1B column (22 mm×25 cm) using a linear gradient of 20% CH$_3$CN/H$_2$O (0.1% TFA) to 50% CH$_3$CN/H$_2$O (0.1% TFA) with a flow rate of 10 mL/min to give the BIO-1400 in 22% isolated yield: $^1$H NMR (DMSO-d$^6$, 300 MHz, ppm) δ 8.93 (m, 1H), 8.14 (m, 1H), 7.91–7.81 (m, 3H), 7.34 (m, 2H), 7.27–7.09 (m, 9H), 6.92 (t, J=7.4 Hz, 1H), 4.27 (m, 1H), 4.00 (m, 1H), 3.43 (d, J=14.2 Hz, 1H), 3.36 (d, J=14.2 Hz, 1H), 2.60–2.30 (m, 4H), 2.22 (s, 3H), 1.68–1.55 (m, 3H), 1.45 (t, J=6.9 Hz, 2H), 0.86 (m, 6H); HPLC (gradient 1) 20 min and 20.5 min (1:2.45); FABMS, m/z 573 ($C_{33}H_{40}N_4O_5$ of M++1 requires 573). Conditions for Analytical HPLC:

Gradient 1: a linear gradient of 20% $CH_3CN/H_2O$ (0.1% TFA) to 70% $CH_3CN/H_2O$ (0.1% TFA).

Gradient 8: a linear gradient of 15% $CH_3CN/H_2O$ (0.1% TFA) to 40% $CH_3CN/H_2O$ (0.1% TFA).

EXAMPLE 64

Inhibition of VLA4-Dependent Adhesion to BSA-CS1

This assay was used to assess the potency of VLA4-directed inhibitory compounds of this invention.

1. Conjugation of CS1 to BSA

We dissolved BSA-SMCC (Pierce Chemical, Rockford, Ill.; Catalog # 77115) in $H_2O$ at a concentration of 10 mg/mL. [SEQ ID NO:4]: Cys-Tyr-Asp-Glu-Leu-Pro-Gln-Leu-Val-Thr-Leu-Pro-His-Pro-Asn-Leu-His-Gly-Pro-Glu-Ile Leu-Asp-Val-Pro-Ser-Thr ("Cys-Tyr-CS1 peptide"), which we synthesized by conventional solid phase chemistry and purified by HPLC, was dissolved in 10 mM HEPES pH 5, 50 mM NaCl and 0.1 mM EDTA also at a concentration of 10 mg/mL. We then mixed 500 μL of BSA-SMCC, 250 μL of Cys-Tyr-CS1 peptide and 75 μL of 1 mM HEPES pH 7.5 and allowed the conjugation reaction to proceed for 30 minutes. We stopped the reaction by adding 1 μL of beta-mercaptoethanol. Samples were analyzed for cross-linking by SDS-PAGE. This reaction produced multiple molecules of the Cys-Tyr-CS1 peptide conjugate to each BSA molecule.

2. Preparation of Plates for Adhesion Assay

We coated the wells of a Linbro titertek polystyrene 96-well flat bottom plate (Flow Laboratories, Maclean, Va.; catalog #76-231-05) with 100 μL of the above-described BSA-CS1 solution diluted to 1 μg/mL in 0.05 M $NaHCO_3$ (15 mM $NaHCO_3$, 35 mM $Na_2CO_3$) pH 9.2. Some wells were not coated with CS1 in order to assess non-specific cell binding (NSB). The plate was then incubated overnight at 4° C.

Following this incubation, the contents of the wells were removed by inverting and blotting the plate. All of the wells were then blocked with 100 μL of 1% BSA in PBS, 0.02% $NaN_3$, for a minimum of one hour at room temperature.

3. Preparation of Fluorescently Labelled Ramos Cells

Ramos cells are grown, maintained and labelled in RPMI 1640 culture medium containing 1% BSA. Just prior to running the assay, we added 2',7'-bis-(2-carboxyethyl)$_5$ (and -6) carboxyfluorescein acetoxymethyl ester ("BCECF-AM"; Molecular Probes Inc., Eugene, Oreg.; catalog #B-1150) to a final concentration of 2 μM to a culture of Ramos cells (4×10$^6$ cells/mL). We incubated the cells for 20 minutes at 37° C.

Following labelling, the cells were washed twice in assay buffer (24 mM TRIS, 137 mM NaCl, 2.7 mM KCl, pH 7.4, containing 0.1% BSA and 2 mM glucose) to remove any cations originating from the culture medium. The cells were then resuspended in assay buffer to 4×10$^6$ cells/mL and 2 mM $MnCl_2$ was added to upregulate VLA4 on the surface of the cells.

4. Running the Assay

Immediately prior to running the assay, we removed the BSA blocking solution from the 96-well plates and washed the wells with 100 μL of assay buffer. We then added to each well 25 μL of test cell adhesion inhibitory compound at 2× the final concentration and 25 μL of the labelled Ramos cells. Final concentrations were selected across a range of anticipated IC50s, usually between 0.01 nM–10 μM. Each concentration of compound was tested in triplicate. The compound and cells are allowed to incubate for 30 minutes at room temperature.

We then emptied the contents of the plate and washed the wells 4 times with assay buffer. Using a light microscope, we examined the NSB wells. If more than a few cells are bound to those wells, we washed the plate once more to remove the excess non-specifically bound cells.

Binding of the Ramos cells to the CS1 peptide-coated wells was measured by adding 100 μL of assay buffer to each well and quantitating fluorescence in a Millipore Cytofluor 2300 System plate reader set at 485 nm excitation and 530=m emission. Binding was expressed as an IC50—the concentration of inhibitor at which 50% of control binding occurs. Percent binding is calculated by the formula:

$$[(F_{TP}-F_{NS})-(F_I-F_{NS})]/[(F_{TB}-F_{NS})\times 100=\% \text{ binding},$$

where $F_{TB}$ is total fluorescence bound to CS1-containing wells without added inhibitor; $F_{NS}$ is fluorescence bound in wells lacking CS1; and $F_I$ is fluorescence bound in wells containing an inhibitor of this invention.

Other compounds according to this invention were similarly assayed. The IC50 range for each of these compounds is indicated in the table below:

| BIO # | IC$_{50}$ |
|---|---|
| 1002 | nd |
| 1003 | nd |
| 1004 | C |
| 1005 | C |
| 1006 | B |
| 1007 | C |
| 1008 | C |
| 1009 | C |
| 1010 | B |
| 1011 | C |
| 1013 | nd |
| 1014 | C |
| 1015 | B |
| 1016 | C |
| 1017 | C |
| 1018 | C |
| 1020 | C |
| 1021 | B |
| 1022 | C |
| 1023 | B |
| 1024 | C |
| 1025 | nd |
| 1026 | C |
| 1027 | C |
| 1028 | B |
| 1029 | C |
| 1030 | C |
| 1031 | C |
| 1032 | C |
| 1036 | B |
| 1037 | B |
| 1038 | C |

-continued

| BIO # | IC$_{50}$ |
|---|---|
| 1039 | B |
| 1040 | B |
| 1041 | nd |
| 1042 | nd |
| 1043 | nd |
| 1044 | nd |
| 1045 | nd |
| 1046 | C |
| 1047 | nd |
| 1048 | nd |
| 1049 B | nd |
| 1050 | A |
| 1051 | nd |
| 1052 | B |
| 1053 | B |
| 1054 | B |
| 1055 | A |
| 1056 | A |
| 1057 | nd |
| 1058 | nd |
| 1060 | B |
| 1063 | B |
| 1064 | B |
| 1065 | B |
| 1066 | nd |
| 1067 | B |
| 1068 | B |
| 1069 | A |
| 1070 | B |
| 1072 | A |
| 1073 | B |
| 1074 | B |
| 1075 | B |
| 1076 | B |
| 1077 | B |
| 1078 | B |
| 1079 | A |
| 1080 | B |
| 1081 | B |
| 1082 | C |
| 1083 | nd |
| 1084 | nd |
| 1085 | C |
| 1086 | B |
| 1087 | C |
| 1088 | A |
| 1089 | A |
| 1090 | A |
| 1091 | B |
| 1092 | C |
| 1093 | C |
| 1094 | C |
| 1096 | C |
| 1097 | B |
| 1098 | C |
| 1099 | C |
| 1100 | B |
| 1101 | C |
| 1102 | nd |
| 1103 | C |
| 1104 | B |
| 1105 | B |
| 1106 | C |
| 1107 | C |
| 1108 | C |
| 1109 | C |
| 1110 | B |
| 1111 | C |
| 1112 | C |
| 1113 | C |
| 1114 | C |
| 1115 | B |
| 1116 | nd |
| 1117 | C |
| 1119 | nd |
| 1120 | nd |
| 1122 | C |

-continued

| BIO # | IC$_{50}$ |
|---|---|
| 1123 | C |
| 1124 | nd |
| 1125 | nd |
| 1126 | C |
| 1127 | B |
| 1128 | B |
| 1129 | B |
| 1130 | B |
| 1131 | B |
| 1132 | B |
| 1133 | B |
| 1134 | B |
| 1135 | A |
| 1136 | B |
| 1137 | nd |
| 1138 | B |
| 1139 | B |
| 1140 | nd |
| 1141 | nd |
| 1142 | nd |
| 1143 | C |
| 1144 | B |
| 1145 | B |
| 1146 | B |
| 1147 | B |
| 1148 | C |
| 1149 | C |
| 1150 | C |
| 1152 | nd |
| 1153 | C |
| 1154 | nd |
| 1155 | nd |
| 1156 | nd |
| 1157 | C |
| 1158 | B |
| 1159 | C |
| 1160 | B |
| 1162 | nd |
| 1163 | B |
| 1164 | B |
| 1168 | B |
| 1169 | B |
| 1170 | B |
| 1173 | B |
| 1174 | B |
| 1175 | B |
| 1176 | B |
| 1177 | B |
| 1178 | B |
| 1179 | A |
| 1180 | B |
| 1181 | B |
| 1182 | B |
| 1185 | A |
| 1186 | B |
| 1187 | C |
| 1188 | C |
| 1189 | C |
| 1190 | A |
| 1191 | B |
| 1192 | A |
| 1193 | B |
| 1194 | B |
| 1195 | A |
| 1196 | A |
| 1197 | A |
| 1198 | C |
| 1199 | B |
| 1200 | B |
| 1201 | B |
| 1206 | A |
| 1207 | C |
| 1208 | B |
| 1209 | C |
| 1210 | A |
| 1212 | A |
| 1214 | B |

-continued

| BIO # | IC$_{50}$ |
|---|---|
| 1215 | C |
| 1216 | B |
| 1217 | A |
| 1218 | B |
| 1219 | B |
| 1220 | B |
| 1221 | A |
| 1222 | A |
| 1223 | nd |
| 1224 | A |
| 1225 | nd |
| 1227 | nd |
| 1238 | A |
| 1245 | A |
| 1246 | A |
| 1248 | A |
| 1270 | A |
| 1282 | A |
| 1294 | A |
| 1321 | A |
| 1327 | B |
| 1336 | A |
| 1360 | A |
| 1380 | B |
| 1382 | A |
| 1390 | B |
| 1396 | nd |
| 1400 | A |

Table abbreviations:
A - <50 nM;
B - 50 nM–10 $\mu$M;
C - >10 $\mu$M;
nd - not determined.
All compounds tested in this table demonstrated an IC$_{50}$ < 1 mM

EXAMPLE 65

Direct Binding of VLA4-Presenting Cells to VCAM-IgG

We next examined the ability of the compounds of this invention to inhibit VCAM/VLA4 binding, utilizing a VCAM-IgG-alkaline phosphatase conjugate. To carry out this assay, we used the Millipore Multiscreen Assay System (Millipore Corp., Bedford, Mass.) to wash the cells efficiently.

1. Preparation of VCAM-IgG-AP Conjugates

The construction of VCAM 2D-IgG expression vectors, transfection of CHO cells with those constructs and purification of the resulting expression product is described in PCT publication WO 90/13300, the disclosure of which is herein incorporated by reference.

1.2 ml of purified VCAM 2D-IgG (5 mg/ml in 10 mM HEPES, pH 7.5) was reacted with 44 $\mu$l of Traut's reagent (2-iminothiolane, 20 mg/ml in water; Pierce Chemical, Rockford, Ill.) at room temperature for 30 minutes. The sameple was desalted on a 15 ml Sephadex G-25 column equilibrated with 100 mM NaCl, 10 mM MES, pH 5.0. One ml fractions were collected and absorbance at 280 nm was determined. The two peak fractions were pooled.

One ml of calf intestinal alkaline phosphatase (19 mg/ml; Pierce Chemical, Rockford, Ill.) was reacted with 100 $\mu$l of sulfo-SMCC (30 mg/ml in water) and 100 $\mu$l 1 M HEPES, pH 7.5 for 35 minutes at room temperature. The reaction mix was desalted on a 12 ml Sephadex G-25 column equilibrated with 150 mM NaCl, 10 mM HEPES, pH 6.0. One ml fractions were collected and absorbance at 280 nm was determined. The two peak fractions were pooled and stored on ice.

The alkaline phosphatase-SMCC and VCAM 2D-IgG-iminothilane adducts were cross-linked at a molar ratio of 2:1 in Tris-HCL, pH 7.5 by incubation at room temperature for 30 minutes. Extent of cross-linking was determined by SDS-PAGE. The cross-linked products were stabilized by the addition of 2 mM MgCl$_2$ and 0.25 mM ZnCl$_2$ and stored at 4° C.

2. Binding Assay

We first blocked a 96-well filtration plate for by adding 275 $\mu$L of PBS containing 0.1% Tween 20 and 2% BSA ("blocking buffer") to each well and incubating for 1 hour at room temperature. The plate was then placed onto a vacuum manifold and the blocking buffer was drained through the bottom of the filtration wells into a waste collection tray. Then we washed the wells three times with 200–250. $\mu$L of Tris-buffered saline, containing 0.1% BSA, 2 mM glucose and 1 mM HEPES, pH 7.5 ("assay buffer") to wash out any remaining blocking buffer. We then drained the plates and blotted them on paper towels to remove buffer on the underside of the plate.

We then prepared a stock solution of VCAM-IgG-AP (4 $\mu$g/mL in assay buffer) and filtered it through a 0.2$\mu$ low protein binding syringe filter (Gelman Sciences, Ann Arbor, Mich. # 4454). This solution was then diluted 1:10 in assay buffer and 25 $\mu$L was added to every well of the washed plate.

We diluted the cell adhesion inhibitor being tested to 2× final concentration in assay buffer and added 25 $\mu$L of each dilution to triplicate wells in the plate. Final concentrations used ranged from 0.01 nM-10 $\mu$M. Control wells for total binding and non-specific binding received 25 $\mu$L of assay buffer, instead of inhibitor. Total binding wells contained cells and VCAM-IgG-AP in assay buffer. Non-specific binding wells contained only VCAM-IgG-AP in assay buffer.

Jurkat cells were washed once in assay buffer to remove growth medium and resuspended at 8×10$^6$/mL in assay buffer containing 2 mM MnCl$_2$. We added 50 $\mu$l of Jurkat cells to every well, except the non-specific binding wells, which received 50 $\mu$L of assay buffer to maintain a final assay volume of 100 $\mu$L per well. We gently mixed the contents of the wells by tapping the sides of the plate. The plate was then allowed to incubate undisturbed for 60 minutes at room temperature.

At the end of the 60 minute incubation, we placed the plate on the vacuum manifold to drain the wells. We carefully added 100 $\mu$L of assay buffer containing 1 mM MnCl$_2$ (wash buffer) to each well so as not to disturb the cells on the bottom. The wash buffer was removed by vacuum and the plate was washed again with 150 $\mu$L of wash buffer. After draining the wash buffer again, the underside of the plate was blotted on paper towels.

Next, we prepared a 10 mg/mL solution of 4-nitrophenylphosphate in 0.1 M glycine, 1 mM ZnCl$_2$, pH 10.5 (substrate buffer) and added 100 $\mu$L immediately added to each well. The plate was incubated for 30 minutes at room temperature to allow the calorimetric reaction to proceed. We stopped the reaction by adding 100 $\mu$L of 3 N NaOH to each well.

The contents of the 96-well filtration plate was then transferred directly into a 96-well flat bottom plate using the vacuum manifold. The plate was read at a wavelength of 405 nm to determine the amount of VCAM conjugate bound to the cells. Percent binding is calculated by the formula:

$$[(A_{TB}-A_{NS})-(A_I-A_{NS})]/[(A_{TB}-A_{NS})\times 100=\% \text{ binding,}$$

where $A_{TB}$ is the absorbance at 405 nm of CS1-containing wells without added inhibitor; $A_{NS}$ is the absorbance at 405 nm in wells lacking CS1; and $A_I$ is absorbance at 405 nm in wells containing an inhibitor of this invention.

We assayed other compounds of this invention in the same assay. The IC50 values are comparable to those derived from the CS1 binding assay described in the previous example, although certain compounds demonstrated up to 10-fold greater binding in this assay than in the previous assay.

EXAMPLE 66

Inhibition of Mouse Contact Hypersensitivity

We anesthetized 20-g female Balb/c mice (Jackson Laboratories, Bar Harbor, Me.) with sodium pentobarbital (90 mg/kg, i.p.). A 3 cm² patch of abdominal skin was then exposed by closely shaving the fur. The skin was then scrubbed with 70% ethanol, followed by application of 25 µL of 0.5% DNFB in 4:1 v/v acetone:olive oil onto the bare abdominal skin. We then lightly scratched the skin with the applying pipet tip to encourage mild inflammation. Twenty four hours after the initial sensitization we again sensitized the mouse with 25 µL of 0.5% DNFB at same abdominal skin location, again followed by light scratching with the pipet tip. The second sensitization was performed while restraining the unanesthetized mouse.

On Day 5 (120 hours after the initial sensitization), we anesthetized the mice with 90:10 mg/kg ketamine:xylazine, i.p. and applied a sub-irritant dose of 10 µL of 0.2% DNFB to the dorsal surface of the left ear. The right ear received a similar application of the 4:1 v/v acetone:olive oil vehicle.

Four hours after challenging the immune response, we administered various concentrations of the inhibitors of this invention to the mice in 100 µL 0.5% sodium phosphate buffer, pH 8.8, and 3% v/v DMSO by subcutaneous (s.c.) injection. Less soluble inhibitors occasionally required up to 30% DMSO addition the highest concentrations tested. Groups of 8 mice were used for each treatment tested. Positive (PS2 anti-mouse VLA-4 antibody, 8 mg/kg, i.v.), and negative control (phosphate-buffered physiological saline, PBS, 100 µL i.v.; DMSO in PBS, 100 µL s.c.) groups were routinely tested for comparison as part of the assay of test compounds.

Twenty four hours after challenge mice were again anesthetized with ketamine:xylazine and the ear thickness of both ears measured with an engineer's micrometer to an accuracy of $10^{-4}$ inches. The ear swelling response for each mouse was the difference between its control- and DNFB-challenged ear thickness. Typical uninhibited ear swelling responses were $65-75 \times 10^{-4}$ in. Inhibition of the ear swelling response was judged by comparison of treated groups with their negative control group. Percent inhibition was calculated as:

$$\left[ \frac{(\text{mean negative control group ear swelling}) - (\text{mean test group ear swelling})}{\text{mean negative control group ear swelling}} \times 100 \right]$$

Statistical significance of the difference among treatment groups was evaluated using one-way analysis of variance followed by computation of the Tukey-Kramer Honestly Significant Difference (JMP, SAS Institute) using $p<0.05$.

The inhibitors of this invention cause a statistically significant reduction in the ear swelling response of DNFB-treated mice as compared to uninhibited control animals.

EXAMPLE 67

Inhibition of *Ascaris* Antigen-Induced Late Phase Airway Sensitivity in Allergic Sheep Sheep which had previously been shown to develop both early and late bronchial responses to *Ascaris suum* antigen were used in this study. The protocol used for the experiment was that described in W. M. Abraham et al., *J. Clin. Invest.*, 93, pp. 776–87 (1994), except that the VLA-4 inhibitors of this invention were administered to the animals was dissolved in 3–4 ml of 50% aqueous ethanol and delivered by aerosol spray.

The results showed that all of the VLA-4 inhibitors of this invention inhibited the airway responses associated with administration of *Ascaris suum* antigen.

While we have hereinbefore presented a number of embodiments of this invention, it is apparent that our basic construction can be altered to provide other compounds and methods which utilize the compounds of this invention. Therefore, it will be appreciated that the scope of this invention is to be defined by the claims appended hereto rather than the specific embodiments which have been presented hereinbefore by way of example.

We claim:

1. A cell adhesion inhibitory compound of formula (I):

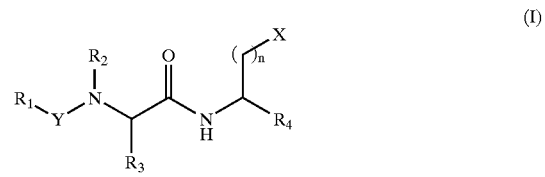

or a pharmaceutically acceptable salt thereof, wherein:

X is selected from the group consisting of —CO₂H, —SO₂R₅, and —SO₃H;

Y is —CO—;

R₁ is selected from the group consisting of alkyl, alkenyl, alkynyl, cycloalkyl, cycloalkenyl, cycloalkyl-substituted alkyl, cycloalkenyl-substituted cycloalkyl, alkoxy, alkenoxy, alkynoxy, alkylamino, alkenylamino, alkynylamino, N-alkylurea-substituted alkyl, alkylcarbonylamino-substituted alkyl, and aminocarbonyl-substituted alkyl;

R₂ is selected from the group consisting of hydrogen, alkyl, alkenyl, alkynyl, cycloalkyl, and cycloalkenyl;

R₃ is selected from the group consisting of alkyl, alkenyl, alkynyl, cycloalkyl, cycloalkenyl, hydroxy-substituted alkyl, alkoxy-substituted alkyl, amino-substituted alkyl, thiol-substituted alkyl, alkylsulfonyl-substituted alkyl, (hydroxy-substituted alkylthio)-substituted alkyl, thioalkoxy-substituted alkyl, acylamino-substituted alkyl, alkylsulfonylamino-substituted alkyl, (N-(alkyl, alkenyl or alkynyl) or N,N-(dialkyl, dialkenyl, dialkynyl or (alkyl, alkenyl)-amino)carbonyl-substituted alkyl, carboxyl-substituted alkyl, and amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, alanine, ornithine, glutamine, valine, threonine, serine, aspartic acid, beta-cyanoalanine, and allothreonine;

$R_4$ is selected from the group consisting of alkyl, cycloalkyl, alkenyl, cycloalkenyl, and alkynyl;

$R_5$ is alkyl, alkenyl, cycloalkyl, cycloalkenyl, or alkynyl; and n is 0, 1 or 2.

2. The cell adhesion inhibitory compound according to claim 1, wherein $R_1$ is selected from the group consisting of cyanomethyl, cyclohexylmethyl, methyl, n-hexyl, t-butoxy, t-butylamino, 5-(N'-t-butylurea)pentyl, and 2,2-dimethylpropyl.

3. The cell adhesion inhibitory compound according to claim 1, wherein $R_2$ is hydrogen or methyl.

4. The cell adhesion inhibitory compound according to claim 3, wherein $R_2$ is hydrogen.

5. The cell adhesion inhibitory compound according to claim 1, wherein $R_3$ is selected from the group consisting of 2-(methylsulfonyl)-ethyl, 3-(hydroxy-propylthio)-methyl, 4-(methylsulfonylamino)-butyl, 4-acetylaminobutyl, aminomethyl, butyl, hydroxymethyl, isobutyl, methyl, methylthiomethyl, propyl, N,N-(methylpropargyl)-amino, 2-(methylthio)-ethyl, 2-(N,N-dimethylamino)-ethyl, 4-aminobutyl, t-butoxy-carbonylaminomethyl, sec-butyl, t-butyl, N,N-dimethyl-aminocarbonylmethyl, 1,1-ethano, 1-hydroxyethyl, 1-methoxyethyl, carbonylmethyl, 2-methylsulfinylethyl, and asparagine side-chain.

6. The cell adhesion inhibitory compound according to claim 5, wherein $R_3$ is selected from the group consisting of isobutyl, 2-(methylthio)-ethyl, 3-(hydroxypropylthio)-methyl, 2-(methylsulfonyl)-ethyl and 4-acetylamino-butyl, 4-(methylsulfonylamino)-butyl.

7. The cell adhesion inhibitory compound according to claim 1, wherein $R_4$ is methyl.

8. The cell adhesion inhibitory compound according to claim 1, wherein n is 1.

9. A pharmaceutical composition comprising a cell adhesion inhibitory compound of formula (I):

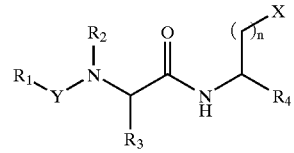

(I)

or a pharmaceutically acceptable salt thereof, wherein:

X is selected from the group consisting of —$CO_2H$, —$SO_2R_5$, and —$SO_3H$;

Y is —CO—;

$R_1$ is selected from the group consisting of alkyl, alkenyl, alkynyl, cycloalkyl, cycloalkenyl, cycloalkyl-substituted alkyl, cycloalkenyl-substituted cycloalkyl, alkoxy, alkenoxy, alkynoxy, alkylamino, alkenylamino, alkynylamino, N-alkylurea-substituted alkyl, alkylcarbonylamino-substituted alkyl, and aminocarbonyl-substituted alkyl;

$R_2$ is selected from the group consisting of hydrogen, alkyl, alkenyl, alkynyl, cycloalkyl, and cycloalkenyl;

$R_3$ is selected from the group consisting of alkyl, alkenyl, alkynyl, cycloalkyl, cycloalkenyl, hydroxy-substituted alkyl, alkoxy-substituted alkyl, amino-substituted alkyl, thiol-substituted alkyl, alkylsulfonyl-substituted alkyl, (hydroxy-substituted alkylthio)-substituted alkyl, thioalkoxy-substituted alkyl, acylamino-substituted alkyl, alkylsulfonylamino-substituted alkyl, (N-(alkyl, alkenyl or alkynyl) or N,N-(dialkyl, dialkenyl, dialkynyl or (alkyl, alkenyl)-amino)carbonyl-substituted alkyl, carboxyl-substituted alkyl, and amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, alanine, ornithine, glutamine, valine, threonine, serine, aspartic acid, beta-cyanoalanine, and allothreonine;

$R_4$ is selected from the group consisting of alkyl, cycloalkyl, alkenyl, cycloalkenyl, and alkynyl;

$R_5$ is alkyl, alkenyl, cycloalkyl, cycloalkenyl, or alkynyl; and n is 0, 1 or 2;

in an amount effective for prevention, inhibition or suppression of cell adhesion;

and a pharmaceutically acceptable carrier.

* * * * *